US007687635B2

(12) United States Patent
Verpoort et al.

(10) Patent No.: US 7,687,635 B2
(45) Date of Patent: Mar. 30, 2010

(54) METAL COMPLEXES USEFUL IN METATHESIS AND OTHER REACTIONS

(75) Inventors: Francis Walter Cornelius Verpoort, Gits (BE); Bob De Clercq, Oudenaarde (BE)

(73) Assignee: Telene S.A.S., Drocourt (FR)

( * ) Notice: Subject to any disclaimer, the term of this patent is extended or adjusted under 35 U.S.C. 154(b) by 1441 days.

(21) Appl. No.: 10/894,308

(22) Filed: Jul. 19, 2004

(65) Prior Publication Data

US 2005/0043541 A1 Feb. 24, 2005

Related U.S. Application Data

(63) Continuation-in-part of application No. PCT/BE03/00008, filed on Jan. 22, 2003.

(60) Provisional application No. 60/349,956, filed on Feb. 1, 2002.

(30) Foreign Application Priority Data

Jan. 22, 2002 (EP) .................................. 02075250

(51) Int. Cl.
C07F 15/00 (2006.01)
(52) U.S. Cl. .......................... 548/103; 556/32; 556/137
(58) Field of Classification Search .................. 556/32, 556/137; 544/64; 502/150, 200; 548/103
See application file for complete search history.

(56) References Cited

U.S. PATENT DOCUMENTS

| | | | |
|---|---|---|---|
| 5,763,548 | A | 6/1998 | Matyjaszewski et al. |
| 5,977,393 | A | 11/1999 | Grubbs et al. |
| 6,284,852 | B1 | 9/2001 | Lynn et al. |
| 6,407,187 | B1 | 6/2002 | Matyjaszewski et al. |
| 6,512,060 | B1 | 1/2003 | Matyjaszewski et al. |
| 6,541,580 | B1 | 4/2003 | Matyjaszewski et al. |
| 6,576,779 | B1 | 6/2003 | Bansleben et al. |
| 6,624,263 | B2 | 9/2003 | Matyjaszewski et al. |
| 6,696,597 | B2 | 2/2004 | Pederson et al. |
| 2002/0193538 | A1 | 12/2002 | Matyjaszewski et al. |
| 2007/0043188 | A1 | 2/2007 | Schaubroeck et al. |
| 2007/0185343 | A1 | 8/2007 | Verpoort et al. |

FOREIGN PATENT DOCUMENTS

| | | |
|---|---|---|
| EP | 0563730 A2 | 10/1993 |
| EP | 1577282 A2 | 9/2005 |
| EP | 1577282 A3 | 11/2005 |
| WO | WO 99/22856 | 5/1999 |
| WO | WO 03/062253 A1 | 7/2003 |
| WO | WO 2005/035121 | 4/2005 |

OTHER PUBLICATIONS

Bel'Skii et al., "Hydrogen Bonds of Phenol and Tert-Butyl Alcohol with Phosponic Esters," *Zhurnal Obshchei Khimii* 45(12):2606-2609 (1975).

Floch et al., "Phosphonolipids as Non-Viral Vectors for Gene Therapy," *European Journal of Medicinal Chemistry* 33:923-934 (1998).

Toreki et al., "Metathetical Reactions of RE(VII) Alkylidene-Alkylidyne Complexes of the Type $RE(CR^1)(CHR^1)[OCMe(CF_3)_2]_2$ ($R^1=CMe_3$ or $CME_2PH$) with Terminal and Internal Olefins," *Journal of the American Chemical Society* 115:127-137 (1993).

Chang et al., "Synthesis and Characterization of New Ruthenium-Based Olefin Metathesis Catalysts Coordinated with Bidentate Schiff-Base Ligands," Organometallics 17: 3460-3465(1998).

Dieltiens et al., "Pyrrole Synthesis Using a Tandem Grubbs' Carbene-RuCl3 Catalytic System," Tetrahedron Lett. 45: 8995-8998 (2004).

Gross et al., "α-Substituted Phosphonates. 37. Derivatives of α—Pyrrolomethylphosphonic Acid and N-vinylpyrroles," Chemical Abstracts [Online]: Database Accession No. 96:199787.

Hodgson et al., "Unsaturated 1,2-amino Alcohols From Dihydropyrrole Epoxides and Organolithiums," Synlett2: 310-312 (2002).

Sanford et al., "Synthesis and Reactivity of Neutral and Cationic Ruthenium(II) Tris(pyrazolyl)borate Alkylidenes," Organometallics 17: 5384-5389 (1998).

European Search Report (EP Appl. No. 06020387.4-1211) dated Dec. 8, 2006.

Garber et al., "Efficient and Recyclable Monomeric and Dendritic Ru-Based Metathesis Catalysts," *J Am. Chem. Soc.*, 122:8168-8179, 2000.

March, J., "Acids and Bases," *Advanced Organic Chemistry*, 3rd edition, Wiley, NY, 1985, pp. 220-222.

Examiner's first report on Australian patent application No. 2003236511, dated Jan. 25, 2008 (Australian Government / IP Australia).

Biradar et al., "Trinuclear Complexes of Dimethylsilane and Cobalt Schiff-Base Complexes," *Inorganica Chimica Acta*, 74:39-41 (1983).

(Continued)

*Primary Examiner*—Joseph K. McKane
*Assistant Examiner*—Jason M Nolan
(74) *Attorney, Agent, or Firm*—Clark & Elbing LLP

(57) ABSTRACT

This invention provides metal complexes being useful as catalyst components in metathesis reactions and in reactions involving the transfer of an atom or group to an ethylenically or acetylenically unsaturated compound or another reactive substrate and, with respect to a sub-class thereof, for the polymerisation of α-olefins and optionally conjugated dienes, with high activity at moderate tempera-tures. It also provides methods for obtaining polymers with very narrow molecular weight distribution by means of a living reaction. It also provides methods for making said metal complexes and novel intermediates involved in such methods. It further provides derivatives of said metal complexes which are suitable for covalent bonding to a carrier, the product of such covalent bonding being useful as a supported catalyst for heterogeneous catalytic reactions. It also provides a direct one-step synthesis of pyrrole, furan and thiophene compounds from diallyl compounds.

16 Claims, 14 Drawing Sheets

OTHER PUBLICATIONS

De Clercq et al., "Immobilization of Multifunctional Schiff Base Containing Ruthenium Complexes on MCM-41." *Applied Catalysis A.: General* 247: 345-364 (2003).

Opstal et al., "Easily Accessible Ring Opening Metathesis and Atom Transfer Radical Polymerization Catalysts based on Arene, Norbornadiene and Cyclooctadiene Ruthenium Complexes Bearing Schiff Base Ligands," *Adv. Synth. Catal.* 345:393-401 (2003).

Trnka et al., "The Development of $L_2X_2Ru=CHR$ Olefin Metathesis Catalysts: An Organometallic Success Story," *Acc. Chem. Res.* 34:18-29 (2001).

European Patent Office Communication (05447043.0-2103) dated Sep. 23, 2005.

European Search Report (EP Application Serial No. 06017332.5-2117) mailed Nov. 28, 2006.

International Preliminary Examination Report (PCT/BE 03/00008) dated Jan. 22, 2002.

International Preliminary Report on Patentability (PCT/BE2005/000030) dated Feb. 7, 2006.

International Search Report (PCT/BE2005/000030) dated Sep. 16, 2005.

International Search Report for (PCT/EP2006/008221) dated Mar. 2, 2007.

Written Opinion of the International Searching Authority (PCT/BE2005/000030) dated Sep. 16, 2005.

Written Opinion of the International Searching Authority (PCT/EP2006/008221) dated Mar. 2, 2007.

IA

IB

VI

IIA

IIB

IIIA

IIIB

IC

ID

IIIC

IIID

MCM-41 a. R = H, R' = Me
b. R = NO$_2$, R' = Me
c. R = H, R' = 2,6-Me-4-BrC$_6$H$_2$
d. R = NO$_2$, R' = 2,6-Me-4-BrC$_6$H$_2$
e. R = H, R' = 2,6-iPrC$_6$H$_3$
f. R = NO$_2$, R' = 2,6-iPrC$_6$H$_3$
S = solvent (V A)

(V B)

(V C)

(VIA)

(VIB)

(VIC)

(VII)

METAL COMPLEXES USEFUL IN METATHESIS AND OTHER REACTIONS

CROSS REFERENCE TO RELATED APPLICATIONS

This application is a continuation-in-part of International Application No. PCT/BE2003/00008, filed Jan. 22, 2003, which was published in English under PCT Article 21(2) as WO 03/062,253, which, in turn, claims the benefit of European patent application No. 02075250.7 filed Jan. 22, 2002 and U.S. provisional application Ser. No. 60/349,956 filed Feb. 1, 2002; the disclosures of which are each incorporated by reference in their entirety.

FIELD OF THE INVENTION

The present invention relates to metal complexes which are useful as catalyst components, either alone or in combination with suitable co-catalysts or initiators, in a wide variety of organic synthesis reactions including olefin metathesis reactions, acetylene metathesis reactions and reactions involving the transfer of an atom or group to an ethylenically or acetylenically unsaturated compound or another reactive substrate, such as atom or group transfer radical polymerisation or addition reactions and vinylation reactions, cyclopropanation of ethylenically unsaturated compounds, epoxidation, oxidative cyclisation, aziridination, cyclopropenation of alkynes, Diels-Alder reactions, Michael addition, aldol condensation of ketones or aldehydes, Robinson annelation, hydroboration, hydrosilylation, hydrocyanation of olefins and alkynes, allylic alkylation, Grignard cross-coupling, oxidation of organic compounds (including saturated hydrocarbons, sulfides, selenides, phosphines and aldehydes), hydroamidation, isomerization of alcohols into aldehydes, aminolysis of olefins, hydroxylation of olefins, hydride reduction, Heck reactions, and hydrogenation of olefins or ketones. The present invention also relates, preferably with respect to a sub-class of said metal complexes, to their use as a component of a catalytic system for the polymerisation of α-olefins, and optionally conjugated dienes, with high activity at moderate temperatures. The present invention also relates to obtaining polymers with extremely narrow molecular weight distribution by means of a living polymerisation reaction. The present invention also relates to methods for making said metal complexes and to novel intermediates involved in such methods. The present invention further relates to certain derivatives of the said metal complexes which are suitable for covalent bonding to a carrier, the product of such covalent bonding being useful as a supported catalyst for heterogeneous catalytic reactions. This invention also relates to a novel direct one-step synthesis of 1-hetero-2,4-cyclopentadiene compounds such as pyrrole, furan and thiophene derivatives from diallyl compounds. Finally, the invention relates to dendrimeric materials comprising metal complexes attached to a core molecule which are catalysts removable from a reaction mixture by ultrafiltration. More particularly, the present invention relates to Schiff base derivatives of ruthenium alkylidene complexes bearing N-heterocyclic carbene ligands, methods for making the same and their use as catalysts for the metathesis of numerous unsaturated hydrocarbons such as non-cyclic monoolefins, dienes, cyclic olefins and alkynes, as well as for atom transfer radical polymerisation of styrenes or (meth)acrylic esters, and for quinoline synthesis.

BACKGROUND OF THE INVENTION

Olefin metathesis is a catalytic process including, as a key step, a reaction between a first olefin and a first transition metal alkylidene complex, thus producing an unstable intermediate metallacyclobutane ring which then undergoes transformation into a second olefin and a second transition metal alkylidene complex according to equation (1) hereunder. Reactions of this kind are reversible and in competition with one another, so the overall result heavily depends on their respective rates and, when formation of volatile or insoluble products occur, displacement of equilibrium.

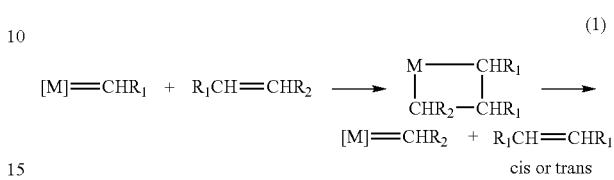

Several exemplary but non-limiting types of metathesis reactions for mono-olefins or di-olefins are shown in equations (2) to (5) herein-after. Removal of a product, such as ethylene in equation (2), from the system can dramatically alter the course and/or rate of a desired metathesis reaction, since ethylene reacts with an alkylidene complex in order to form a methylene ($M=CH_2$) complex, which is the most reactive and also the least stable of the alkylidene complexes.

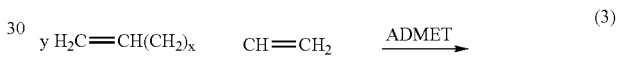

Of potentially greater interest than homo-coupling (equation 2) is cross-coupling between two different terminal olefins. Coupling reactions involving dienes lead to linear and cyclic dimers, oligomers, and, ultimately, linear or cyclic polymers (equation 3). In general, the latter reaction called acyclic diene metathesis (hereinafter referred to as ADMET) is favoured in highly concentrated solutions or in bulk, while cyclisation is favoured at low concentrations. When intramolecular coupling of a diene occurs so as to produce a cyclic alkene, the process is called ring-closing metathesis (hereinafter referred to as RCM) (equation 4). Cyclic olefins can be opened and oligomerised or polymerised (ring opening metathesis polymerisation (hereinafter referred to as ROMP) shown in equation 5). When the alkylidene catalyst reacts more rapidly with the cyclic olefin (e.g. a norbornene or a cyclobutene) than with a carbon-carbon double bond in the growing polymer chain, then a "living ring opening metathesis polymerisation" may result, i.e. there is little termination during or after the polymerization reaction.

A large number of catalyst systems comprising well-defined single component metal carbene complexes have been prepared and utilized in olefin metathesis. One major development in olefin metathesis was the discovery of the ruthenium and osmium carbene complexes by Grubbs and co-workers. U.S. Pat. No. 5,977,393 discloses Schiff base derivatives of such compounds, which are useful as olefin metathesis catalysts, wherein the metal is coordinated by a neutral electron donor, such as a triarylphosphine or a tri(cyclo)alkylphosphine, and by an anionic ligand. Such catalysts show an improved thermal stability while maintaining metathesis activity even in polar protic solvents. They are also able to cyclise diallylamine hydrochloride to dihydropyrrole hydrochloride. Remaining problems to be solved with the carbene complexes of Grubbs are (i) improving both catalyst stability (i.e. slowing down decomposition) and metathesis activity at the same time and (ii) broadening the range of organic products achievable by using such catalysts, e.g. providing ability to ring-close highly substituted dienes into tri- and tetra-substituted olefins.

On the other hand, living polymerisation systems were reported for anionic and cationic polymerisation, however their industrial application has been limited by the need for high-purity monomers and solvents, reactive initiators and anhydrous conditions. In contrast, free-radical polymerisation is the most popular commercial process to yield high molecular weight polymers. A large variety of monomers can be polymerised and copolymerised radically under relatively simple experimental conditions which require the absence of oxygen but can be carried out in the presence of water. However free-radical polymerisation processes often yield polymers with ill-controlled molecular weights and high polydispersities. Combining the advantages of living polymerisation and radical polymerisation is therefore of great interest and was achieved by the atom (or group) transfer radical polymerisation process (hereinafter referred as ATRP) of U.S. Pat. No. 5,763,548 involving (1) the atom or group transfer pathway and (2) a radical intermediate. This type of living polymerization, wherein chain breaking reactions such as transfer and termination are substantially absent, enables control of various parameters of the macromolecular structure such as molecular weight, molecular weight distribution and terminal functionalities. It also allows the preparation of various copolymers, including block and star copolymers. Living/controlled radical polymerization requires a low stationary concentration of radicals in equilibrium with various dormant species. It makes use of novel initiation systems based on the reversible formation of growing radicals in a redox reaction between various transition metal compounds and initiators such as alkyl halides, aralkyl halides or haloalkyl esters. ATRP is based on a dynamic equilibrium between the propagating radicals and the dormant species which is established through the reversible transition metal-catalysed cleavage of the covalent carbon-halogen bond in the dormant species. Polymerisation systems utilising this concept have been developed for instance with complexes of copper, ruthenium, nickel, palladium, rhodium and iron in order to establish the required equilibrium.

Due to the development of ATRP, further interest appeared recently for the Kharash reaction, consisting in the addition of a polyhalogenated alkane across an olefin through a radical mechanism (first published by Kharash et al. in *Science* (1945) 102:169) according to the following scheme (wherein X may be hydrogen or

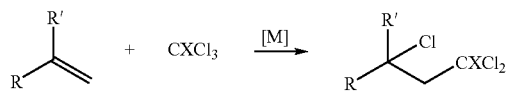

chloro or bromo, and R and R' may be each independently selected from hydrogen, $C_{1-7}$ alkyl, phenyl and carboxylic acid or ester):

Because ATRP is quite similar to the Kharasch reaction, the latter may also be called Atom Transfer Radical Addition (hereinafter referred as ATRA) and attracted interest in transition metal catalysis. Research in this field also focused on the use of new olefins and telogens and a wide range of internal, terminal and cyclic olefins and diolefins were tested with a wide range of polyhalides including fluoro, chloro, bromo and iodo as halogen atoms, as described for instance in *Eur. Polym. J.* (1980) 16:821 and *Tetrahedron* (1972) 28:29.

Experiments have shown that the efficiency of ruthenium alkylidene complexes in olefin metathesis reactions is inversely proportional to their activity in ATRP and ATRA, i.e. the most efficient catalysts for olefin metathesis reactions display the lowest activity in ATRP and ATRA. Therefore, there is a need in the art for a catalyst component which is able to display a high efficiency both in olefin metathesis reactions and in ATRP and ATRA. There is also a need in the art for a catalyst component which is able to initiate olefin metathesis reactions under very mild conditions, e.g. at room temperature. Finally there is also a need in the art for a catalyst component which is able to initiate vinylation reactions with high efficiency.

Furthermore, since presently available synthetic routes to the catalysts of U.S. Pat. No. 5,977,393 proceed through the transformation of a ruthenium bisphosphane carbene, the development of catalysts with equivalent or better performance characteristics but synthesised directly from less expensive and readily available starting materials, including from other transition metals, still corresponds to a need in the art.

Poly-α-olefins such as polyethylene, polypropylene and copolymers of ethylene with propylene and/or but-1-ene are very widely used in various fields such as extruded, co-extruded and moulded products of all kinds. The demand for poly-α-olefins with various physical properties is continuously expanding. Therefore, in order to improve their manufacturing productivity, the increase of polyolefin yield per catalyst amount and the maintenance of catalytic activity over time during continuous production remain important issues. WO 02/02649 discloses an olefin polymerisation catalytic system comprising (A) a transition metal compound, preferably wherein the transition metal is titanium, zirconium or hafnium, having a bidentate ligand including an imine structure moiety, (B-1) a compound having a reduction ability which reacts with compound (A) to convert said imine structure moiety into a metal amine structure, and (B-2) a compound which reacts with compound (A) to form an ion pair. However, WO 02/02649 does not teach a transition metal compound wherein the metal is coordinated with a carbene ligand. Therefore there is still a need in the art for improving the olefin polymerisation catalytic activity, and maintenance thereof over time, with respect to the teaching of WO 02/02649.

The Friedlaender reaction consists of quinoline synthesis through oxidative cyclisation of 2-aminobenzyl alcohol with ketones. Exemplary ketones which may be cyclised into quinolines include acetophenone, 3-methylacetophenone, cyclohexanone, 4-phenylcyclohexanone and propiophenone and other ketones such as disclosed by Cho et al. in *Chem. Commun.* (2001) 2576-2577. There is a need in the art for developing new catalysts providing higher yields, under equivalent reaction conditions, in the Friedlaender reaction.

All the above needs constitute the various goals to be achieved by the present invention.

SUMMARY OF THE INVENTION

The present invention is based on the unexpected finding that improved olefin metathesis catalysts can be obtained by modifying the Schiff base derivatives of ruthenium and osmium of the prior art, or the corresponding derivatives of other transition metals, by providing as a ligand a constraint steric hindrance group having a $pK_a$ of at least about 15 and/or by providing a carbene ligand forming a fused aromatic ring system and/or by providing a cumulylidene group as a carbene ligand. Advantageously, such modified Schiff base derivatives of ruthenium, osmium and other transition metals may be produced directly from less expensive and more readily available starting materials than the catalysts of the prior art. The present invention is also based on the unexpected finding that these modified Schiff base derivatives of ruthenium, osmium and other transition metals are not only efficient olefin and acetylene metathesis catalysts but also very efficient components in the catalysis or initiation of reactions involving the transfer of an atom or group to an ethylenically or acetylenically unsaturated compound or another reactive substrate, such as of atom (or group) transfer radical (e.g. ATRP or ATRA), as well as vinylation reactions (e.g. enol-ester synthesis), cyclopropanation of ethylenically unsaturated compounds, epoxidation, oxidative cyclisation, aziridination, cyclopropenation of alkynes, Diels-Alder reactions, Michael addition, aldol condensation of ketones or aldehydes, Robinson annulation, hydroboration, hydrosilylation, hydrocyanation of olefins and alkynes, allylic alkylation, Grignard cross-coupling, oxidation of organic compounds (including saturated hydrocarbons, sulfides, selenides, phosphines and aldehydes), hydroamidation, isomerization of alcohols into aldehydes, aminolysis of olefins, hydroxylation of olefins, hydride reduction, Heck reactions, and hydrogenation of olefins or ketones. A further unexpected finding of the present invention is that certain Schiff base derivatives of ruthenium and osmium of the prior art, as well as the corresponding derivatives of other transition metals, may also be used in the catalysis or initiation of reactions involving the transfer of an atom or group to an ethylenically or acetylenically unsaturated compound or another reactive substrate, such as atom (or group) transfer radical reactions (e.g. ATRP or ATRA), as well as vinylation reactions (e.g. enol-ester synthesis), cyclopropanation of ethylenically unsaturated compounds, epoxidation, oxidative cyclisation, aziridination, cyclopropenation of alkynes, Diels-Alder reactions, Michael addition, aldol condensation of ketones or aldehydes, Robinson annelation, hydroboration, hydrosilylation, hydrocyanation of olefins and alkynes, allylic alkylation, Grignard cross-coupling, oxidation of organic compounds (including saturated hydrocarbons, sulfides, selenides, phosphines and aldehydes), hydroamidation, isomerization of alcohols into aldehydes, aminolysis of olefins, hydroxylation of olefins, hydride reduction, Heck reactions, and hydrogenation of olefins or ketones. Also included in this invention are novel intermediates involved in the methods for preparing the novel catalytically active modified Schiff base derivatives. Further aspects of the invention include supported catalysts for use in heterogeneous catalytic reactions comprising a catalytically active Schiff base derivative and a carrier suitable for supporting the same. In particular the invention provides derivatives wherein the Schiff base metal complexes are further chemically modified in order to be suitable for covalent bonding to a carrier such as a porous inorganic solid (e.g. an amorphous or paracrystalline material, a crystalline molecular sieve or a modified layered material including an inorganic oxide) or an organic polymer resin.

Another aspect of the invention includes, in order for the catalyst to be suitably removed from a reaction mixture by ultra-filtration, dendrimeric materials wherein two or more of the catalytically active Schiff base derivatives are attached to a core molecule. Finally, another finding of this invention is that certain bimetallic Schiff base derivatives of transition metals are able to act as catalysts in the direct one-step synthesis of 1-hetero-2,4-cyclopentadiene compounds such as pyrrole, furan and thiophene derivatives from diallyl compounds without, unlike for the corresponding monometallic Schiff base catalysts, ending the reaction with the dihydropyrrole, dihydrofuran or dihydrothiophene compounds. Yet another finding of this invention is that some of the metal complexes described herein may be used as components of a catalytic system for the polymerisation of α-olefins and/or conjugated dienes with high activity at moderate temperatures.

DEFINITIONS

Figure 1:
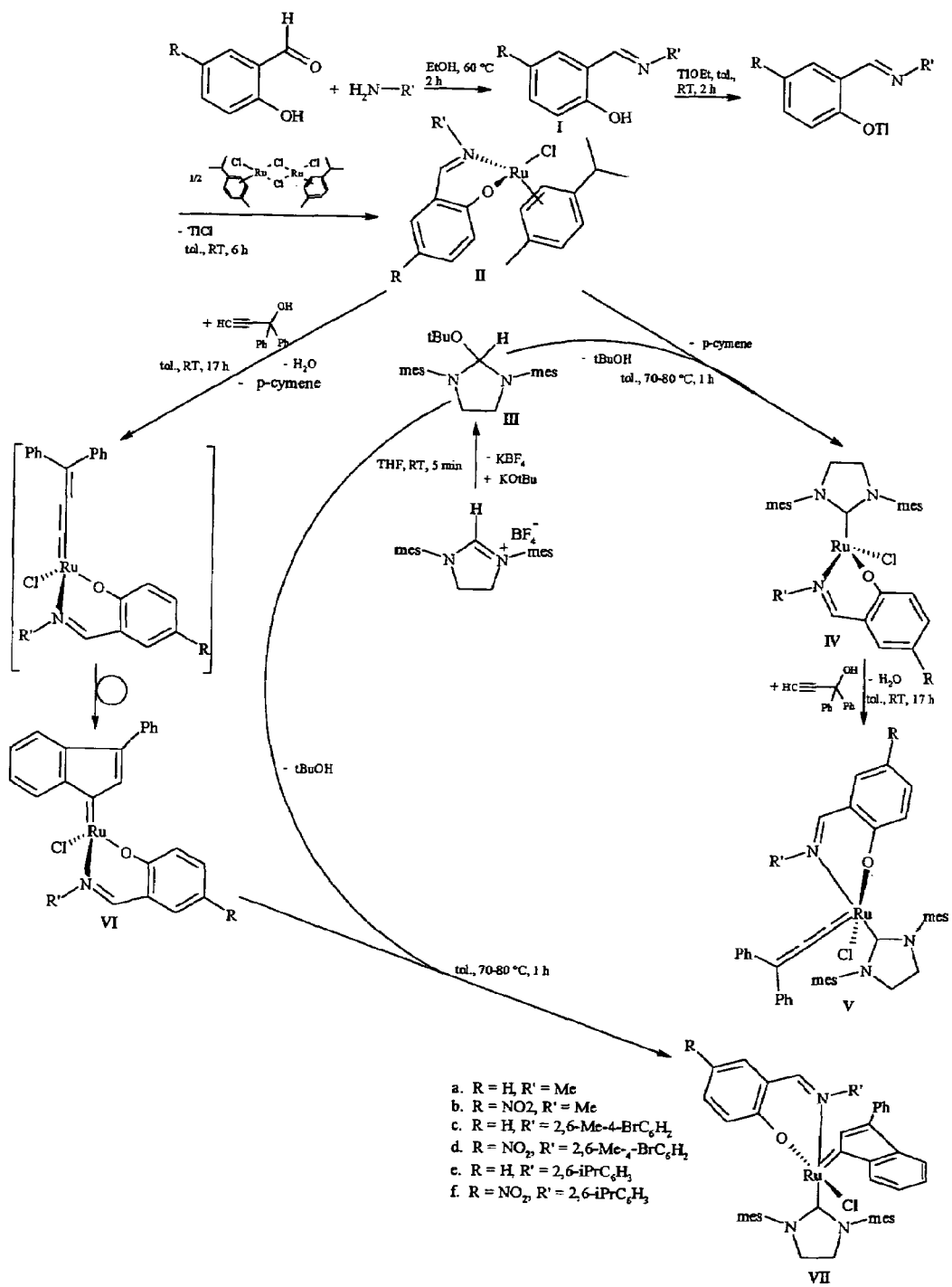
FIG. 1 schematically shows synthetic routes for producing ruthenium catalytic compounds having the general formula (IA) according to an embodiment of the present invention.

As used herein, the term complex, or coordination compound, refers to the result of a donor-acceptor mechanism or Lewis acid-base reaction between a metal (the acceptor) and several neutral molecules or ionic compounds called ligands, each containing a non-metallic atom or ion (the donor). Ligands that have more than one atom with lone pairs of electrons (i.e. more than one point of attachment to the metal center) and therefore occupy more than one coordination site are called multidentate ligands. The latter, depending upon the number of coordination sites occupied, include bidentate, tridentate and tetradentate ligands.

As used herein, the term "monometallic" refers to a complex in which there is a single metal center.

As used herein, the term "heterobimetallic" refers to a complex in which there are two different metal centers. As used herein, the term "homobimetallic" refers to a complex having two identical metal centers, which however need not have identical ligands or coordination number.

As used herein with respect to a substituting radical, ligand or group, the term "$C_{1-6}$ alkyl" means straight and branched chain saturated hydrocarbon monovalent radicals having from 1 to 6 carbon atoms such as, for example, methyl, ethyl, propyl, n-butyl, 1-methylethyl, 2-methylpropyl, 1,1-dimethylethyl, 2-methylbutyl, n-pentyl, dimethylpropyl, n-hexyl, 2-methylpentyl, 3-methylpentyl and the like; $C_{2-6}$ alkyl means analogue radicals having from 2 to 6 carbon atoms, and so on.

As used herein with respect to a linking group, the term "$C_{1-6}$ alkylene" means the divalent hydrocarbon radical corresponding to the above defined $C_{1-6}$ alkyl, such as methylene, bis(methylene), tris(methylene), tetramethylene, hexamethylene and the like.

As used herein with respect to a substituting radical, ligand or group, the term "$C_{3-10}$ cycloalkyl" means a monocyclic saturated aliphatic monovalent radical having from 3 to 8 carbon atoms, such as for instance cyclopropyl, cyclobutyl, methylcyclobutyl, cyclopentyl, methylcyclopentyl, cyclohexyl, methylcyclohexyl, cycloheptyl, cyclooctyl and the like, or a $C_{7-10}$ polycyclic saturated aliphatic monovalent radical having from 7 to 10 carbon atoms such as, for instance, norbornyl, fenchyl, trimethyltricycloheptyl or adamantyl.

As used herein with respect to a linking group, the term "$C_{3-10}$ cycloalkylene" means the divalent hydrocarbon radical corresponding to the above defined $C_{3-10}$ cycloalkyl such as but not limited to 1,2-cyclohexylene and 1,4-cyclohexylene.

As used herein with respect to a substituting radical, ligand or group, the term "aryl" means a mono- and polycyclic aromatic monovalent hydrocarbon radical having from 6 to 30 carbon atoms such as phenyl, naphthyl, anthracenyl, phenantracyl, fluoranthenyl, chrysenyl, pyrenyl, biphenylyl, picenyl, indenyl, biphenyl, indacenyl, benzocyclobutenyl, benzocyclooctenyl and the like, including fused benzo-$C_{4-8}$ cycloalkyl radicals such as, for instance, indanyl, tetrahydronaphtyl, fluorenyl and the like, all of the said radicals being optionally substituted with one or more substituents selected from the group consisting of halogen, amino, nitro, hydroxyl, sulfhydryl and nitro, such as but not limited to 4-fluorophenyl, 4-chlorophenyl, 3,4-dichlorophenyl, 2,6-di-isopropyl-4-bromophenyl, pentafluorophenyl, 4-cyanophenyl and the like.

As used herein with respect to a linking group, and unless otherwise stated, the term "arylene" means the divalent hydrocarbon aromatic radical corresponding to the above defined aryl, such as phenylene, naphtylene and the like.

As used herein with respect to a combination of two substituting hydrocarbon radicals, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring; for instance the said combination forms a $C_{2-6}$ alkylene radical, such as tetramethylene, which cyclizes with the carbon atoms to which the said two substituting hydrocarbon radicals are attached.

As used herein with respect to a substituting radical, ligand or group, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphto-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzo-quinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypoxanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzooxepinyl, dibenzopyranonyl, dibenzoquinoxalinyl, dibenzothiazepinyl, dibenzoisoquinolinyl, tetraaza-adamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpho-linyl, azlactonyl, naphtindazolyl, naphtindolyl, naphtothiazolyl, naphtothioxolyl, naphtoxindolyl, naphtotriazolyl, naphtopyranyl, oxabicycloheptyl, azabenz-imidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothio-pyranyl, benzoxazinyl, benzoxazolyl, benzodioxolyl, benzodioxanyl, benzothiadiazolyl, benzotriazinyl, benzothiazolyl, benzoxazolyl, pheno-thioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyi, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzo-chromonyl, benzisoalloxazinyl, benzocoumarinyl, thiocoumarinyl, phenometoxazinyl, phenoparoxazinyl, phentriazinyl, thio-diazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenyl-amino, alkynylamino, arylamino, arylalkylamino, hydroxylalkylamino, mercaptoalkylamino, heterocyclic amino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkyl-amino, mercaptoalkylamino, heterocyclic amino, hydrazino, alkylhydrazino, phenylhydrazino, sulfhydryl, $C_{1-7}$ alkoxy, $C_{3-10}$ cycloalkoxy, aryloxy, arylalkyl-oxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 membered ring, heterocyclic radicals may be sub-divided into heteroaromatic (or "heteroaryl") radicals and non-aromatic heterocyclic radicals; when a heteroatom of the said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, ligand or group, the term "$C_{1-6}$ alkoxy" means a $C_{1-6}$ alkyl radical attached to an oxygen atom, such as methoxy, ethoxy, n-propoxy, isopropoxy, n-butoxy, isobutoxy, tert-butoxy, amyloxy and the like; $C_{2-6}$ alkoxy means analogue radicals having from 2 to 6 carbon atoms, and so on.

As used herein with respect to a substituting ligand or atom, the term halogen means any atom selected from the group consisting of fluorine, chlorine, bromine and iodine.

As used herein with respect to a substituting radical, ligand or group, the term "$C_{1-20}$ alkyl" includes $C_{1-6}$ alkyl (as hereinabove defined) and the higher (straight or branched) homologues thereof having 7 to 20 carbon atoms, such as but not limited to, heptyl, ethylhexyl, octyl, nonyl, decyl, dodecyl, hexadecyl, octadecyl and the like.

As used herein with respect to a substituting radical, ligand or group, the term "halo $C_{1-20}$ alkyl" defines a $C_{1-20}$ alkyl in which each hydrogen atom may be independently replaced by a halogen atom (preferably fluorine or chlorine), such as difluoromethyl, trifluoromethyl, trifluoroethyl, octafluoropentyl, dodecafluoroheptyl, heptadecafluorooctyl and the like.

As used herein with respect to a substituting radical, ligand or group, the term "$C_{2-20}$ alkenyl" defines straight and branched chain hydrocarbon monovalent radicals containing one or more double bond(s) (ethylenical unsaturations) and having from 2 to 20 carbon atoms such as, but not limited to, vinyl, 1-propenyl, 2-propenyl(allyl), 3-butenyl, 2-butenyl, 1-butenyl, 2-pentenyl, 3-pentenyl, 3-methyl-2-butenyl, 3-hexenyl, 2-hexenyl, 2-heptenyl, 2-octenyl, 2-decenyl, 1,3-butadienyl, pentadienyl, hexadienyl, heptadienyl, heptatrienyl and the like, and all possible isomers thereof, As used herein with respect to a substituting radical, ligand or group, the term "$C_{3-10}$ cycloalkenyl" defines monocyclic hydrocarbon monovalent radicals containing one or more double bonds (i.e. mono- or polyunsaturated) and having from 3 to 10 carbon atoms such as, but not limited to, cyclopropenyl, cyclobutenyl, cyclopentenyl, cyclohexenyl, cycloheptenyl, cyclooctenyl, cyclooctadienyl, cyclopentadienyl, cyclooctatrienyl, 1,3,5,7-cyclooctatetraenyl and the like, or a $C_{7-10}$ polycyclic mono- or polyunsaturated hydrocarbon monovalent radical having from 7 to 10 carbon atoms such as dicyclopentadienyl, fenchenyl (including all isomers thereof, such as α-pinolenyl), bicyclo[2.2.1]hept-2-enyl (norbomenyl), bicyclo[2.2.1]hepta-2,5-dienyl(norbomadienyl), cyclofenchenyl and the like.

As used herein with respect to a substituting radical, ligand or group, the term "$C_{2-20}$ alkynyl" defines straight and branched chain hydrocarbon radicals containing one or more triple bonds (acetylenic unsaturations) and optionally at least one double bond (ethylenic unsaturation) and having from 2 to 20 carbon atoms such as, for example, acetylenyl, 1-propynyl, 2-propynyl, 3-butynyl, 2-butynyl, 1-butynyl, 2-pentynyl, 3-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like and all possible isomers thereof.

As used herein with respect to a substituting radical, ligand or group, the term "$C_{1-20}$ alkoxy" means the higher homologues of $C_{1-6}$ alkoxy (as hereinabove defined) having up to 20 carbon atoms, such as octyloxy, decyloxy, dodecyloxy, hexadecyloxy, octadecyloxy and the like and all possible isomers thereof.

As used herein, and unless otherwise stated, the terms "arylalkyl", "arylalkenyl" and "heterocyclic-substituted alkyl" refer to an aliphatic saturated or unsaturated hydrocarbon monovalent radical (preferably a $C_{1-6}$ alkyl or $C_{2-6}$ alkenyl radical such as defined above, i.e. optionally the carbon chain length of such group may be extended to 20 carbon atoms) onto which an aryl or heterocyclic radical (such as defined above) is already bonded, and wherein the said aliphatic radical and/or the said aryl or heterocyclic radical may be optionally substituted with one or more substituents selected from the group consisting of halogen, amino, nitro, hydroxyl, sulfhydryl and nitro, such as but not limited to benzyl, 4-chlorobenzyl, phenylethyl, 1-amino-2-phenylethyl, 1-amino-2-[4-hydroxyphenyl]ethyl, 1-amino-2-[indol-2-yl]ethyl, styryl, pyridylmethyl, pyridylethyl, 2-(2-pyridyl)isopropyl, oxazolylbutyl, 2-thienylmethyl and 2-furylmethyl.

As used herein, and unless otherwise stated, the terms "alkylcycloalkyl", "alkenyl(hetero)aryl", "alkyl(hetero)aryl", and "alkyl-substituted heterocyclic" refer respectively to an aryl, heteroaryl, cycloalkyl or heterocyclic radical (such as defined above) onto which are already bonded one or more aliphatic saturated or unsaturated hydrocarbon monovalent radicals, preferably one or more $C_{1-6}$ alkyl, $C_{2-6}$ alkenyl or $C_{3-10}$ cycloalkyl radicals as defined above, such as, but not limited to, o-toluyl, m-toluyl, p-toluyl, 2,3-xylyl, 2,4xylyl, 3,4-xylyl, o-cumenyl, m-cumenyl, p-cumenyl, o-cymenyl, m-cymenyl, p-cymenyl, mesityl, lutidinyl (i.e. dimethylpyridyl), 2-methylaziridinyl, methylbenzimidazolyl, methylbenzofuranyl, methylbenzothiazolyl, methylbenzotriazolyl, methylbenzoxazolyl, methylcyclohexyl and menthyl.

As used herein with respect to a substituting radical, ligand or group, the terms "alkylammonium" and "arylammonium" mean a tetra-coordinated nitrogen atom being linked to $C_{1-6}$ alkyl, $C_{3-10}$ cycloalkyl, aryl or heteroaryl groups, such as above defined, respectively.

Figure 2:
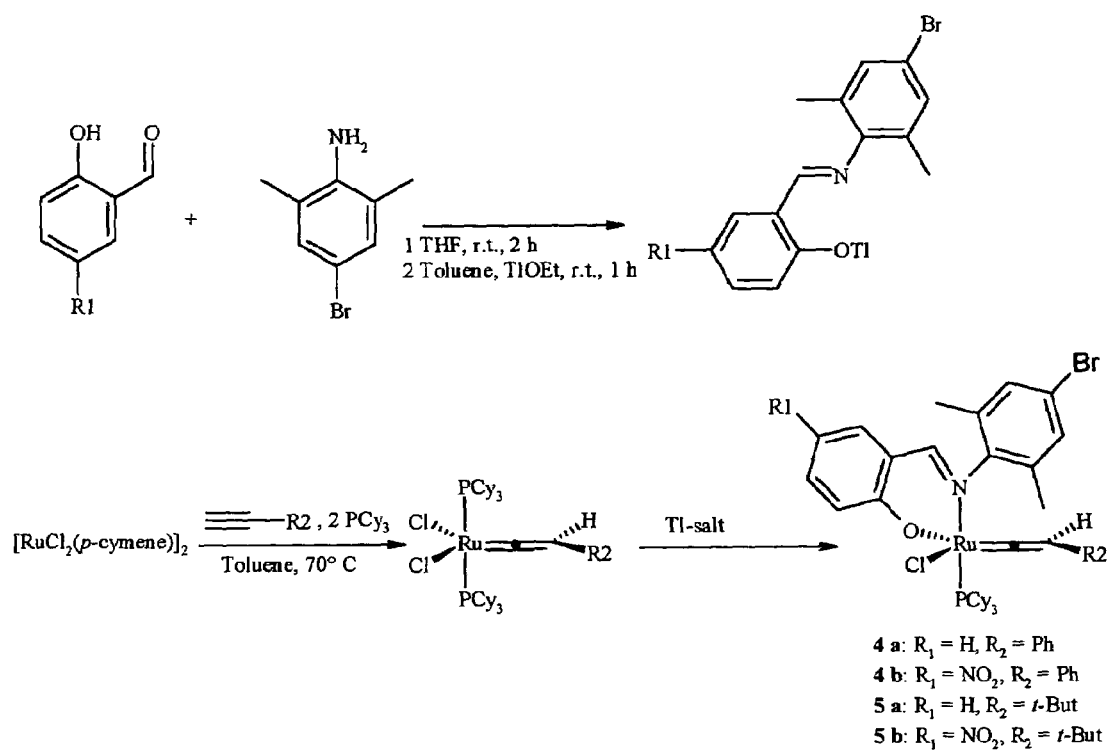
FIG. 2 schematically shows a synthetic route for producing ruthenium catalytic compounds having the general formula (IC) according to another embodiment of the present invention.
Figure 3:
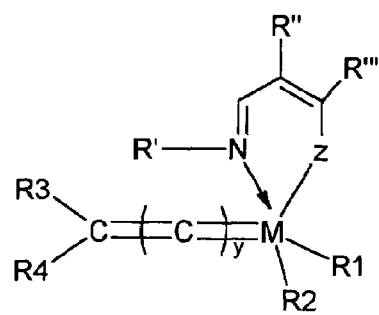
FIG. 3 shows the general chemical formulae (IA) and (IB) of monometallic complexes, the general chemical formulae (IVA) and (IVB) of bimetallic complexes of the invention, and the formula (VI) of a fused ring system which radicals $R_3$ and $R_4$ may form together in formulae (IA) and (IB).
Figure 3:
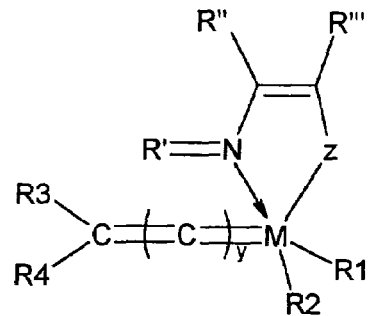
Figure 3:
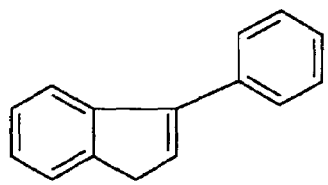
Figure 3:
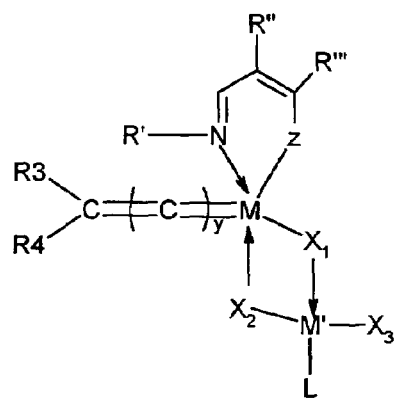
Figure 3:
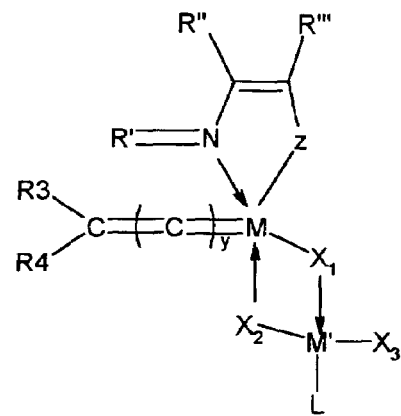
Figure 5:
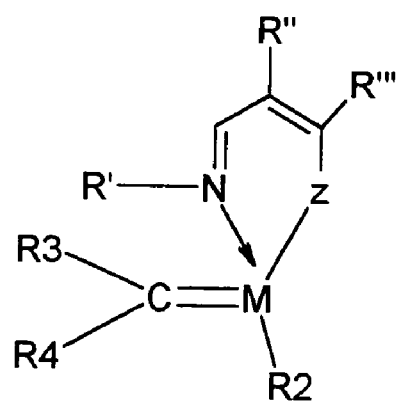
FIG. 5 shows the general chemical formulae (IIIC) and (IIID) of monometallic intermediate complexes of this invention.
Figure 5:
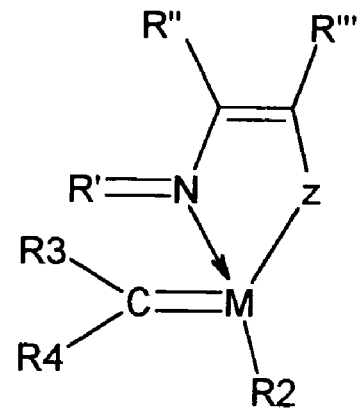
Figure 6:
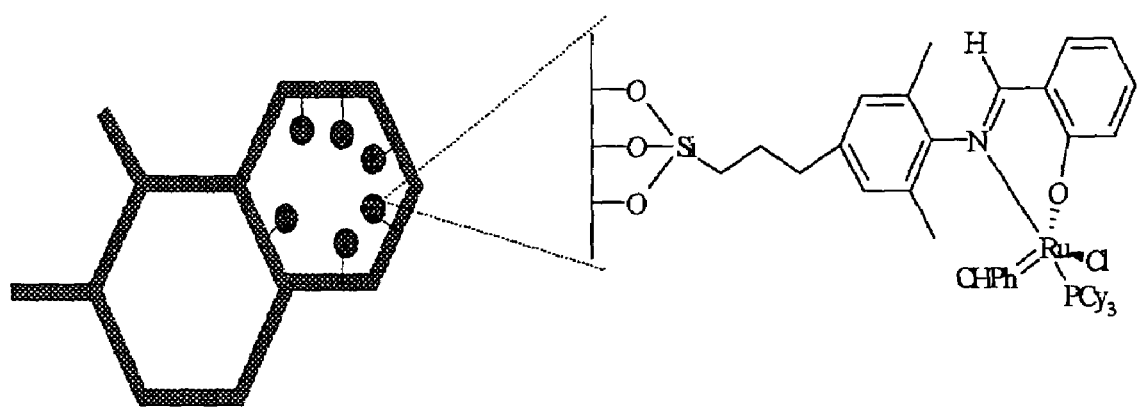
FIG. 6 schematically shows the anchoring of a derivative of a monometallic complex of the invention to a mesoporous crystalline molecular sieve.

As used herein with respect to a metal ligand, and unless otherwise stated, the term "Schiff base" conventionally refers to the presence of an imino group (usually resulting from the reaction of a primary amine with an aldehyde or a ketone) in the said ligand, preferably being part of a multidentate ligand which may be coordinated to the metal, in addition to the nitrogen atom of said irnino group, through at least one further heteroatom selected from the group consisting of oxygen, sulfur, selenium, nitrogen, phosphorus, arsenic and antimony. The said multidentate ligand may be for instance:

- a N,O-bidentate Schiff base ligand such as a lumazine or substituted lumazine or 2-(2-hydroxyphenyl)benzoxazole or (2'-hydroxyphenyl)-2-thiazoline, or
- a N,S-bidentate Schiff base ligand such as a thiolumazine or substituted thioluminazine, or
- a N,N-bidentate ligand such as a bis(oxazoline), a bipyridine or a Schiff base ligand such as may be obtained for instance through the condensation of 1,3-diaminopropane and pyrrole-2-carboxaldehyde, or
- a N,P-bidentate Schiff base ligand such as a phosphinooxazoline, or
- a N,Z-bidentate Schiff base ligand such as shown in figure 1, wherein Z is or includes an atom selected from the group consisting of oxygen, sulfur, selenium, nitrogen, phosphorus, arsenic and antimony; it may be advantageous for the said bidentate Schiff base ligand to further include a carbon-carbon double bond conjugated with the carbon-nitrogen double bond of the imino group, for instance as shown in FIG. 1, or
- a N,N,O—tridentate Schiff base ligand such as derived from 6-amino-5-formyl-1,3-dimethyluracil and semicarbazide or acetylhydrazine or benzoylhydrazine, or such as derived from 7-forrnyl-8-hydroxyquinoline(oxine) and 2-aminophenol or 2-aminopyridine, or
- a O,N,O-tridentate Schiff base ligand such as 6-arnino-5-formyl-1,3-dirnethyluracil-benzoyl-hydrazone or such as shown in formula (IV) of figure 5 or methoxyphenyl) salicylideneamine or salicyclaldehyde-2-hydroxanil or the heterocyclic Schiff base resulting from the reaction of 1-amino-5-benzoyl-4-phenyl-1H pyrimidin-2-one with 2-hydroxynaphtaldehyde or the thenoyltrifluoroaceto antipyrine Schiff base resulting from the reaction of thenoyl-trifluoroacetone with 4-aminoantipyrine, or
- a O,N,S-tridentate Schiff base ligand such as salicyialdehyde-2-rnercaptoanil, S-benzyl-2-[(2-hydroxyphenyl) methylene]dithiocarbazate or 2-11(2-hydroxyphenyl) rnethylene]-N-phenyl-hydrazinecarbothioamide, or
- a N,N,S-tridentate Schiff base ligand such as 6-amino-5-formyl-1,3-dirnethyluracilthio-semicarbazonate, or
- a N,N,N-tridentate Schiff base ligand such as a pyridine bisoxazoline or aminoethylimino)(phenyl)rnethyl]pyridine or tris(pyrazolyl)borate or as resulting from the reaction of 2-amino-1,3,4-thiadiazole with pyrrole-2-carboxaldehyde, or
- a N,N,P-tridentate Schiff base ligand such as a phosphino-2-oxazolinylquinoline. By extension, the term "Schiff base" also refers to Schiff base ligands with thioether or coumarin groups. The multidentate ligand may include more than one Schiff base, for instance as shown in figures 2 and 3, thus possibly resulting in O,N,N,O-tetradentate or O,N,N,N-tetradentate or N,N,N,N-tetradentate Schiff base ligands.

As used herein, the terms "constraint steric hindrance" relates to a group or ligand, usually a branched or substituted group or ligand, which is constrained in its movements, i.e. a group the size of which produces a molecular distortion (either an angular distortion or a lengthening of bonds) being measurable by X-ray diffraction.

As used herein, the term "enantiomer" means each individual optically active form of a compound of the invention, having an optical purity (as determined by methods standard in the art) of at least 80%, preferably at least 90% and more preferably at least 98%.

As used herein, the term "solvate" refers to the association of a metallic complex of this invention together with a molecule of a solvent selected from the group consisting of protic solvents, polar aprotic solvents and non-polar solvents such as aromatic hydrocarbons (e.g. toluene), chlorinated hydrocarbons, ethers (e.g. tetrahydrofuran), aliphatic hydrocarbons, alcohols (e.g. isopropanol), esters (e.g. ethyl acetate), ketones (e.g. acetone or methylethylketone), amides (e.g. dimethylformamide), nitriles (e.g. acetonitrile), sulfur-containing compounds (e.g. dimethylsulfoxide) and water, as well as cyclic and non-cyclic, aromatic and non-aromatic amines (e.g. pyridine or triethylamine).

DETAILED DESCRIPTION OF THE INVENTION

In its broadest acceptation, the present invention relates to a five-coordinate metal complex, a saft, a solvate or an enantiomer thereof, comprising a carbene ligand, a multidentate ligand and one or more other ligands, wherein at least one of said other ligands is a constraint steric hindrance ligand having a pKa of at least about 15. This five-coordinate metal complex may be either a monometallic complex or a bimetallic complex wherein one metal is penta-coordinated and the other metal is tetra-coordinated with one or more neutral ligands and one or more anionic ligands. In the latter case, the two metals may be the same or different. The multidentate ligand may be either a bidentate ligand, in which case the metal complex of the invention comprises two other ligands, or a tridentate ligand in which case the metal complex comprises a single other ligand.

Preferably the metal in the five-coordinate metal complex of the invention is a transition metal selected from the group consisting of groups 4, 5, 6, 7, 8, 9, 10, 11 and 12 of the Periodic Table. More preferably the said metal is selected from the group consisting of ruthenium, osmium, iron, molybdenum, tungsten, titanium, rhenium, technetium, lanthanum, copper, chromium, manganese, palladium, platinum, rhodium, vanadium, zinc, cadmium, mercury, gold, silver, nickel and cobalt.

Preferably the multidentate ligand in the five-coordinate metal complex of the invention includes at least two heteroatoms, for instance three heteroatoms, through which coordination with the metal occurs. More preferably, at least one of the at least two heteroatoms is a nitrogen atom. Most preferably, one of the at least two heteroatoms is a nitrogen atom and the other heteroatom(s) is (are) oxygen or sulfur atoms.

The carbene ligand in the five-coordinate metal complex of the invention may be either an allenylidene ligand or a cumulenylidene ligand, e.g. buta-1,2,3-trienylidene, penta-1,2,3,4-tetraenylidene and the like.

In one aspect which is namely useful when the complex is to be used in the presence of an organic solvent, one of said other ligands present in the five-coordinate metal complex of the invention is an anionic ligand, the meaning of the term anionic ligand being conventional in the art and preferably being consistent with the definition given in U.S. Pat. No. 5,977,393. In another aspect, which is namely useful when the complex is to be used in the presence of water, one of said other ligands is a solvent and the complex is a cationic species associated with an anion. Suitable anions for the latter purpose may be for instance selected from the group consisting of tetrafluoroborate, tetra(pentafluorophenyl)borate, alkylsulfonates wherein the alkyl group may be substituted with one or more halogen atoms, and arylsulfonates. Suitable solvents for coordinating with the metal in such a cationic species may be selected from the group consisting of protic solvents, polar aprotic solvents and non-polar solvents referred to in the definition of solvates, such as but not limited to aromatic hydrocarbons, chlorinated hydrocarbons, ethers, aliphatic hydrocarbons, alcohols, esters, ketones, amides, nitridles, sulfur-containing compounds and water, as well as cyclic and non-cyclic, aromatic and non-aromatic amines.

More specifically, the constraint steric hindrance ligand having a pKa of at least 15 which is the central feature to the metal complexes of this invention may be a derivative, wherein one or more hydrogen atoms is substituted with a group providing constraint steric hindrance, of a non-ionic prophosphatrane superbase or a N-heterocyclic carbene selected from the group consisting of imidazol-2-ylidene, dihydroimidazol-2-ylidene, oxazol-2-ylidene, triazol-5-ylidene, thiazol-2-ylidene, bis(imidazoline-2-ylidene), bis(imidazolidine-2-ylidene), pyrrolylidene, pyrazolylidene, dihydropyrrolylidene, pyrrolylidinylidene and benzo-fused derivatives thereof. The required pKa of a candidate ligand for the present invention may be either checked from a textbook or library of pKa's or, if not readily available in such literature, may easily be determined under standard conditions (e.g. room temperature) by methods well known to those skilled in the art.

The present invention further provides a method for making a five-coordinate metal complex as disclosed previously, comprising the step of making a five-coordinate monometallic complex by reacting (i) a four-coordinate monometallic complex comprising a multidentate ligand and one or more other ligands, wherein at least one of said other ligands is a constraint steric hindrance ligand having a pKa of at least about 15 with (ii) a reactant selected from the group consisting of alkynyl compounds, diazo compounds and dialkynyl compounds, the said reactant being able to afford a carbene ligand for the metal. The present invention also provides another method for making a five-coordinate metal complex, comprising:

the first step of making a five-coordinate monometallic complex comprising a carbene ligand by reacting (i) a four-coordinate monometallic complex comprising a multidentate ligand and one or more other ligands other than constraint steric hindrance ligands having a pKa of at least about 15 and other than carbene ligands with (ii) a reactant selected from the group consisting of alkynyl compounds, diazo compounds and dialkynyl compounds, the said reactant being able to afford a carbene ligand for the metal, and then the second step of reacting the five-coordinate monometallic complex obtained in the first step with a species containing a constraint steric hindrance group having a pKa of at least about 15 under conditions permitting said constraint steric hindrance group having a pKa of at least about 15 to coordinate with the metal in place of one of the other ligands other than the carbene ligand.

Both methods are applicable to all metal complexes of the invention, irrespective of whether they are mono- or bimetallic.

When the five-coordinate metal complex of the invention is a bimetallic complex wherein one metal is penta-coordinated and the other metal is tetra-coordinated, then each of the above methods preferably further comprises the step of reacting the five-coordinate monometallic complex previously made with a bimetallic complex wherein each metal is tetra-coordinated. Such reactive tetra-coordinated bimetallic complex may be for instance a dimeric structure such as [RuCl$_2$(p-cumene)]$_2$ or analogues thereof. Alternatively, the reactive tetra-coordinated bimetallic complex may be formed in situ by bringing into contact terpenene with a trichloride of ruthenium, rhodium or cobalt. The metal of said reactive tetra-coordinated bimetallic complex may be the same as or may be different from the metal of said five-coordinate monometallic complex.

In all of the above methods, each metal is independently selected from the group consisting of groups 4, 5, 6, 7, 8, 9, 10, 11 and 12 of the Periodic Table.

In a specific embodiment, the four-coordinate monometallic complex used in the first step of the above general methods includes one anionic ligand in order to provide a five-coordinate monometallic complex comprising one anionic ligand, and said methods further comprise the step of abstracting said anionic ligand from said five-coordinate monometallic complex by reacting said five-coordinate monometallic complex with a salt in the presence of a solvent so as to produce a five-coordinate monometallic complex being a cationic species associated with an anion and wherein the metal is coordinated with said solvent.

In another embodiment, this invention provides a four-coordinate monometallic complex comprising a multidentate ligand and one or more other ligands, wherein at least one of said other ligands is a constraint steric hindrance ligand having a pKa of at least about 15. Such a four-coordinate monometallic complex was unexpectedly found useful not only as an intermediate for making a catalytic component such as described herein, but also as being itself catalytically active in metathesis reactions such as ROMP, as well as in reactions involving the transfer of an atom or group to an ethyienically or acetylenically unsaturated compound or another reactive substrate, such as ATRP, ATRA and vinylation reactions, cyclopropanation of ethylenically unsaturated compounds, epoxidation, oxidative cyclisation, aziridination, cyclopropenation of alkynes, Diels-Alder reactions, Michael addition, aldol condensation of ketones or aldehydes, Robinson annelation, hydroboration, hydrosilylation, hydrocyanation of olefins and alkynes, allylic alkylation, Grignard cross-coupling, oxidation of organic compounds (including saturated hydrocarbons, sulfides, selenides, phosphines and aldehydes), hydroamidation, isomerization of alcohols into aldehydes, aminolysis of olefins, hydroxylation of olefins, hydride reduction, Heck reactions, and hydrogenation of olefins or ketones.

More specifically, the invention provides a five-coordinate metal complex, being selected from metal complexes having one of the general formulae (IA) and (IB) referred to in FIG. 3, wherein:

M is a metal selected from the group consisting of groups 4, 5, 6, 7, 8, 9, 10, 11 and 12 of the Periodic Table, preferably a metal selected from ruthenium, osmium, iron, molybdenum, tungsten, titanium, rhenium, technetium, lanthanum, copper, chromium, manganese, rhodium, vanadium, zinc, gold, silver, nickel and cobalt;

Z is selected from the group consisting of oxygen, sulphur, selenium, NR'''', PR'''', AsR'''' and SbR'''';

R'', R''' and R'''' are each a radical independently selected from the group consisting of hydrogen, $C_{1-6}$ alkyl, $C_{3-10}$ cycloalkyl, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, aryl and heteroaryl, or R'' and R''' together form an aryl or heteroaryl radical, each said radical (when different from hydrogen) being optionally substituted with one or more, preferably 1 to 3, substituents $R_5$ each independently selected from the group consisting of halogen atoms, $C_{1-6}$ alkyl, $C_{1-6}$ alkoxy, aryl, alkylsulfonate, arylsulfonate, alkylphosphonate, arylphosphonate, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, alkylammonium and arylammonium;

R' is either as defined for R'', R''' and R'''' when included in a compound having the general formula (IA) or, when included in a compound having the general formula (IB), is selected from the group consisting of $C_{1-6}$ alkylene and $C_{3-10}$ cycloalkylene, the said alkylene or cycloalkylene group being optionally substituted with one or more substituents $R_5$;

$R_1$ is a constraint steric hindrance group having a pKa of at least about 15;

$R_2$ is an anionic ligand;

$R_3$ and $R_4$ are each hydrogen or a radical selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium and arylammonium;

R' and one of $R_3$ and $R_4$ may be bonded to each other to form a bidentate ligand;

R''' and R'''' may be bonded to each other to form an aliphatic ring system including a heteroatom selected from the group consisting of nitrogen, phosphorous, arsenic and antimony;

$R_3$ and $R_4$ together may form a fused aromatic ring system, and y represents the number of $sp_2$ carbon atoms between M and the carbon atom bearing $R_3$ and $R_4$ and is an integer from 0 to 3 inclusive, salts, solvates and enantiomers thereof.

In the above definition of the compounds of the invention, the group $R_1$ is only limited by its capacity to provide constraint steric hindrance and by the value of its pKa, the latter being defined and measured as is conventional in the art, i.e. preferably under standard conditions (room temperature). Suitable but non-limiting examples of such $R_1$ groups include derivatives of the following high pKa groups wherein one or more hydrogen atoms is substituted with a group providing constraint steric hindrance:

imidazol-2-ylidene (pKa=24),
dihydroimidazol-2-ylidene (pKa higher than 24),
oxazol-2-ylidene,
triazol-5-ylidene,
thiazol-2-ylidene,
pyrrolylidene (pKa=17.5),
pyrazolylidene,
dihydropyrrolylidene,
pyrrolylidinylidene (pKa=44),
bis(imidazoline-2-ylidene) and bis(imidazolidine-2-ylidene),
benzo-fused derivatives such as indolylidene (pKa=16), and
non-ionic prophosphatrane superbases, namely as described in U.S. Pat. No. 5,698,737, preferably trimethyltriazaprophosphatrane $P(CH_3NCH_2CH_2)_3N$ known as Verkade superbase.

The constraint steric hindrance group may be for instance, but is not limited to, a branched or substituted R' group, e.g. a ter-butyl group, a substituted $C_{3-10}$ cycloalkyl group, an aryl group having two or more $C_{1-6}$ alkyl substituents (such as 2,4,6-trimethylphenyl(mesityl), 2,6-dimethylphenyl, 2,4,6-triisopropylphenyl or 2,6-diisopropylphenyl), or a heteroaryl group (such as pyridinyl) having two or more $C_{1-6}$ alkyl substituents.

In the above definition of the compounds of the invention, the group $R_2$ is an anionic ligand preferably selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium, arylammonium, halogen (preferably chlorine) and cyano.

The carbene ligand of the compounds of the invention will now be detailed herein. First it is important to note that, opposite to the Schiff base derivatives of the prior art, from 1 to 3 $sp_2$ carbon atoms may be present between the metal M and the carbon atom bearing the $R_3$ and $R_4$ groups, the synthetic route for each such species of compounds being different as explained in the following part of specifi-cation devoted to their processes of manufacture. That is, unsaturated carbon chains such as an allenylidene or cumulenylidene (e.g. buta-1,2,3-trienylidene, penta-1,2,3,4-tetraenyl-idene and the like) may be present in the said carbene ligand. Because of the simplicity of its manufacturing route, a preferred embodiment consists of a carbene ligand wherein y=2. However, methods to produce compounds with carbene ligands wherein y=1 or y=3 will also be provided. Alike in the Schiff base derivatives of the prior art, y may also be 0. A first preferred embodiment consists of each of $R_3$ and $R_4$ being a phenyl group. In a second preferred embodiment, $R_3$ and $R_4$ together form a fused aromatic ring system having the formula (VI) shown in FIG. 3. The carbene ligand in the five-coordinate metal complex of the invention may be a benzylidene ligand, a vinylidene ligand, an indenylidene ligand or a phenylindenylidene ligand.

In the above definition of the compounds of the invention having general formula (IA), the group R' is preferably selected from methyl, phenyl and substituted phenyl (e.g. dimethylbromophenyl or diisopropylphenyl). In the compounds of the invention having the general formula (IB), the group R' is preferably methylene or benzylidene.

In a more specific embodiment of the invention, especially when the above compounds are intended for use in an olefin metathesis reaction, M is preferably selected from the group consisting of ruthenium, osmium, iron, molybdenum, tungsten, titanium and rhenium.

Figure 4:
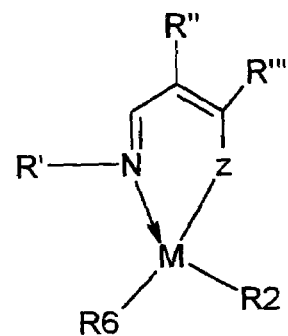
FIG. 4 shows the general chemical formulae (IIA), (IIB), (IIIA) and (IIIB) of monometallic intermediate complexes, and the general chemical formulae (IC) and (ID) of other monometallic complexes of the invention.
Figure 4:
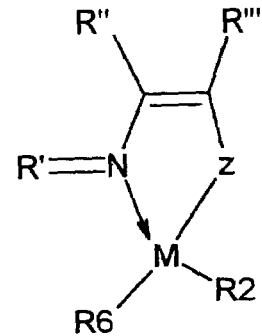
Figure 4:
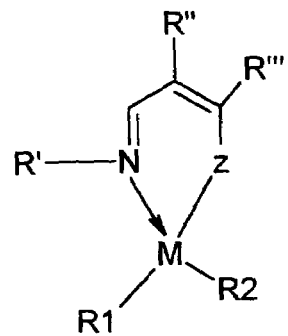
Figure 4:
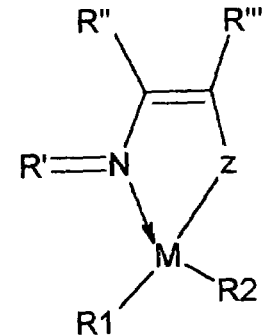
Figure 4:
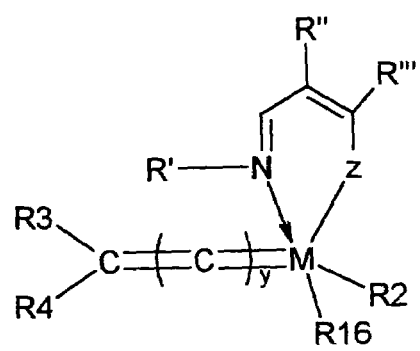
Figure 4:
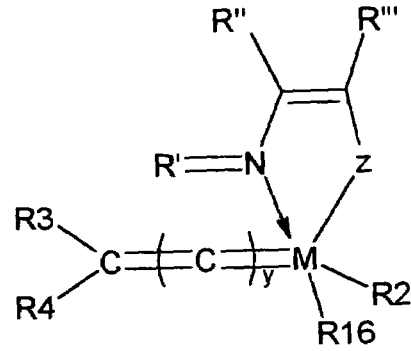

The present invention also provides a first method for making a fve-coordinate metal complex having one of the general formulae (IA) and (IB), comprising reacting a four-coordinate metal complex having one of the general formulae (IIA) and (IIB) wherein M, Z, R, R', R", R''', R'''' and $R_2$ are as previously defined with respect to the general formulae (IA) and (IB), and $R_6$ is a leaving group, with a compound having the formula $R_1Y$ wherein $R_1$ is also as previously defined and Y is a leaving group, thus resulting in an intermediate having the formula (IIIA) or (IIIB) referred to in FIG. 4, and further reacting the said intermediate with a reactant selected from the group consisting of:

an alkynyl compound having the formula $R_3R_4R_7CC\equiv CH$ wherein $R_3$ and $R_4$ are as previously defined for the compounds having the general formulae (IA) and (IB) respectively, and $R_7$ is selected from the group consisting of hydrogen, hydroxyl and $R_3$ (when y=2), a diazo compound having the formula $N_2CR_3R_4$ wherein $R_3$ and $R_4$ are as previously defined (when y is 0), an alkynyl compound having the formula $R_3C\equiv CH$ wherein $R_3$ is as previously defined (when y is 1), and a dialkynyl compound having the formula $R_{21}C\equiv C-C\equiv CR_{22}$ wherein $R_{21}$ and $R_{22}$ are each independently selected from hydrogen and trialkylsilyl (when y is 3).

For performing the above method, the leaving group Y is as commonly defined in the art (for instance, see Organic Chemistry, Structure and Function (1999), $3^{rd}$ ed., W.H.Freeman & Co., New-York, pages 216-217 and 227), and is preferably selected from the group consisting of hydrogen, $C_{1-6}$ alkoxy (e.g. tert-butoxy), $PR_3$ and $NR_3$, wherein $R_3$ is as previously defined. As indicated herein-above, the reactant used in the second step of the method differs from one species to the other, depending upon the value of y. For instance, when y is 2, a suitable alkylnyl compound is one wherein each of $R_3$ and $R_4$ is a phenyl group and $R_7$ is hydroxy. When y is 3, a suitable dialkylnyl compound is butadiyne or trimethylsilylbutadiyne.

The present invention also provides a second method for making making a five-coordinate metal complex having one of the general formulae (IA) and (IB), comprising in a first step reacting a compound having the general formula (IIA) or (IIB) referred to in FIG. 4, wherein M, Z, R, R', R", R''', R'''' and $R_2$ are as previously defined with respect to formulae (IA) and (IB) respectively, and $R_6$ is a leaving group, with a reactant selected from the group consisting of:

an alkynyl compound having the formula $R_3R_4R_7CC\equiv CH$ wherein $R_3$ and $R_4$ are as previously defined for the compounds having the general formulae (IA) and (IB) respectively, and $R_7$ is selected from the group consisting of hydrogen, hydroxyl and $R_3$ (when y=2), a diazo compound having the formula $N_2CR_3R_4$ wherein $R_3$ and $R_4$ are as previously defined (when y is 0), an alkynyl compound having the formula $R_3C\equiv CH$ wherein $R_3$ is as previously defined (when y is 1), and a dialkynyl compound having the formula $R_{21}C\equiv C-C\equiv C R_{22}$ wherein $R_{21}$ and $R_{22}$ are each independently selected from hydrogen and trialkylsilyl (when y is 3), and in a second step further reacting the reaction product of the first step with a compound having the formula $R_1Y$ wherein $R_1$ is as previously defined and Y is a leaving group. In this second method, suitable examples of the leaving group Y are as disclosed for the first method.

In the above methods, $R_6$ is preferably a group selected from aromatic and unsaturated cycloaliphatic (such as but not limited to cyclooctadienyl, norbomadienyl, cyclopentadienyl and cyclooctatrienyl) groups, the said group being optionally substituted with one or more $C_{1-6}$ alkyl groups. A suitable example of such a group is methylisopropylphenyl, the methyl and isopropyl substituents of the phenyl group being preferably in para positions.

The present invention also provides a four-coordinate metal complex having one of the general formulae (IIIA) and (IIIB) referred to in FIG. 4, wherein:

M is a metal selected from the group consisting of groups 4, 5, 6, 7, 8, 9, 10, 11 and 12 of the Periodic Table, preferably a metal selected from ruthenium, osmium, iron, molybdenum, tungsten, titanium, rhenium, technetium, lanthanum, copper, chromium, manganese, rhodium, vanadium, zinc, gold, silver, cobalt and nickel;

Z is selected from the group consisting of oxygen, sulphur, selenium, NR"", PR"", AsR"" and SbR"";

R", R''' and R"" are each a radical independently selected from the group consisting of hydrogen, $C_{1-6}$ alkyl, $C_{3-8}$ cycloalkyl, aryl and heteroaryl, or R" and R''' together form an aryl or heteroaryl radical, each said radical being optionally substituted with one or more, preferably 1 to 3, substituents $R_5$ each independently selected from the group consisting of halogen atoms, $C_{1-6}$ alkyl, $C_{1-6}$ alkoxy, aryl, alkylsulfonate, arylsulfonate, alkylphosphonate, arylphosphonate, alkylammonium and arylammonium;

R' is either as defined for R", R''' and R"" when included in a compound having the general formula (IIIA) or, when included in a compound having the general formula (IIIB), is selected from the group consisting of $C_{1-6}$ alkylene and $C_{3-8}$ cycloalkylene, the said alkylene and cycloalkylene group being optionally substituted with one or more substituents $R_5$;

$R_1$ is a constraint steric hindrance group having a $pK_a$ of at least about 15; and $R_2$ is an anionic ligand, a salt, a solvate or an enantiomer thereof.

The invention also provides a four-coordinate metal complex having one of the general formulae (IIA) and (IIB) referred to in FIG. 4, wherein:

M is a metal selected from the group consisting of groups 4, 5, 6, 7, 8, 9, 10, 11 and 12 of the Periodic Table, preferably a metal selected from ruthenium, osmium, iron, molybdenum, tungsten, titanium, rhenium, technetium, lanthanum, copper, chromium, manganese, rhodium, vanadium, zinc, gold, silver, cobalt and nickel;

Z is selected from the group consisting of oxygen, sulphur, selenium, NR"", PR"", AsR"" and SbR"";

R", R''' and R"" are each a radical independently selected from the group consisting of hydrogen, $C_{1-6}$ alkyl, $C_{3-10}$ cycloalkyl, aryl and heteroaryl, or R" and R''' together form an aryl or heteroaryl radical, each said radical being optionally substituted with one or more, preferably 1 to 3, substituents $R_5$ each independently selected from the group consisting of halogen atoms, $C_{1-6}$ alkyl, $C_{1-6}$ alkoxy, aryl, alkylsulfonate, arylsulfonate, alkylphosphonate, arylphosphonate, alkylammonium and arylammonium, or R" and R'" together form an aryl or heteroaryl radical, the said radical being substituted with either one substituent $R_5$ selected from the group consisting of bromine, iodine, $C_{2-6}$ alkyl, $C_{2-6}$ alkoxy, aryl, alkylsulfonate, arylsulfonate, alkylphosphonate, arylphosphonate, alkylammonium and arylammonium, or two or more substituents $R_5$ each independently selected from the group consisting of halogen atoms, $C_{1-6}$ alkyl, $C_{1-6}$ alkoxy, aryl, alkylsulfonate, arylsulfonate, alkylphosphonate, arylphosphonate, alkylammonium and arylammonium;

R' is either as defined for R", R'" and R"" when included in a compound having the general formula (IIA) or, when included in a compound having the general formula (IIB), is selected from the group consisting of $C_{1-6}$ alkylene and $C_{3-10}$ cycloalkylene, the said $C_{1-6}$ alkylene or $C_{3-10}$ cycloalkylene group being optionally substituted with one or more substituents $R_5$;

$R_2$ is an anionic ligand; and $R_6$ is a group selected from aromatic and unsaturated cycloaliphatic, preferably aryl and $C_{4-20}$ cycloalkenyl (such as cyclooctadienyl, norbornadienyl, cyclopentadienyl and cyclooctatrienyl) groups, the said group being optionally substituted with one or more $C_{1-6}$ alkyl groups, a salt, a solvate or an enantiomer thereof.

More specific definitions of $R_1$ and $R_2$ for the above classes of intermediate compounds were already given for the compounds having the general formulae (IA) and (IB) respectively. All such compounds having the general formulae (IIA), (IIB), (IIIA) and (IIIB) are useful as intermediates for making compounds having one of the general formulae (IA) and (IB).

Intermediates having the formula (IIA) may be prepared by analogy to a well known method comprising first condensing an hydroxy-aldehyde having the general formula:

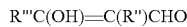
R'"C(OH)=C(R")CHO such as salicylaldehyde (when Z is oxygen) or a corresponding thio-aldehyde (when Z is sulfur), amino-aldehyde (when Z is NR""), phosphino-aldehyde (when Z is PR""), arsino-aldehyde (when Z is AsR"") or stibino-aldehyde (when Z is SbR"") wherein the hydroxy, thio, amino, phosphino, arsino or stibino group is in a β position with respect to the aldehyde group, with a primary aliphatic or aromatic amine, then converting the resulting aldimine into a salt thereof by means of a reaction with e.g. an alkoxide of a metal of any of groups IA, IIA or IIIA of the Periodic Classification of Elements (e.g. sodium, potassium, magnesium or thallium) and then reacting the said salt with a metal complex having a labile ligand (e.g. halogen) such as for instance [RuCl$_2$(p-cumene)]$_2$. The second class of intermediates having the formula (IIB) may be prepared, in order to yield the desired five-member chelate ligand, by first condensing an aldehyde such as benzaldehyde with an amino-alcohol such as o-hydroxyaniline (when Z is oxygen), an amino-thiol (when Z is sulfur), a diamine (when Z is NR""), an aminophosphine (when Z is PR""), an aminoarsine (when Z is AsR"") or an aminostibine (when Z is SbR"") wherein the hydroxy, thio, secondary amino, phosphino, arsino or stibino group is in a p position with respect to the primary amino group, then converting the resulting aldimine into a salt thereof and then reacting the said salt with a metal complex having a labile ligand in a manner similar to that indicated for compound (IIA) above.

The present invention also provides a supported catalyst for use in a heterogeneous catalytic reaction, comprising:
  (a) a catalytically active five-coordinate metal complex such as previously described, and
  (b) a supporting amount of a carrier suitable for supporting said catalytically active five-coordinate metal complex (a).

In such a supported catalyst, said carrier may be selected from the group consisting of porous (i.e. both microporous and mesoporous) inorganic solids (including, but not limited to, alumina, silica, zirconia and alumino-silica), such as amorphous or paracrystalline materials, crystalline molecular sieves and modified layered materials including one or more inorganic oxides, and organic polymer resins such as polystyrene resins and derivatives thereof (including, among others, copolymers of styrene and divinylbenzene).

Porous inorganic solids that may be used with the catalysts of the invention have an open microstructure and/or mesostructure that allows molecules access to the relatively large surface areas of these materials that enhance their catalytic and sorptive activity. These porous materials can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in the catalytic and sorptive behavior of the materials, as well as in differences in various observable properties used to characterize them, such as their surface area, the sizes of pores and the variability in those sizes, the presence or absence of X-ray diffraction patterns and the details in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent". The microstructure of the silicas consists of 100-250 Angstrom particles of dense amorphous silica (Kirk-Othmer Encyclopedia of Chemical Technology, 3rd. ed., vol. 20, 766-781 (1982)), with the porosity resulting from voids between the particles.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions (K. Wefers and Chanakya Misra, "Oxides and Hydroxides of Aluminum", Technical Paper No 19 Revised, Alcoa Research Laboratories, 54-59 (1987)). Since, in the case of either material, there is no long range order controlling the sizes of pores in the material, the variability in pore size is typically quite high. The sizes of pores in these materials fall into a regime called the mesoporous range,; including, for example, pores within the range of about 15 to 200 Angstroms.

In sharp contrast to these structurally ill-defined solids are materials whose pore size distribution is very narrow because it is controlled by the precisely repeating crystalline nature of the material microstructure. These materials are called "molecular sieves", the most important examples thereof being zeolites. Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials are known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of SiO4 and Periodic Table Group IIIB element oxide, e.g., AlO4, in which the tetrahedra are cross-linked by the sharing of oxygen atoms whereby the ratio of the total Group IIIB element, e.g., aluminum, and Group IVB element e.g., silicon, atoms to oxygen atoms is 1:2. The electrovalence of the tetrahedra containing the Group IIIB element, e.g., aluminum, is balanced by the inclusion in the crystal of a cation, for example, an alkali metal or an alkaline earth metal cation. This can be expressed wherein the ratio of the Group IIIB element, e.g., aluminum, to the number of various cations, such as Ca, Sr, Na, K or Li, is equal to 1. One type of cation may be exchanged either entirely or partially with another type of cation utilizing ion exchange techniques in a conventional manner. By means of such cation exchange, it has been possible to vary the properties of a given silicate by suitable selection of the cation. Many of these zeolites have come to be designated by letter or other convenient symbols, as illustrated by zeolites A (U.S. Pat. No. 2,882,243); X (U.S. Pat. No. 2,882,244); Y (U.S. Pat. No. 3,130,007); ZK-5 (U.S. Pat. No. 3,247,195); ZK-4 (U.S. Pat. No. 3,314,752); ZSM-5 (U.S. Pat. No. 3,702,886); ZSM-11 (U.S. Pat. No. 3,709,979); ZSM-12 (U.S. Pat. No. 3,832,449), ZSM-20 (U.S. Pat. No. 3,972,983); ZSM-35 (U.S. Pat. No. 4,016,245); ZSM-23 (U.S. Pat. No. 4,076,842); MCM-22 (U.S. Pat. No. 4,954,325); MCM-35 (U.S. Pat. No. 4,981,663); MCM-49 (U.S. Pat. No. 5,236,575); and PSH-3 (U.S. Pat. No. 4,439,409). The latter refers to a crystalline molecular sieve composition of matter named PSH-3 and its synthesis from a reaction mixture containing hexamethyleneimine, an organic compound which acts as directing agent for synthesis of a layered MCM-56. A similar composition, but with additional structural components, is taught in EP-A 293,032. Hexamethyleneimine is also taught for use in synthesis of the crystalline molecular sieve ZSM-12 in U.S. Pat. No. 5,021,141. A molecular sieve composition SSZ-25 is taught in U.S. Pat. No. 4,826,667 and EP-A 231,860, said zeolite being synthesized from a reaction mixture containing an adamantane quaternary ammonium ion. Molecular sieve material being selected from the group consisting of zeolites REY, USY, REUSY, dealuminated Y, ultrahydrophobic Y, silicon-enriched dealuminated Y, ZSM-20, Beta, L, silicoaluminophosphates SAPO-5, SAPO-37, SAPO-40, MCM-9, metalloaluminophosphate MAPO-36, aluminophosphate VPI-5 and mesoporous crystalline MCM-41 are also suitable for including into a supported catalyst of this invention.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include layered silicates, magadiite, kenyaite, tri-titanates and perovskites. Another example of a non-water swellable layered material, which can be swollen with certain organic swelling agents, is a vacancy-containing titanometallate material, as described in U.S. Pat. No. 4,831,006. Once a layered material is swollen, the material may be pillared by interposing a thermally stable substance, such as silica, between the spaced apart layers. The aforementioned U.S. Pat. Nos. 4,831,006 and 4,859,648 describe methods for pillaring the non-water swellable layered materials described therein and are incorporated herein by reference for definition of pillaring and pillared materials. Other patents teaching pillaring of layered materials and the resulting pillared products include, but are not limited to, U.S. Pat. Nos. 4,216,188; 4,248,739; 4,176,090; and 4,367,163; and EP-A-205,711. The X-ray diffraction patterns of pillared layered materials can vary considerably, depending on the degree that swelling and pillaring disrupt the otherwise usually well-ordered layered microstructure. The regularity of the micro-structure in some pillared layered materials is so badly disrupted that only one peak in the low angle region on the X-ray diffraction pattern is observed, at a d-spacing corresponding to the interlayer repeat in the pillared material. Less disrupted materials may show several peaks in this region that are generally orders of this fundamental repeat. X-ray reflections from the crystalline structure of the layers are also sometimes observed. The pore size distribution in these pillared layered materials is narrower than those in amorphous and paracrystalline materials but broader than that in crystalline framework materials.

Other porous inorganic solids that may be used with the catalysts of the invention include recently disclosed mesoporous materials such as DAM-1 (see U.S. Pat. No. 6,630,170 disclosing a mesoporous composition prepared from a mixture comprising hydrochloric acid, vitamin E and a silica source, wherein said vitamin E functions as a templating molecule, and said mesoporous composition exhibits uniform pore size), SBA-1, -2 and 3 (such as reported in *Science* (1995) 268:1324) and SBA-15 (U.S. Pat. No. 6,592,764) as well as in other literature such as U.S. Pat. No. 6,669,924, the content of which is incorporated herein by reference.

The present invention also provides the use of a five-coordinate metal complex within the broad acceptation described herein above or more particularly having one of the general formulae (IA) and (IB), preferably one wherein the metal M is selected from the group consisting of ruthenium, osmium, iron, molybdenum, tungsten, titanium, technetium, lanthanum and rhenium, or a supported catalyst including a carrier such as previously defined, as a catalytic component in a reaction selected from the group consisting of metathesis reactions, reactions involving the transfer of an atom or group to an ethylenically or acetylenically unsaturated compound or another reactive substrate, such as atom transfer radical reactions, addition polymerisation reactions, vinylation reactions, cyclopropanation of ethylenically unsaturated compounds, epoxidation, oxidative cyclisation, aziridination, cyclopropenation of alkynes, Diels-Alder reactions, Michael addition, aldol condensation of ketones or aldehydes, Robinson annelation, hydroboration, hydrosilylation, hydrocyanation of olefins and alkynes, allylic alkylation, Grignard cross-coupling, oxidation of organic compounds (including saturated hydrocarbons, sulfides, selenides, phosphines and aldehydes), hydroamidation, isomerization of alcohols into aldehydes, aminolysis of olefins, hydroxylation of olefins, hydride reduction, Heck reactions, and hydrogenation of olefins or ketones.

Since the five-coordinate metal complex of this invention is usually obtained as a solid, for most of the above-listed uses of said complex it will be preferable to dissolve or suspend the five-coordinate metal complex in a suitable solvent such as disclosed hereinafter.

In a first embodiment, said reaction is a metathesis reaction for transforming a first olefin into at least one second olefin (being different from the said first olefin) or into a linear olefin oligomer or polymer or else into a cyclo-olefin. The invention thus relates to a method for performing a metathesis reaction comprising contacting at least one first olefin with a catalytically active metal carbene compound having one of the general formulae (IA) and (IB), optionally supported on a suitable carrier. The high level metathesis activity of the metal carbene compounds of the present invention causes these compounds to coordinate with and catalyze metathesis reactions between all types of olefins. Examplary reactions enabled by the metal carbene complexes of the present invention include, but are not limited to, ring-opening metathesis polymerization (ROMP) of preferably strained cyclic olefins, ring closing metathesis (RCM) of acyclic dienes, cross metathesis reactions involving at least one acyclic or cyclic olefin and de-polymerization of olefinic polymers. In particular, the catalysts of the present invention are able to catalyze unsubstituted, monosubstituted and disubstituted strained mono-, bi- and polycyclic olefins with a ring size of at least three, preferably 3 to 5, atoms. Examples of cyclic olefins that may be used in such metathesis reactions include norbornene and functional derivatives thereof (such as illustrated in the following examples), cyclobutene, norbornadiene, cyclopentene, dicyclopentadiene, cycloheptene, cyclooctene, 7-oxanorbornene, 7-oxanorbornadiene, cyclooctadiene, cyclododecene and mono- and disubstituted derivatives thereof, especially derivatives wherein the substituent may be $C_{1-7}$ alkyl, cyano, diphenylphosphine, trimethylsilyl, methylaminomethyl, carboxylic acid or ester, trifluoromethyl, maleic ester, maleimido and the like, such as disclosed in U.S. Pat. No. 6,235,856, the content of which is incorporated herein in its entirety. The invention also contemplates ROMP of mixtures of two or more such monomers in any proportions. Further examples include water-soluble cyclic olefins such as exo-N-(N',N',N'-trimethylammonio)ethyl-bicyclo [2.2.1]hept-5-ene-2,3-dicarbox-imide chloride or exo-N-(N', N',N'-trimethylammonio)ethyl-bicyclo-7-oxabicyclo[2.2.1] hept-5-ene-2,3-dicarboximide chloride. As is well known to the skilled person, cyclic olefins such as cyclohexenes which have little or no ring strain cannot be polymerized because there is no thermodynamic preference for polymer versus monomer.

The metathesis (e.g. polymerisation) reaction of the invention may be carried out in a preferably substantially inert atmosphere, either in bulk (i.e. in the absence of any solvent) or in the presence of one or more solvents. For instance this reaction may be performed by dissolving a catalytic amount of the metal carbene catalyst of the invention in one or more solvents and by adding one or more olefins, e.g. (ROMP) one or more strained cyclic olefins, the latter being optionally dissolved in the same or another solvent, to the metal carbene catalyst solution, preferably under agitation. The need for an olefin solvent, and the amount of solvent to be used, will depend upon the physical state of said olefin, as is well known in the art. For instance a solvent will certainly be required when the olefin is a solid, such as dicyclopentadiene, at the reaction temperature. Solvents that may be used for performing the metathesis reaction of this invention include all kinds of inert organic solvents such as protic solvents, polar aprotic solvents and non-polar solvents as well as aqueous solvents which are inert under the (polymerization) conditions used. More specific examples of suitable organic solvents include ethers (e.g. dibutyl ether, tetrahydrofuran, dioxane, ethylene glycol monomethyl or dimethyl ether, ethylene glycol monoethyl or diethyl ether, diethylene glycol diethyl ether or triethylene glycol dimethyl ether), halogenated hydrocarbons (e.g. methylene chloride, chloroform, 1,2-dichloroethane, 1,1,1-trichloroethane or 1,1,2,2-tetrachloroethane), carboxylic acid esters and lactones (e.g. ethyl acetate, methyl propionate, ethyl benzoate, 2-methoxyethyl acetate, γ-butyrolactone, δ-valerolactone or pivalolactone), carboxylic acid amides and lactams (e.g. N,N-dimethylformamide, N,N-diethylformamide, N,N-dimethylacetamide, tetramethylurea, hexamethyl-phosphoric acid triamide, γ-butyrolactam, ε-caprolactam, N-methylpyrrolidone, N-acetylpyrrolidone or N-methylcaprolactam), sulfoxides (e.g. dimethyl sulfoxide), sulfones (e.g. dimethyl sulfone, diethyl sulfone, trimethylene sulfone or tetramethylene sulfone), aliphatic and aromatic hydrocarbons (e.g. petroleum ether, pentane, hexane, cyclohexane, methylcyclohexane, benzene, chlorobenzene, o-dichlorobenzene, 1,2,4-trichlorobenzene, nitrobenzene, toluene or xylene), and nitriles (e.g. acetonitrile, propionitrile, benzonitrile or phenylacetonitrile).

When water or an aqueous mixture is selected as the solvent, it is preferable to use a cationic metal complex species as the catalytic component, the said cationic species being associated with an anion A as described hereinabove.

The solubility of the polymer formed during the metathesis polymerization reaction will depend upon the choice of solvent and the molecular weight and concentration of the polymer obtained. When the strained cyclic olefin is polyunsaturated (e.g. dicyclopentadiene or norbornadiene), the polymer obtained may often be insoluble, whatever the solvent used. Reaction temperatures can range typically from about 0° C. to about 120° C., preferably from about 20° C. to 85° C. The duration of the reaction may be at least about 1 minute, preferably at least 5 minutes, and more preferably at least 30 minutes; the duration of polymerisation may be at most about 24 hours (although longer times may be used at the expense of economic conditions), preferably at most about 600 minutes. The molar ratio of the strained cyclic olefin to the catalytic component of the invention is not critical and, depending upon the olefin to be polymerised, may be at least about 100, preferably at least 250, more preferably at least 500. The said molar ratio is usually at most about 1,000,000, preferably at most 300,000 and more preferably at most 50,000. Before the polymer formed solidifies or, at will, when a desired molecular weight of the polymer has been achieved (as may be controlled for instance by monitoring reactor temperature and/or reaction mixture viscosity), an oxidation inhibitor and/or a terminating (or chain-transfer) agent may be added to the reaction mixture, if need be. The choice of the terminating or chain-transfer agent used is not critical to this invention, provided that the said terminating agent reacts with the catalytic component, e.g. the carbene metal compound (IA) or (IB), and produces another species, e.g. another carbene metal compound which is substantially inactive or significantly less active, i.e. is not able to further propagate the reaction, under the prevailing temperature conditions. Suitable examples of such terminating agents include, but are not limited to, vinylic compounds such as phenyl vinyl sulfide, ethyl vinyl ether, vinyl acetate and N-vinylpyrrolidone. Also, for instance, adding a molar excess (with respect to the catalytic component) of a carbonyl compound to the reaction mixture is able to produced a metal oxo and an olefin (or polymer) capped with the former carbonyl functionality; the cleaved polymer can then be separated from the catalyst by precipitation with methanol. Another way of cleaving the polymer from the catalyst may be by the addition of a vinylalkylether. Alternatively, reaction with several equivalents of a chain-transfer agent such as a diene is another way of cleaving the polymer chain, which method does not deactivate the catalytic component, permitting additional monomer to be polymerised, however possibly at the risk of broadening molecular weight distribution.

Because the five-coordinate metal complexes, in particular as represented by the general formulae (IA) and (IB), of this invention are stable in the presence of various functional groups, they may be used to catalyze a wide variety of olefins under a wide variety of process conditions. In particular the first olefinic compound to be converted by a metathesis reaction may include one or more, preferably at most 2, functional atoms or groups being for instance selected from the group consisting of hydroxyl, thiol (mercapto), ketone, aldehyde, ester (carboxylate), thioester, cyano, cyanato, epoxy, silyl, silyloxy, silanyl, siloxazanyl, boronato, boryl, stannyl, disulfide, carbonate, imine, carboxyl, amine, amide, carboxyl, isocyanate, thioisocyanate, carbodiimide, ether (preferably $C_{1-20}$ alkoxy or aryloxy), thioether (preferably $C_{1-20}$ thioalkoxy or thioaryloxy), nitro, nitroso, halogen (preferably chloro), ammonium, phosphonate, phosphoryl, phosphino, phosphanyl, $C_{1-20}$ alkylsulfanyl, arylsulfanyl, $C_{1-20}$ alkylsulfonyl, arylsulfonyl, $C_{1-20}$ alkylsulfinyl, arylsulfinyl, sulfonamido and sulfonate (preferably paratoluenesulfonate, methanesulfonate or trifluoromethanesulfonate). The said first olefin functional atom or group may be either part of a substituting group of the first olefin or part of the carbon chain of the first olefinic compound.

The high level metathesis activity of the five-coordinate metal complexes of this invention also makes them useful for catalyzing at relatively low temperatures (about 20° C. to 80° C.), in the presence or absence of a solvent, the ring-closing metathesis of acyclic dienes such as, for instance, diallylic compounds (diallyl ether, diallyl thioether, diallyl phtalate, diallylamino compounds such as diallylamine, diallylamino phosphonates, diallyl glycine esters, etc), 1,7-octadiene, substituted 1,6-heptadienes and the like. In the case of diallylic compounds such as mentioned above, the reaction may even proceed unexpectedly further to the obtention of a pyrrolyl compound, a furanyl compound or a thiophenyl compound, i.e. a dehydrogenated product, provided that the five-coordinate metal complex being used is a bimetallic complex wherein one metal is penta-coordinated and the other metal is tetra-coordinated.

The five-coordinate metal complexes of this invention may also be used for the preparation of telechelic polymers, i.e. macromolecules with one or more reactive end-groups which are useful materials for chain extension processes, block copolymer synthesis, reaction injection moulding, and polymer network formation. An example thereof is hydroxyl-telechelic polybutadiene which may be obtained from 1,5-cycooctadiene, 1,4-diacetoxy-cis-2-butene and vinyl acetate. For most applications, a highly functionalized polymer, i.e. a polymer with at least two functional groups per chain, is required. The reaction scheme for a telechelic polymer synthesis via ring opening metathesis polymerisation is well known to those skilled in the art: in such a scheme, acyclic olefins act as chain-transfer agents in order to regulate the molecular weight of the telechelic polymer produced. When α,ω-bifunctional olefins are used as chain-transfer agents, truly bi-functional telechelic polymers can be synthesized.

As a summary, a metathesis reaction method according to the invention can be performed, wherein the first olefinic compound is an acyclic mono-olefin. For instance the said method for olefin coupling by cross-metathesis may comprise the step of contacting a first acyclic olefin or functionalized olefin, such as above-defined, with a metal carbene compound of the invention in the presence of a second olefin or functionalized olefin. More preferably, the said cross-metathesis reaction can be for transforming a mixture of a mono-olefin having the formula $R_8CH=CHR_{10}$ and a mono-olefin having the formula $R_9CH=CHR_{11}$, wherein each of $R_8$, $R_9$, $R_{10}$ and $R_{11}$ is independently selected from $C_{1-20}$ alkyl groups optionally bearing one or more functional atoms or groups such as above defined, into a mixture of a mono-olefin having the formula $R_8CH=CHR_9$ and a mono-olefin having the formula $R_{11}CH=CHR_{10}$.

Alternatively, the said first olefinic compound may be a diolefin or a cyclic mono-olefin with a ring size of at least three atoms, and the said metathesis reaction is preferably performed under conditions suitable for transforming said diolefin or cyclic mono-olefin into a linear olefin oligomer or polymer. When the said first olefinic compound is a diolefin, the said metathesis reaction may also be performed under conditions suitable for transforming said diolefin into a mixture of a cyclic mono-olefin and an aliphatic alpha-olefin.

Depending upon the selection of the starting substrates for the metathesis reaction and the intended use of the final organic molecule to be produced, the said metathesis reaction can yield a very wide range of end-products including biologically active compounds. For instance the reaction may be for transforming a mixture of two dissimilar olefins, at least one of which is an alpha-olefin, selected from (i) cyclodienes containing from 5 to 12 carbon atoms and (ii) olefins having the formula:

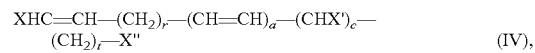

(IV), into an unsaturated biologically active compound having the formula:

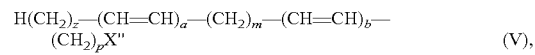

(V), wherein:
  a is an integer from 0 to 2,
  b is selected from 1 and 2,
  c is selected from 0 and 1,
  m and p are such that the hydrocarbon chain in formula (V) contains from 10 to 18 carbon atoms,
  r and t are such that the combined total of carbon atoms in the hydrocarbon chains of the two dissimilar olefins of formula (IV) is from 12 to 40,
  z is an integer from 1 to 10, and
  X, X' and X" are atoms or groups each independently selected from the group consisting of hydrogen, halogen, methyl, acetyl, —CHO and —$OR_{12}$, wherein $R_{12}$ is hydrogen or an alcohol protecting group selected from the group consisting of tetrahydropyranyl, tetrahydrofuranyl, tert-butyl, trityl, ethoxyethyl and $SiR_{13}R_{14}R_{15}$ wherein $R_{13}$, $R_{14}$ and $R_{15}$ are each independently selected from $C_{1-6}$ alkyl groups and aryl groups.

The said unsaturated biologically active compound having the formula (V) may be a pheromone or pheromone precursor, an insecticide or a insecticide precursor, a pharmaceutically active compound or a pharmaceutical intermediate, a fragrance or a fragrance precursor. A few non-limiting examples of the said unsaturated biologically active compounds include 7,11-hexadecadienyl acetates, 1-chloro-5-decene, trans,trans-8,10-dodeca-dienol, 3,8,10-dodecatrienol, 5-decenyl acetate, 11-tetradecenylacetate and 1,5,9-tetradecatriene. Gossyplure, comprising a mixture of 7,11-hexadecadienyl acetate stereoisomers, is a commercially available pheronome useful in pest control in view of its effectiveness in disrupting the mating and reproductive cycles of specifically targeted insect species. It may advantageously be produced from 1,5,9-tetradecatriene, the latter being obtainable from cyclooctadiene and 1-hexene according to the present invention.

When performing the metathesis reaction process of the invention, although in most cases the said reaction proceeds very quickly, it may be advantageous for a few specific olefins, in order to improve the reaction rate and/or yield of the metathesis reaction, to further contact the first olefinic compound, and optionally the second olefinic compound, with an organic or inorganic acid or a Lewis acid co-catalyst ($b_1$) e.g. based on aluminium, titanium or boron, the latter being well defined in the art, and/or a catalyst activator ($b_2$). For instance the Lewis acid co-catalyst ($b_1$) may be selected from the group consisting of boron trihalides; trialkylboron; triarylboron; organoaluminum compounds; magnesium halides; aluminum halides; titanium or vanadium halides, preferably titanium tetrachloride; antimony and bismuth pentahalides. For instance the Lewis acid co-catalyst ($b_1$) may be an organoaluminum compound selected from the group consisting of tri-n-alkylaluminums; dialkyl-aluminum hydrides, trialkenylaluminums, alkylaluminum alkoxides, dialkylaluminum alkoxides, dialkylaluminum aryloxides and dialkylaluminum halides. The catalyst activator ($b_2$) may be for instance a diazo compound such as, but not limited to, ethyldiazoacetate and trimethylsilyldiazomethane.

At the opposite, as illustrated by some of the following examples, ring-opening metathesis polymerization (ROMP) reactions using the catalysts of the invention may proceed in such an extremely quickly fashion for monomers such as norbornene, substituted norbornenes, dicyclopentadiene or oligomers thereof (i.e. Diels-Alder adducts formed with about 1 to 20 cyclopentadiene units) or mixtures thereof with strained monocyclic or polycyclic fused olefins (e.g. as defined in U.S. Pat. No. 6,235,856, the content of which is incorporated herein by reference) that polymerization control could become a problem in the absence of appropriate measures. This kind of problem is likely to occur during the molding of thermoset polymers wherein a liquid olefin monomer and a catalyst are mixed and poured, cast or injected into a mold and wherein on completion of polymerization (i.e. "curing" of the article) the molded part is removed from the mold before any post cure processing that may be required, such as in the Reaction Injection Molding ("RIM") technique. It is well known that the ability to control reaction rates, i.e. the pot life of the reaction mixture, becomes more important in the molding of larger parts. Using the catalysts of the invention, extending the pot life and/or controlling the rate of a metathesis polymerisation reaction may be effected in different ways, such as increasing the ratio catalyst/olefin and/or adding a polymerization retardant to the reaction mixture. Moreover this can be achieved by an improved embodiment comprising:

(a) a first step of contacting a metathesis catalyst (optionally supported) as previously disclosed with an olefin in a reactor at a first temperature at which the said metathesis catalyst is substantially unreactive (inactive), and (b) a second step of bringing the reactor temperature (e.g. heating said reactor) up to a second temperature above the said first temperature, at which said catalyst is active.

In a more specific embodiment, heat activation occurs in bursts rather than continuously, e.g. by repeating the sequence of steps (a) and (b).

Within the said controlled polymerization method, it should be understood that the non-reactivity of the catalyst in the first step depends not only on the first temperature but also on the olefin/catalyst ratio in the olefin/catalyst mixture. Preferably the first temperature is about 20° C. (i.e. room temperature) but, for specific olefins and specific olefin/catalytic component ratios, it may even be suitable to cool the olefin/catalyst mixture below room temperature, e.g. down to about 0° C. The second temperature is preferably above 40° C. and may be up to about 90° C.

As illustrated by the following examples, ring-opening metathesis polymerization reactions using the catalysts of the invention readily achieve polymers such as polynorbornene, and functional derivatives thereof, and polydicyclopentadienes with well or better controlled characteristics such as molecular weight (number average) and molecular weight distribution (polydispersity). In particular, norbornene polymers with an average molecular weight ranging from about 25,000 to about 2,000,000, in particular from about 200,000 to about 600,000 and/or with a polydispersity index ($M_w/M_n$) ranging from about 1.2 to 3.5, preferably from about 1.3 to about 2.5 may be prepared.

Ring-opening metathesis polymerization reactions using the catalysts of the invention, in particular when performed in a mold such as in the RIM technique, may occur in the presence of formulation auxiliaries, such as antistatics, antioxidants, ceramics, light stabilizers, plasticizers, dyes, pigments, fillers, reinforcing fibers, lubricants, adhesion promoters, viscosity-enhancing agents and demolding agents as is already well known in the art.

Depending upon the specific reaction involved in this aspect of this invention, and especially when the said reaction is ROMP of strained cyclic olefins, reaction may also advantageously be performed under visible light or ultra-violet light irradiation, e.g. using a source of visible light or ultra-violet light being able to deliver sufficient energy to the reaction system.

Yet another use of the metal carbene compounds of the present invention, in particular those having one of the general formulae (IA) and (IB) and wherein the metal M is preferably selected from the group consisting of ruthenium, osmium, iron, molybdenum, tungsten, titanium, technetium, lanthanum and rhenium, is as a catalyst for the radical addition reaction of a polyhalogenated alkane, e.g. $CXCl_3$ wherein X is selected from the group consisting of hydrogen, $C_{1-6}$ alkyl, phenyl and halogen, onto an olefin or diolefin (the so-called Kharasch reaction). Such a reaction is preferably performed in the presence of an organic solvent, in a molar excess of the polyhalogenated alkane, and within a temperature range between about 30° and 100° C. Suitable examples of the polyhalogenated alkane used in this embodiment of the invention are carbon tetrachloride, chloroform, trichlorophenylmethane and carbon tetrabromide. Examples of suitable olefins for this radical addition reaction include internal and cyclic olefins as well as terminal olefins having the formula RR'C=CH$_2$, wherein R and R' may be each independently selected from hydrogen, C$_{1-7}$ alkyl, phenyl and carboxylic acid or ester, e.g. vinylaromatic monomers such as styrene or vinyltoluene, α,β-ethylenically unsaturated acid esters such as C$_{1-10}$ alkyl acrylates and methacrylates, acrylonitrile and the like.

The present invention also provides the use of a five-coordinate metal complex, optionally supported on a carrier, such as previously disclosed, or a five-coordinate metal compound having one of the general formulae (I C) and (I D) referred to in FIG. 4, or a cationic species thereof (obtained by abstracting an anionic ligand) associated with a suitable solvent (such as previously described herein), optionally in combination with a supporting amount of a carrier, wherein:

M, Z, R', R", R''', R'''', R$_2$, R$_3$, R$_4$ and y are as previously defined in respect of formulae (IA) and (IB), and R$_{16}$ is a neutral electron donor, as a catalyst component of a catalytic system for reactions involving the transfer of an atom or group to an ethylenically or acetylenically unsaturated compound or another reactive substrate, such as the atom or group transfer radical polymerization (ATRP) of one or more radically (co)polymerizable monomers, ATRA, vinylation reaction, cyclopropanation of ethylenically unsaturated compounds, epoxidation, oxidative cyclisation, aziridination, cyclopropenation of alkynes, Diels-Alder reactions, Michael addition, aldol condensation of ketones or aldehydes, Robinson annelation, hydroboration, hydrosilylation, hydrocyanation of olefins and alkynes, allylic alkylation, Grignard cross-coupling, oxidation of organic compounds (including saturated hydrocarbons, sulfides, selenides, phosphines and aldehydes), hydroamidation, isomerization of alcohols into aldehydes, aminolysis of olefins, hydroxylation of olefins, hydride reduction, Heck reactions, and hydrogenation of olefins or ketones.

By contrast to the constraint steric hindrance group R$_1$ of compounds (IA) and (IB), the neutral electron donor R$_{16}$ of compounds (IC) and (ID) usually has a pK$_a$ less than about 15. Suitable examples of R$_{16}$ include phosphines of the formula PR$_{17}$R$_{18}$R$_{19}$ wherein R$_{17}$, R$_{18}$ and R$_{19}$ are each independently selected from the group consisting of C$_{1-10}$ alkyl, C$_{3-8}$ cycloalkyl and aryl, such as for instance tricyclohexylphosphine (pK$_a$=9.7), tricyclopentylphosphine, triisopropylphosphine and triphenylphosphine (pK$_a$=2.7), as well as functionalised phosphines, arsine, stilbene, arene, heteroarene, etc. Although compounds (IC) and (ID) are often less effective than the above compounds represented by the general formulae (IA) and (IB) in the catalysis of olefin metathesis reactions, they were found to be efficient in the catalysis of reactions involving the transfer of an atom or group to an ethylenically or acetylenically unsaturated compound or another reactive substrate, such as ATRP, ATRA and vinylation reactions, cyclopropanation of ethylenically unsaturated compounds, epoxidation, oxidative cyclisation, aziridination, cyclopropenation of alkynes, Diels-Alder reactions, Michael addition, aldol condensation of ketones or aldehydes, Robinson annelation, hydroboration, hydrosilylation, hydrocyanation of olefins and alkynes, allylic alkylation, Grignard cross-coupling, oxidation of organic compounds (including saturated hydrocarbons, sulfides, selenides, phosphines and aldehydes), hydroamidation, isomerization of alcohols into aldehydes, aminolysis of olefins, hydroxylation of olefins, hydride reduction, Heck reactions, and hydrogenation of olefins or ketones.

Some of the compounds having one of the general formulae (IC) and (ID), especially those wherein y is 0 and M is ruthenium or osmium, are well known to those skilled in the art, being described in U.S. Pat. No. 5,977,393 as metathesis catalysts. Compounds having one of the general formulae (IC) and (ID), wherein y is from 1 to 3 inclusive, or wherein y is 0 but M is a metal selected from the group consisting of iron, molybdenum, tungsten, titanium, rhenium, technetium, lanthanum, copper, chromium, manganese, rhodium, vanadium, zinc, gold, silver, cobalt and nickel, are not yet known in the art but can suitably be prepared by any of the methods disclosed herein as second and third embodiments of this invention, while starting from the relevant metal and simply replacing R$_1$ with R$_{16}$ in the starting materials of the relevant method step.

As already mentioned herein-above, it is critical to the success of living/controlled radical polymerisation contemplated as a seventh embodiment of the present invention to achieve rapid exchange between growing radicals present at low stationary concentrations (in a range of from about $10^{-8}$ mole/l to $10^{-6}$ mole/l) and dormant chains present at higher concentrations (typically in a range of from about $10^{-4}$ mole/l to 1 mole/l). It may therefore be desirable to match the respective amounts of the catalytic component of the invention and of the radically (co)polymerizable monomer(s) in such a way that these concentration ranges are achieved. If the concentration of growing radicals exceeds about $10^{-6}$ mole/l, there may be too many active species in the reaction, which may lead to an undesirable increase in the rate of side reactions (e.g. radical-radical quenching, radical abstraction from species other than the catalyst system, and do on). If the concentration of growing radicals is less than about $10^{-8}$ mole/l, the polymerisation rate may be undesirably slow. Similarly, if the concentration of dormant chains is less than about $10^{-4}$ mole/l, the molecular weight of the polymer produced may increase dramatically, thus leading to a potential loss of control of its polydispersity. On the other hand, if the concentration of dormant species is greater than 1 mole/l, the molecular weight of the reaction product may likely become too small and result in the properties of an oligomer with no more than about 10 monomeric units. In bulk, a concentration of dormant chains of about $10^{-2}$ mole/l provides a polymer having a molecular weight of about 100,000 g/mole.

The various catalytic components of the present invention are suitable for the radical polymerisation of any radically polymerizable, ethylenically or acetylenically unsaturated compound, including acrylic acid, methacrylic acid, acrylic acid esters, methacrylic acid esters, acrylic acid amides, methacrylic acid amides, imides (such as N-cyclohexylmaleimide and N-phenylmaleimide), styrenes, dienes or mixtures thereof. By providing the said compounds in a single step or in a multi-steps procedure, they are able to provide controlled copolymers having various structures, including block, random, gradient, star, graft, comb, hyperbranched and dendritic (co)polymers.

More specifically, monomers suitable for living radical polymerization (ATRP) according to the seventh embodiment of the present invention include those of the formula R$_{31}$R$_{32}$C=C R$_{33}$R$_{34}$ wherein:

R$_{31}$ and R$_{32}$ are independently selected from the group consisting of hydrogen, halogen, CN, CF$_3$, C$_{1-20}$ alkyl (preferably C$_{1-6}$ alkyl), α,β-unsaturated C$_{2-20}$ alkynyl (preferably acetylenyl), α,β-unsaturated C$_{2-20}$ alkenyl (preferably vinyl) optionally substituted (preferably at the α position) with a halogen, C$_{3-8}$ cycloalkyl, phenyl optionally bearing 1 to 5 substituents, R$_{33}$ and R$_{34}$ are independently selected from the group consisting of hydrogen, halogen (preferably fluorine or chlorine), $C_{1-6}$ alkyl and $COOR_{35}$ (where $R_{35}$ is selected from hydrogen, an alkali metal, or $C_{1-6}$ alkyl), and at least two of $R_{31}$, $R_{32}$, $R_{33}$ and $R_{34}$ are hydrogen or halogen.

Accordingly, suitable vinyl heterocycles which can be used as a monomer for ATRP in the present invention include 2-vinyl pyridine, 6-vinyl pyridine, 2-vinyl pyrrole, 5-vinyl pyrrole, 2-vinyl oxazole, 5-vinyl oxazole, 2-vinyl thiazole, 5-vinyl thiazole, 2-vinyl imidazole, 5-vinyl imidazole, 3-vinyl pyrazole, 5-vinyl pyrazole, 3-vinyl pyridazine, 6-vinyl pyridazine, 3-vinyl isoxazole, 3-vinyl isothiazoles, 2-vinyl pyrimidine, 4-vinyl pyrimidine, 6-vinyl pyrimidine, and any vinyl pyrazine, the most preferred being 2-vinyl pyridine.

Other preferred monomers include:

(meth)acrylic esters of $C_{1-20}$ alcohols, acrylonitrile, cyanoacrylic esters of $C_{1-20}$ alcohols, didehydromalonate diesters of $C_{1-6}$ alcohols, vinyl ketones preferably wherein the a carbon atom of the alkyl group does not bear a hydrogen atom, and styrenes optionally bearing a $C_{1-6}$ alkyl group on the vinyl moiety (preferably at the α carbon atom) and from 1 to 5 substituents on the phenyl ring, said substituents being selected from the group consisting of $C_{1-6}$ alkyl, $C_{1-6}$ alkenyl (preferably vinyl), $C_{1-6}$ alkynyl (preferably acetylenyl), $C_{1-6}$ alkoxy, halogen, nitro, carboxy, $C_{1-6}$alkoxycarbonyl, hydroxy protected with a $C_{1-6}$ acyl group, cyano and phenyl.

The most preferred monomers are methyl acrylate, methyl methacrylate, butyl acrylate, 2-ethylhexyl acrylate, acrylonitrile, maleimide and styrene.

In this seventh embodiment of the invention, the catalytic component of the invention is more preferably used in combination with one or more initiators having a radically transferable atom or group, since an ATRP catalytic system is based on the reversible formation of growing radicals in a redox reaction between the metal component and an initiator.

Suitable initiators may be selected from the group consisting of compounds having the general formula $R_{35}R_{36}R_{37}CX_1$ wherein:

$X_1$ is selected from the group consisting of halogen, $OR_{38}$ (wherein $R_{38}$ is selected from $C_{1-20}$ alkyl, polyhalo $C_{1-20}$alkyl, $C_{2-20}$ alkynyl (preferably acetylenyl), $C_{2-20}$ alkenyl (preferably vinyl), phenyl optionally substituted with 1 to 5 halogen atoms or $C_{1-6}$ alkyl groups and phenyl-substituted $C_{1-6}$ alkyl), $SR_{39}$, $OC(=O)R_{39}$, $OP(=O)R_{39}$, $OP(=O)(OR_{39})_2$, $OP(=O)OR_{39}$, O—N $(R_{39})_2$ and S—C(=S)N$(R_{39})_2$, wherein $R_{39}$ is aryl or $C_{1-20}$ alkyl, or where an N$(R_{39})_2$ group is present, the two $R_{39}$ groups may be joined to form a 5, 6 or 7-membered heterocyclic ring (in accordance with the definition of heteroaryl above), and $R_{35}$, $R_{36}$ and $R_{37}$ are each independently selected from the group consisting of hydrogen, halogen, $C_{1-20}$ alkyl (preferably $C_{1-6}$alkyl), $C_{3-8}$cycloalkyl, $C(=O)R_{40}$, (wherein $R_{40}$ is selected from the group consisting of $C_{1-20}$ alkyl, $C_{1-20}$ alkoxy, aryloxy or heteroaryloxy), $C(=O)NR_{41}R_{42}$ (wherein $R_{41}$ and $R_{42}$ are independently selected from the group consisting of hydrogen and $C_{1-20}$ alkyl or $R_{41}$ and $R_{42}$ may be joined together to form an alkylene group of 2 to 5 carbon atoms), COCl, OH, CN, $C_{2-20}$ alkenyl (preferably vinyl), $C_{2-20}$ alkynyl, oxiranyl, glycidyl, aryl (optionally alkyl-substituted), heteroaryl, arylalkyl and aryl-substituted $C_{2-20}$ alkenyl.

In these initiators, $X_1$ is preferably bromo, which provides both a higher reaction rate and a lower polymer polydispersity.

When an alkyl, cycloalkyl, or alkyl-substituted aryl group is selected for any one of $R_{35}$, $R_{36}$ and $R_{37}$, said alkyl group may be further substituted with an $X_1$ group as defined above; thus, it becomes possible for the initiator to serve as a starting molecule for branch or star (co)polymers. One example of such an initiator is a 2,2-bis(halomethyl)-1,3-dihalopropane (e.g. 2,2-bis(chloromethyl)-1,3-dichloropropane or 2,2-bis (bromomethyl)-1,3-dibromopropane), and a preferred example is where one of $R_{35}$, $R_{36}$ and $R_{37}$ is phenyl substituted with from one to five $C_{1-6}$ alkyl substituents, each of which may independently be further substituted with a $X_1$ group (e.g. α,α'-dibromoxylene, hexakis(α-chloro- or α-bromomethyl)benzene).

Preferred initiators include 1-phenylethyl chloride and 1-phenylethyl bromide, chloroform, carbon tetrachloride, 2-chloropropionitrile and $C_{1-6}$alkyl esters of a 2-halo-$C_{1-6}$ saturated monocarboxylic acid (such as 2-chloropropionic acid, 2-bromo-propionic acid, 2-chloroisobutyric acid, 2-bromoisobutyric acid and the like). Another example of a suitable initiator is dimethyl-2-chloro-2,4,4-trimethylglutarate.

Any transition metal compound which can participate in a redox cycle with the initiator and dormant polymer chain, but which does not form a direct carbon-metal bond with the polymer chain, such as ruthenium, osmium, iron, molybdenum, tungsten, titanium, rhenium, technetium, lanthanum, copper, chromium, manga-nese, rhodium, vanadium, zinc, gold, silver, nickel and cobalt, is suitable for use in this embodiment of the present invention. In this seventh embodiment of the invention, the catalytic metal carbene component of the invention may be one wherein the anionic ligand $R_2$ is preferably selected from the group consisting of halogen, $C_{1-6}$alkoxy, sulfate, phosphate, hydrogenophosphate, triflate, hexafluorophosphate, methanesulfonate, arylsulfonate (preferably benzenesulfonate or toluenesulfonate), cyano, tetrafluoroborate and $C_{1-6}$ carboxylate. As is well known to those skilled in the art, one such catalytic component having a anionic ligand like tetrafluoroborate may suitably be prepared by ligand exchange by reacting a metal carbene compound having a halogen as the anionic ligand $R_2$ with a metal compound having another anion, e.g. silver tetrafluoroborate, which is able to extract and replace the halogen atom, thus giving rise to a cationic alkylidene complex. It was unexpectedly found that such cationic alkylidene complexes exhibit better catalytic activity than the corresponding metal carbene complexes being coordinated with a halogen ligand.

In this aspect of the present invention, the amounts and relative proportions of the initiator and the transition metal carbene compound are those which are typically effective to conduct ATRP. The molar proportion of the transition metal carbene compound with respect to the initiator may be from 0.0001:1 to 10:1, preferably from 0.1:1 to 5:1, more preferably from 0.3:1 to 2:1, and most preferably from 0.9:1 to 1.1:1.

ATRP according to the invention may be conducted in the absence of a solvent, i.e. in bulk. However, when a solvent is used, suitable solvents include ethers, cyclic ethers, alkanes, cycloalkanes, aromatic hydrocarbons, halogenated hydrocarbons, acetonitrile, dimethylformamide and mixtures thereof, and supercritical solvents (such as $CO_2$). ATRP may also be conducted in accordance with known suspension, emulsion or precipitation methods. Suitable ethers include diethyl ether, ethyl propyl ether, dipropyl ether, methyl t-butyl ether, di-t-butyl ether, glyme (dimethoxyethane) diglyme (diethylene glycol dimethyl ether), etc. Suitable cyclic ethers include tetrahydrofuran and dioxane. Suitable alkanes include pentane, hexane, cyclohexane, octane and dodecane. Suitable aromatic hydrocarbons include benzene, toluene, o-xylene, m-xylene, p-xylene and cumene. Suitable halogenated hydrocarbons include dichloromethane, 1,2-dichloroethane and benzene substituted with 1 to 6 fluorine and/or chlorine atoms, although one should ensure that the selected halogenated hydrocarbon does not act as an initiator under the reaction conditions.

ATRP may also be conducted in the gas phase (e.g. by passing the gaseous monomer(s) over a bed of the catalytic system), in a sealed vessel or in an autoclave. (Co)polymerization may be conducted at a temperature from about 0° C. to 160° C., preferably from about 60° C. to 120° C. Typically, the reaction time will be from about 30 minutes to 48 hours, more preferably from 1 to 24 hours. (Co)polymerization may be conducted at a pressure of from about 0.1 to 100 atmospheres, preferably from 1 to about 10 atmospheres.

According to another embodiment, ATRP may also be conducted in emulsion or suspension in a suspending medium for suspending the monomer(s) and while using the metal carbene complex of the invention in combination with a surfactant, in a way such as to form a (co)polymer emulsion or suspension. The suspending medium usually is an inorganic liquid, preferably water. In this embodiment of the invention, the weight ratio of the organic phase to the suspending medium is usually between 1:100 and 100:1, preferably between 1:10 and 10:1. If desired, the suspending medium may be buffered. Preferably the surfactant will be selected in order to control the stability of the emulsion, i.e. to form a stable emulsion.

In order to conduct polymerization in a heterogeneous medium (where the monomer/polymer is insoluble, or only slightly soluble, in the suspension medium, i.e. water or $CO_2$), the metal catalyst component should be at least partially soluble in the monomer/polymer. Thus, only when ligands are properly selected to allow the catalyst to meet this requirement, such as ligands containing long alkyl chains to increase catalyst solubility in hydrophobic monomers targeted for polymerization, is a successful, controlled ATRP polymerization obtained in the water-borne systems of this embodiment. From the above description of ligands coordinating the metal M in the catalytically active metal carbene complexes of the invention, those skilled in the art will be able to make a suitable selection.

A key component in the preparation of the stable emulsions of the present embodiment is the use of the surfactant to stabilize the initial monomer suspension/emulsion and growing polymer particles and to prevent unwanted coagulation/flocculation of the particles. In order to conduct ATRP in emulsion however, care should be taken to choose a surfactant which does not interfere with the catalyst or dormant chain end. Suitable surfactants include non-ionic, anionic, and cationic surfactants, with cationic and non-ionic surfactants being preferred in non-buffered solutions. Particularly preferred non-ionic surfactants include polyethylene glycol, polyoxyethylene oleyl ethers and polyoxythylene sorbitan monoalkyls. A preferred cationic surfactant is dodecyltrimethyl ammonium bromide. Regardless of the surfactant used, efficient stirring is preferred to obtain good dispersions or latexes.

The surfactant is usually present in a concentration of about 0.01% to 50% by weight based on the total weight of all components introduced into the polymerisation reactor, i.e. suspending medium, monomer(s), surfactant and catalytic system.

High solubility in the suspension medium is not a prerequisite for the initiator as demonstrated by the use of the poorly water soluble ethyl 2-bromoisobutyrate, to initiate the emulsion polymerizations. While any order of addition of the initiator and other reaction components can be used, however if the initiator is added to a pre-emulsified reaction mixture, stable latexes are usually obtained. Suitable initiators have been described herein-above in the solvent embodiment of the ATRP process. Initiators can also be macromolecules that contain radically transferable atoms or groups. A special type of such a macroinitiator may be water-soluble or even amphiphilic and may be, after initiation of the reaction, incorporated into the polymer particle and may stabilize the growing particle due to the hydrophilic segment of the macroinitiator.

After completing the (co)polymerization step of the ATRP process of this invention, the (co)polymer formed may be isolated by known procedures such as, but not limited to, precipitating in a suitable solvent, filtering the precipitated polymer, then washing and drying the filtered polymer. Precipitation can be typically conducted using a suitable alkane or cycloalkane solvent, such as pentane hexane, heptane, cyclohexane or mineral spirits, or using an alcohol, such as methanol, ethanol or isopropanol, or any mixture of suitable solvents. The precipitated (co)polymer can be filtered by gravity or by vacuum filtration, e.g. using a Buchner funnel and an aspirator. The polymer can then be washed with the solvent used to precipitate the polymer, if desired. The steps of precipitating, filtering and washing may be repeated, as desired. Once isolated, the (co)polymer may be dried by drawing air through the (co)polymer, by vacuum. The dried (co)polymer can then be analyzed and/or characterized e.g. by size exclusion chromatography or NMR spectroscopy.

(Co)polymers produced by the catalytic process of the invention may be useful in general as molding materials (e.g. polystyrene) and as barrier or surface materials (e.g. polymethyl methacrylate). However, typically having more uniform properties than polymers produced by conventional radical polymerization, will be most suitable for use for specialized applications. For example, block copolymers of polystyrene (PSt) and polyacrylate (PA), e.g. PSt-PA-PSt triblock copolymers, are useful thermoplastic elastomers. Polymethylmethacrylate/acrylate triblock copolymers (e.g. PMMA-PA-PMMA) are useful, fully acrylic, thermoplastic elastomers. Homo- and copolymers of styrene, (meth)acrylates and/or acrylonitrile are useful plastics, elastomers and adhesives. Either block or random copolymers of styrene and a (meth) acrylate or acrylonitrile are useful thermoplastic elastomers having high solvent resistance. Furthermore, block copolymers in which blocks alternate between polar monomers and non-polar monomers produced by the present invention are useful amphiphilic surfactants or dispersants for making highly uniform polymer blends. Star (co)polymers, e.g. styrene-butadiene star block copolymers, are useful high-impact copolymers.

(Co)polymers produced by the catalytic process of the present invention typically have a number average molecular weight from about 1,000 to 1,000,000, preferably from 5,000 to 250,000, more preferably from 10,000 to 200,000 and most preferably from 25,000 to 150,000. Their structure, due to the high degree of flexibility of living radical polymerization, may include block, multi-block, star, gradient, random, hyperbranched, graft, "comb-like" and dendritic copolymers. Each of the these different types of copolymers will be described hereunder.

Because ATRP is a living polymerization process, it can be started and stopped, practically at will. Further, the polymer product retains the functional group $X_1$ necessary to initiate a further polymerization. Thus, in a specific embodiment, once a first monomer is consumed in the initial polymerizing step, a second monomer can then be added to form a second block on the growing polymer chain in a second polymerizing step. Further additional polymerizations with the same or different monomer(s) can be performed to prepare multi-block copolymers. Furthermore, since ATRP is also a radical polymerization, these blocks can be prepared in essentially any order.

(Co)polymers produced by the catalytic ATRP process of the present invention have a very low polydispersity index, i.e. the ratio $M_w/M_n$ of their weight average molecular weight to their number average molecular weight is typically from about 1.1 to 2.4, preferably from 1.15 to 2.0, more preferably from 1.2 to 1.8.

Because the living (co)polymer chains retain an initiator fragment including $X_1$ as an end group, or in one embodiment as a substituent in a monomeric unit of the polymer chain, they may be considered as end-functional or in-chain functional (co)polymers. Such (co)polymers may thus be converted into (co)polymers having other functional groups (e.g. halogen can be converted into hydroxy or amino by known processes, and nitrile or carboxylic ester can be hydrolyzed to a carboxylic acid by known processes) for further reactions, including crosslinking, chain extension (e.g. to form long-chain polyamides, polyurethanes and/or polyesters), reactive injection molding, and the like.

Five-coordinate metal complexes of the invention are also useful in the addition polymerisation of one or more α-olefins having from 2 to 12 carbon atoms, optionally in combination with one or more dienes having from 4 to 20 carbon atoms. More preferably, the catalytically active five-coordinate metal complex for such a reaction is one wherein the multidentate ligand affords a five-member ring structure with the metal, such as a complex having the general formula (IB). Also preferably, the said complex is used in a catalytic system for the addition polymerisation of one or more α-olefins having from 2 to 12 carbon atoms, optionally in combination with one or more dienes having from 4 to 20 carbon atoms, comprising:

(A) a complex having the general formula (IB),
(B) a compound having the ability to react with compound (A) to convert the imine moiety thereof into a metal amine structure, and
(C) a compound having the ability to react with compound (A) to form an ion pair.

Suitable compounds (B) for this purpose include organoaluminum compounds, in particular tri-n-alkylaluminums (such as triethylaluminum, tri-n-butylaluminum, tri-n-propylaluminum, tri-n-butylaluminum, tri-n-pentylaluminum, tri-n-hexylaluminum, tri-n-octylaluminum, tri-n-decylaluminum, and their branched chain analogues; dialkylaluminum hydrides, trialkenylaluminums, alkylaluminum alkoxides, dialkylaluminum alkoxides, dialkylaluminum aryloxides, dialkylaluminum halides. Suitable compounds (C) for this purpose include Lewis acids (preferably boron trifluoride and triarylboron), ionic compounds (such as carbonium, oxonium, ammonium, phosphonium, ferrocenium and the like), borane compounds (such as decaborane) and salts thereof, metallic carboranes and heteropoly compounds such as phosphomolybdic acid, silicomolybdic acid, phosphomolybdovanadic acid and the like.

The above catalytic system is efficient in polymerising alpha-olefins, continously or batchwise, at moderate temperatures ranging from about 40° C. to about 80° C. under atmospheric pressure, and in obtaining well-defined polymers with high productivity.

If desired, removal of the transition metal catalyst from the polymerisation medium can be accomplished by the addition of a commercially available ion exchange resin such as is well known in the art. However, as explained hereinafter, it may also be desirable to modify the said catalyst into a dendrimeric material in order to facilitate its removal by ultra-filtration techniques.

In order to facilitate the use of the five-coordinate metal carbene compounds of the invention in heterogeneous catalytic reactions, the present invention further relates to silyl derivatives of such compounds, being suitable for covalent bonding to a carrier, especially those complexes wherein the multidentate ligand is a bidentate or tridentate Schiff base, e.g. having one of the general formulae (IA) and (IB). In such silyl derivatives, R' and/or R" of the said general formulae is replaced or substituted with a group having the formula:

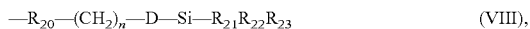

$$—R_{20}—(CH_2)_n—D—Si—R_{21}R_{22}R_{23} \qquad (VIII),$$

wherein:

$R_{20}$ is a radical selected from the group consisting of $C_{1-6}$ alkylene, arylene, heteroarylene and $C_{3-8}$ cycloalkylene, the said radical being optionally substituted with one or more $R_{24}$ substituents each independently selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy, $C_{2-20}$ alkoxycarbonyl, $C_{1-20}$ alkylsulfonyl, $C_{1-20}$ alkynylsulfinyl, $C_{1-20}$ alkylthio, aryloxy and aryl;

D is a divalent atom or radical selected from the group consisting of oxygen, sulphur, silicon, arylene, methylene, $CHR_{24}$, $C(R_{24})_2$, NH, $NR_{24}$ and $PR_{24}$;

$R_{21}$, $R_{22}$ and $R_{23}$ are each independently selected from the group consisting of hydrogen, halogen and $R_{24}$; and n is an integer from 1 to 20;

provided that at least one of $R_{21}$, $R_{22}$ and $R_{23}$ is selected from the group consisting of $C_{1-20}$ alkoxy, $C_{2-20}$ alkenyloxy, $C_{2-20}$ alkynyloxy, $C_{2-20}$ alkoxycarbonyl, $C_{1-20}$ alkylsulfonyl, $C_{1-20}$ alkynylsulfinyl, $C_{1-20}$ alkylthio and aryloxy.

More preferred within the above group are such silyl derivatives wherein R' is replaced or substituted with a 3-(triethoxysilyl)propyl or 2-(triethoxysilyl)propyl group. Alternatively suitable derivatives include shaped organosiloxane copolycondensation products such as disclosed in EP-A-484,755.

In another embodiment, the invention relates to a supported catalyst, especially for use in a heterogeneous catalytic reaction, comprising the product of covalent bonding of (a) a silyl derivative such as defined hereinabove, and (b) a carrier including one or more inorganic oxides or an organic polymeric material. Preferably the said inorganic carrier is selected from silica, alumina, alumino-silica, zirconia, natural and synthetic zeolites and mixtures thereof, or the said organic polymeric carrier may be a polystyrene resin or a derivative thereof wherein the aromatic ring is substituted with one or more groups selected from $C_{1-6}$ alkyl, $C_{3-10}$ cycloalkyl, aryl and heteroaryl. More detailed examples of such suitable carriers were already disclosed hereinabove.

As previously mentioned, the novel metal carbene complexes of the invention, as well as some metal complexes of the prior art (U.S. Pat. No. 5,977,393) are also active catalyst components in acetylene metathesis involving a metallacyclobutadiene intemediate) or in reactions, other than ATRP or ATRA, involving the transfer of an atom or group to an ethylenically or acetylenically unsaturated compound or another reactive substrate such as, but not limited to, saturated hydrocarbons, aldehydes, ketones, alcohols, alkyl halides and the like. Briefly, acetylene metathesis may be referred to herein as a reaction in which all carbon-carbon triple bonds in a mixture of alkynes are cut and then rearranged in a statistical fashion.

An atom or group transfer reaction usually comprises the step of reacting an ethylenically or acetylenically unsaturated compound or other first reactive substrate with a second reactive substrate under suitable reaction conditions and in the presence of a suitable catalytic component, the second reactive substrate being a suitable donor for the atom or group to be transferred. In this aspect of the invention, the catalytic component may be a novel transition metal carbene complex such as described herein, but is not limited thereto and may also be a ruthenium or osmium complex of the prior art (U.S. Pat. No. 5,977,393) or a complex including similar ligands but derived from another transition metal such as, but not limited to, iron, molybdenum, tungsten, titanium, rhenium, technetium, lanthanum, copper, chromium, manganese, rhodium, vanadium, zinc, gold, silver, cobalt and nickel.

More specifically, the said atom or group transfer reactions (which will be detailed below), other than ATRP or ATRA, may be, but without limitation, selected from the group consisting of:

vinylation reactions, i.e. the reaction of a mono- or di-alkyne (e.g. phenylacetylene or 1,7-octadiyne) with a monocarboxylic acid (e.g. formic acid or acetic acid) or dicarboxylic acid to produce alk-1-enyl esters or enol esters or Markovnikov adducts or anti-Markovnikov adducts or mixtures thereof;

cyclopropanation of an α-ethylenically unsaturated compound for producing an organic compound having one or more cyclopropane structural units;

quinoline synthesis through oxidative cyclisation of 2-aminobenzyl alcohol with ketones;

epoxidation of α-ethylenically unsaturated compounds for producing epoxides;

oxidation of organic compounds including the oxidation of saturated hydrocarbons (such as, but not limited to, methane) for producing alcohols, or sulfides for producing sulfoxides and sulfones, or phosphines for producing phosphonates, or alcohols and aldehydes for producing carboxylic acids;

cyclopropenation of an alkyne for producing an organic compound having one or more cyclopropene structural units;

hydrocyanation of α-ethylenically unsaturated compounds for producing saturated nitriles, or alkynes for producing unsaturated nitriles, or α,β-unsaturated aldehydes or ketones for producing β-cyano carbonyl compounds;

hydrosilylation of olefins for producing saturated silanes, or alkynes for producing unsaturated silanes, or ketones for producing silyl ethers, or trimethylsilylcyanation of aldehydes for producing cyanohydrin trimethylsilyl ethers;

aziridination of imines or alkenes for producing organic compounds having one or more aziridine structural units;

hydroamidation of olefins for producing saturated amides;

hydrogenation of olefins for producing alkanes, or ketones for producing alcohols;

aminolysis of olefins for producing saturated primary or secondary amines;

isomerisation of alcohols, preferably allylic alcohols, for producing aldehydes;

Grignard cross-coupling of alkyl or aryl halides for producing alkanes or arylalkanes;

hydroboration of olefins for producing alkylboranes and trialkylboranes;

hydride reduction of aldehydes and ketones for producing alcohols;

aldol condensation of saturated carboxyl compounds (aldehydes or ketones) for producing α,β-unsaturated carboxyl compounds or β-hydroxycarbonyl compounds, and intra-molecular aldol condensation of dialdehydes or diones for producing cyclic α,β-unsaturated carboxyl compounds (aldehydes or ketones);

Michael addition of a ketone or a β-dicarbonyl compound onto an α,β-unsaturated carboxyl compound for producing saturated polycarboxyl compounds;

Robinson annelation, i.e. Michael addition followed by an intramolecular aldol condensation, of a ketone onto an α,β-unsaturated carboxyl compound for producing saturated polycyclic carboxyl compounds being suitable intermediates for steroids and other natural products containing six-membered rings;

Heck reactions, i.e. the reaction of an aryl halide or a 1-hetero-2,4-cyclopentadiene (or a benzo-fused derivative thereof with an α-ethylenically unsaturated compound for producing arylalkenes or heteroarylalkenes;

codimerisation of alkenes for producing higher saturated hydrocarbons or alkynes for producing higher alkenes;

hydroxylation of olefins for producing alcohols;

alkylation, preferably allylic alkylation, of ketones for producing alkylated ketones, preferably allylic ketones; and Diels-Alder reactions such as, but not limited to, the cycloaddition of a conjugated diene onto an α-ethylenically unsaturated compound for producing optionally substituted cyclohexenes, or the cycloaddition of furan onto an α-ethylenically unsaturated compound for producing optionally substituted 7-oxanorbornenes.

Each type of the above organic synthesis reactions, which will be described in some more detail hereinafter, is known per se but to the best of our knowledge was never performed with transition metal complexes similar to those described herein. For further details on each type of reaction, reference may be made for instance to K. Vollhardt and N. Schore, *Organic chemistry, structure and function* (1999) by W. H. Freeman (3$^{rd}$ edition), to B. Cornils and A. Herrmann, *Applied homogeneous catalysis with organometallic compounds* (2000) by Wiley & Sons, and to S. Warren, *Organic synthesis, the disconnection approach* (1982) by Wiley & Sons.

Each organic synthesis reaction of this aspect of the invention may be conducted in a continuous, semi-continuous, or batch manner and may involve a liquid and/or gas recycling operation as desired. The manner or order of addition of the reactants, catalyst, and solvent are usually not critical. Each organic synthesis reactions may be carried out in a liquid reaction medium that contains a solvent for the active catalyst, preferably one in which the reactants, including catalyst, are substantially soluble at the reaction temperature.

The catalytic components of this invention are thus useful in the cyclopropanation of ethylenically unsaturated compounds, or the intramolecular cyclopropanation of α-diazoketones or α-diazo-β-ketoesters for producing compounds having one or more cyclopropane structural units in the hydrocarbon chain. This embodiment of the invention is thus useful in one or more manufacturing steps of the following natural and synthetic cyclopropyl-containing compounds. Cyclopropyl-containing compounds may be found in naturally occurring terpenes, steroids, amino-acids, fatty acids, alkaloids and nucleic acids. For instance, chrysanthemic acid derivatives (such as pyrethrines) produced in plants are precursors to potent insecticides. The invention is also applicable to making synthetic pyrethroid insecticides such as deltamethrin, as well as sirenine, aristolon, sesquicarene and cyclopropyl derivatives being intermediates in the synthesis of the steroid hirsutene or the antibiotic sarkomycine. Cyclopropyl-containing non-natural compounds also have biological activity, such as Cipro, a powerful anti-anthrax drug, or cyclopropane amino-acids (e.g. 2,3-methanophenylalanine, the anti-Parkinson drug 2,3-methano-m-tyrosine, coronatine and coronamic acid). Polycyclopropane fatty acid derivatives isolated from fungi, U-106305 (a cholesteryl ester transfer protein inhibitor) and FR-900848 (a nucleoside analogue), are also candidates for such synthetic production. Ethylenically unsaturated compounds that may be cyclopropanated according to this invention into the correspondingly cyclopropyl-containing compounds are not particularly limited but include, without restriction, compounds having terminal ethylenic unsaturation such as styrene (which, in the presence of ethyl diazoacetate, may be transformed into ethyl-2-phenyl-cyclopropanecarboxylate) and substituted derivatives thereof (e.g. 4-chlorostyrene, α-methylstyrene and vinylstyrene), 2-vinyinaphtalene, 1,1-diphenyl-ethylene, 1-decene, functional α-olefins wherein the functional group is preferably adjacent to the ethylenic unsaturation and is preferably a protected alcohol such as in protected allylic alcohols such as acyclic allylic silyl ethers (which may be transformed into cyclopropylcarbinyl silyl ethers) or a carboxy group such as in acrylic and methacrylic acids (as well as esters, thioesters, amides or anhydrides thereof), cinnamate esters, alkenylboronic esters (such as 2-methylethenyl-4,5-bis[methoxy-diphenylmethyl]-1,3,2-dioxaborolanes or derivatives thereof wherein the methyl group is protected by a protecting group such as, but not limited to, ter-butyidimethylsiloxy, ter-butyi-diphenylsiloxy, benzyloxy, methoxymethoxy or benzoyloxy, which may be transformed into the corresponding cyclopropylboronic esters), 2-phenylsulfonyl-1,3-dienes and cycloolefins such as cyclooctene. Such reaction preferably takes place in the presence of a diazo compound such as, but not limited to, ethyl diazoacetate, cinnamyl diazoacetate, dicyclohexylmethyl diazoacetate, vinyl diazoacetate, menthyl diazoacetate or 1-diazo-6-methyl-5-hepten-2-one, at moderate temperatures usually ranging from about 0° C. to 80° C., preferably 20 to 60° C., the reaction time ranging from about 1 to 12 hours, and in a relatively low boiling solvent such as methylene chloride, tetrahydrofuran, ethanol, isopropanol, tert-butanol, L-menthol or water, or mixtures thereof. The diazo compound may be added as such or, in order to eliminate the handling risks associated with its explosive nature, may be generated in situ by reacting an acetoammonium salt with sodium nitrite in the presence of the ethylenically unsaturated compound. When water or an aqueous mixture is selected as the reaction solvent, it is preferable to use a cationic metal complex species as the catalytic component, the said cationic species being associated with an anion A as described hereinabove. Preferably the molar ratio of the ethylenically unsaturated compound to the catalytic component is in a range from 200 to 2,000, more preferably from 250 to 1,500. The molar ratio of the ethylenically unsaturated compound with respect to the diazo compound is conventional for this kind of reaction, i.e. a molar excess of the former compound. The cyclopropanation of ethylenically unsaturated compounds may optionally be carried out in the presence of a tertiary aliphatic amine, such as triethylamine or tri-n-butylamine, or a heterocyclic amine such as pyridine or lutidine as a co-catalyst. The intramolecular cyclopropanation of α-diazo carbonyl compounds such as α-diazo ketones or α-diazo-β-ketoesters may also be performed acccording to similar reaction conditions (temperature, reaction time, substrate/catalyst ratio) and may result in bicyclic molecules wherein the cyclopropyl group may be fused to another cycloaliphatic group, e.g. a cyclopentanone such as in the synthesis of intermediates of hirsutene or sarkomycin, or a cyclopentyl group when starting from acetylenic α-diazo ketones. However, it should be noted that, in accordance with the teachings of Padwa in *Molecules* (2001) 6:1-12, the cyclisation of an acetylenic α-diazo ketone in the presence of a catalytic component of this invention may also lead to the formation of other polycyclic ring systems such as, but not limited to, cyclopentanone fused to a furan, an alkenyl-substituted indenone, a cyclopropyl-substituted indenone, a cyclopentazulenone or a cyclopentadiene fused to indenone.

The catalytic components of this invention are also useful in the cyclopropenation of alkynes for producing compounds having one or more cyclopropene structural units in the hydrocarbon chain. This applies in particular to alkynes having a $C_{2-6}$ alkynyl group such as, but not limited to, 1-hexyne, 3,3-dimethyl-1-butyne, phenyl-acetylene, cyclohexylacetylene, methoxy-methylacetylene and acetoxymethyl-acetylene which may be converted in good yields into ethylcyclo-propene-3-carboxylates in the presence of a diazo compound such as, but not limited to, ethyl diazoacetate, cinnamyl diazoacetate, dicyclohexylmethyl diazoacetate, vinyl diazoacetate, 1-diazo-6-methyl-5-hepten-2-one or menthyl diazoacetate. This invention also relates to the intramolecular cyclopropenation of acetylenic α-diazo ketones, leading for instance to cyclopropenyi-containing compounds such as cyclopropenyl substituted indenones. Reaction conditions (temperature, time) and catalyst/substrate ratios suitable for the cyclopropenation of alkynes are well known in the art.

The catalytic components of this invention are also useful in quinoline synthesis through oxidative cyclisation of 2-aminobenzyl alcohol with ketones (i.e. the so-called Friedlaender reaction). Such reaction preferably takes place with a molar excess of the said ketone, under basic conditions (such as in the presence of an alkali hydroxide), at moderate temperatures usually ranging from about 20 to about 100° C. and optionally in the presence of a solvent. Preferably the ratio of the 2-aminobenzyl alcohol to the catalytic component of the invention is in a range from 100 to 2,000, preferably from 200 to about 1,000. A number of alkylarylketones, alkyl heteroaryl-ketones, dialkylketones and benzo-fused cyclic ketones may be used in this process of the invention, including $C_{1-7}$alkylketones wherein the second hydrocarbon attached to the oxo group may be methyl, pentyl, isopropyl, phenethyl, phenyl, toluyl, anisyl, nitrophenyl, hydroxyphenyl, fluorophenyl, trifluoromethylphenyl, cyanophenyl, naphtyl, furanyl, thiophenyl, pyridyl, and the like. Exemplary ketones which may be cyclised to quinolines according to this embodiment of the invention include, but are not limited to, acetophenone, 3-methylacetophenone, cyclohexanone, 4-phenyl-cyclohexanone and propiophenone. Other suitable ketones for this purpose are as disclosed by Cho et al. in *Chem. Commun.* (2001) 2576-2577. Unexpectedly, by making use of the catalytic components of this invention, ketones such as cyclohexanone may be converted into the corresponding quinoline with a yield significantly higher, under equivalent reaction conditions, than achieved by the ruthenium catalyst used in the latter publication.

The catalytic components of this invention are also useful in the intramolecular epoxidation, including the asymmetric epoxidation, of ethylenically unsaturated compounds, i.e. alkenes, for producing the corresponding epoxides (i.e. oxacyclo-propyl-containing compounds). Such alkenes include for instance, but without limitation, styrene and analogues thereof (such as α-methylstyrene, p-chorostyrene, p-trifluoromethylstyrene and the like) or cholesterol acetate. Illustrative olefinic starting reactants useful in the asymmetric epoxidation of this invention include those which can be terminally or internally unsaturated and be of straight chain, branched chain, or cyclic structure. Such olefinic reactants may contain from 3 to about 40 carbon atoms and may contain one or more ethylenically unsaturated groups. Moreover, such olefinic reactants may contain groups or substituents which do not essentially adversely interfere with the asymmetric epoxidation process such as carbonyl, carbonyloxy, oxy, hydroxy, oxycarbonyl, halogen, alkoxy, aryl, haloalkyl, and the like. Illustrative olefinic unsaturated compounds include substituted and unsubstituted alpha-olefins, internal olefins, alkyl alkenoates, alkenyl alkanoates, alkenyl alkyl ethers, alkenols, and the like, e.g. propylene, 1-butene, 1-pentene, 1-hexene, 1-octene, 1-decene, 1-dodecene, 1-octadecene, 2-butene, isoamylene, 2-pentene, 2-hexene, 3-hexene, 2-heptene, cyclohexene, 2-ethylhexene, 3-phenyl-1-propene, 1,4-hexadiene, 1,7-octadiene, 1,5,9-dodecatriene, 3-cyclohexyl-1-butene, allyl alcohol, hex-1-en-4-ol, oct-1-en-4-ol, vinyl acetate, allyl acetate, aryloates such as vinyl benzoate and the like, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, substituted and unsubstituted chromenes, 2,2-dimethylcyclochromene, 3-butenenitrile, 5-hexenamide, indene, 1,2-dihydronaphthalene, 2-vinyinaphtalene, norbornene, cis-stilbene, trans-stilbene, p-isobutylstyrene, 2-vinyl-6-methoxy-naphthylene, 3-ethenylphenyl phenylketone, 4-ethylphenyl-2-thienylketone, 4-ethenyl-2-fluoro-biphenyl, 4-(1 m,3-dihydro-1-oxo-2H-isoindol-2-yl) styrene, 2-ethyl-5-benzoylthiophene, 3-ethenyl-phenyl phenylether, isobutyl-4-propenylbenzene, phenyl vinyl ether, 2-cyclohenenyl-1,1-dioxolane, vinyl chloride, benzopyrane and benzofurane type compounds, and substituted aryl ethylenes such as described in U.S. Pat. No. 4,329,507, incorporated herein by reference in its entirety. Epoxidation according to the invention may be applied to the synthesis of biologically active molecules such as cis-stilbene oxide (a substrate for microsomal and cytosolic epoxide hydrolase) and isoprostane.

Such epoxidation reaction preferably takes place in the presence of an at least stoechiometric amount (with respect to the ethylenically unsaturated compound) of an oxygen atom source or oxygen-transfer reagent being relatively unreactive toward olefins in the absence of the catalytic system. The said oxygen atom source or oxygen-transfer reagent may be, but without limitation, selected from the group consisting of hydrogen peroxide (usually in the form of an aqueous solution with a concentration of about 5 to 50% by weight), NaOCl, iodosylmesitylene, NaIO$_4$, NBu$_4$IO$_4$, potassium peroxy-monosulfate, magnesium monoperoxyphthalate, 2,6-dichloropyridine N-oxide and hexacyanoferrate ion. Such epoxidation reaction preferably takes place under conditions and for such time as is needed to epoxidize the olefinic unsaturated compound. Such conditions include, but without limitation:

reaction temperatures usually ranging from about −20° C. to about 120° C., preferably from 0° C. to 90° C., more preferably from 20 to about 40° C., and/or reaction pressures ranging from about 0.1 to about 70 bars, and/or conducting the reaction in the presence of a solvent for the catalytic system, preferably a relatively low boiling organic solvent selected from the group consisting of saturated alcohols, amines, alkanes, ethers, esters, aromatics and the like, and/or a molar ratio of the ethylenically unsaturated compound to the catalytic component in a range from about 200 to about 20,000, preferably from 500 to 10,000, and/or a molar excess of the oxygen-transfer reagent with respect to the olefinic unsaturated compound.

The catalytic components of this invention are also useful in the oxidation of hydrocarbons into alcohols such as, but not limited to, the oxidation of methane (which is known to be more difficult to oxidize than other alkanes) into methanol. Although this process is effective for a wide variety of hydrocarbons, it is particularly effective for the oxidation of straight chain and branched chain alkanes and cycloalkanes with 1 to 15 carbon atoms, and arylalkanes such as toluene, xylene and ethylbenzene. The preferred aliphatic hydrocarbons have 1 to 10 carbon atoms, including ethane, propane, butane, isobutane, hexanes, and heptanes; and the preferred cyclic hydrocarbons have 5 to 10 carbon atoms such as cyclopentane, cyclohexane, cycloheptane, cyclooctane and adamantane. This invention is also applicable to a broad range of hydrocarbons containing various substituents to enhance the rate of oxidation. Oxidation according to this invention may be carried out in a liquid phase, mixed solvent system such as water/acetone, water/acetonitrile and/or acetic acid, which is inert to the conditions of the reaction and to oxidation by molecular oxygen. The temperature can range between 20 and 60° C. The pressure may range from 5 to 20 atmospheres. Depending upon whether the hydrocarbon is a solid, liquid or gas, it is either dissolved in the mixed solvent system or is bubbled through the solvent together with air or oxygen before adding the catalytic component of the invention. A concentration ranging from $10^{-3}$ to $10^{-6}$ moles of the catalytic component in solution is usually sufficient to achieve the desired oxidation. The reaction time preferably ranges from 30 minutes to 30 hours, more preferably from 1 to 5 hours. According to another embodiment, the catalytic component of the sixth aspect of this invention is also useful in the oxidation of allylic and benzylic alcohols into carbonyl compounds.

The present invention also relates to other atom or group transfer reactions such as asymmetric syntheses in which a prochiral or chiral compound is reacted in the presence of an optically active, metal-ligand complex catalyst, in enantiomerically active form, to produce an optically active compound. These reactions, which are useful for the production of numerous classes of products, e.g. sulfoxides, aziridines, enol esters, nitriles, silanes, silyl ethers, alkanes, phosphonates, alkylboranes, hydroxycarbonyl compounds, β-cyano carbonyl compounds, carboxyl compounds, arylalkenes, heteroarylalkenes, cyclohexenes, 7-oxanorbomenes, aldehydes, alcohols, primary or secondary amines, amides and the like, have been listed hereinbefore and will be detailed below.

For instance, the catalytic oxidation of sulfides (into sulfoxides and sulfones), phosphines (into phosphonates), and alcohols or aldehydes into carboxylic acids can be carried out in accordance with conventional oxidation procedures (including temperature, time and substrate/catalyst ratio) known in the art. For example, but without limitation, optically active carboxylic acids can be prepared by reacting a racemic aldehyde and an oxygen atom source in the presence of an optically active metal complex catalytic system as described herein. A number of sulfoxides finding application in the pharmaceutical industry, such as a quinolone sulfoxide described by Matsugi et al. in *Tetrahedron* (2001) 57:2739 (a platelet adhesion inhibitor), or a pyrazolotriazine sulfoxide described by Naito et al. in *Yakugaku Zasshi* (2001) 121:989 (a drug for the treatment of hyperurecemia and ischemic reperfusion injury), or methylphenyl sulfoxide (from methylphenyl thioether) may be made by using such a process step.

Catalytic hydrocyanation (or cyanohydration) of α-ethylenically unsaturated compounds for producing saturated nitriles, or hydrocyanation of alkynes for producing unsaturated nitriles, or of α,β-unsaturated aldehydes or ketones for producing β-cyano carbonyl compounds can also be carried out, while making use of the catalytic components of this invention, in accordance with conventional procedures (including temperature, time and substrate/catalyst ratio) known in the art. For example, 1-phenyl propenone may be transformed into 4-oxo-4-phenyl-butanenitrile, or optically active nitrile compounds can be prepared by reacting a prochiral olefin and hydrogen cyanide in the presence of an optically active metal complex catalytic system as described herein.

Catalytic hydrosilylation of olefins for producing saturated silanes, or alkynes for producing unsaturated silanes, or ketones for producing silyl ethers, or trialkylsilyl-cyanation of aldehydes (e.g. benzaldehyde) for producing cyanohydrin trialkylsilyl ethers (which may afterwards be hydrolysed into cyanohydrins) can be carried out in accordance with conventional procedures (including temperature, time and substrate/catalyst ratio) known in the art. For example, optically active silanes or silyl ethers can be prepared by reacting a prochiral olefin or ketone or aldehyde together with a suitable silyl compound under conventional hydrosilylation conditions in the presence of an optically active metal complex catalytic system described herein.

Catalytic aziridination of imines or alkenes for producing organic compounds having one or more aziridine structural units can be carried out in accordance with conventional procedures (including temperature, time and substrate/catalyst ratio) known in the art. For example, prochiral olefins can be converted to optically active aziridines under conventional aziridanation conditions in the presence of an optically active metal complex catalytic system as described herein.

Catalytic hydroamidation of olefins for producing saturated amides can be carried out in accordance with conventional procedures (including temperature, time and substrate/catalyst ratio) known in the art. For example, optically active amides can be prepared by reacting a prochiral olefin, carbon monoxide, and a primary or secondary amine or ammonia under conventional hydroamidation conditions in the presence of an optically active metal complex catalytic system as described herein.

Catalytic hydrogenation of olefins into alkanes, or ketones into alcohols can be carried out in accordance with conventional procedures (including temperature, time and substrate/catalyst ratio) known in the art. For example, a ketone can be converted to an optically active alcohol under conventional hydrogenation conditions in the presence of an optically active metal complex catalytic system as described herein. Substrates that can be hydrogenated in accordance with this embodiment of the invention include, but are not limited to, α-(acylamino) acrylic acids (thus enantioselectively providing chiral amino-acids), α-acetamidocinnamic acid, α-benzamidocinnamic acid, dehydroamino acid derivatives and methyl esters thereof, imines, β-ketoesters (such as methyl acetylacetate) and ketones.

Catalytic aminolysis (hydroamination) of olefins, e;g. by means of ammonia, for producing saturated primary or secondary amines can be carried out in accordance with conventional procedures (including temperature, time and substrate/catalyst ratio) known in the art. For example, ethylene may be converted into ethylamine, or optically active amines can be prepared by reacting a prochiral olefin with a primary or secondary amine under conventional aminolysis conditions in the presence of an optically active metal complex catalytic system as described herein.

Catalytic isomerization of alcohols, preferably allylic alcohols, for producing aldehydes can be carried out in accordance with conventional procedures (including temperature, time and substrate/catalyst ratio) known in the art. For example, allylic alcohols can be isomerized under conventional isomerization conditions to produce optically active aldehydes in the presence of an optically active metal complex catalytic system described herein.

Catalytic Grignard cross coupling of alkyl or aryl halides for producing alkanes or arylalkanes can be carried out in accordance with conventional procedures (including temperature, time and substrate/catalyst ratio) known in the art. For example, optically active alkanes or arylalkanes can be prepared by reacting a chiral Grignard reagent with an alkyl or aryl halide under conventional Grignard cross coupling conditions in the presence of an optically active metal complex catalytic system as described herein.

Catalytic hydroboration of olefins (such as, but not limited to, 4-methyl-1-pentene) for producing alkylboranes and trialkylboranes (which may then be oxidised or hydrolysed into alcohols) can be carried out in accordance with conventional procedures (including temperature, time and substrate/catalyst ratio) known in the art. For example, optically active alkyl boranes or alcohols can be prepared by reacting a prochiral olefin and a borane under conventional hydroboration conditions in the presence of an optically active metal complex catalytic system as described herein.

Catalytic hydride reduction of aldehydes and ketones for producing alcohols can be carried out in accordance with conventional procedures (including temperature, time and substrate/catalyst ratio) known in the art, i.e. by treating the said aldehyde or ketone with a hydride reagent such as sodium borohydride or alithium aluminum hydride. For example, pentanal may be reduced into 1-pentanol, cyclobutanone into cyclobutanol, and cyclohexane-1,4-dione into 1,4-cyclohexanediol.

Catalytic aldol condensation of saturated carboxyl compounds (aldehydes or ketones) for producing α,β-unsaturated carboxyl compounds or β-hydroxycarbonyl compounds, and intra-molecular aldol condensation of dialdehydes or diones for producing cyclic α,β-unsaturated carboxyl compounds (aldehydes or ketones) can be carried out in accordance with conventional procedures (including temperature, time and substrate/catalyst ratio) known in the art. For example, optically active aldols can be prepared by reacting a prochiral ketone or aldehyde and a protected enol such as a silyl enol ether under conventional aldol condensation conditions in the presence of an optically active metal complex catalytic system as described herein.

Catalytic codimerization of alkenes for producing higher saturated hydrocarbons or alkynes for producing higher alkenes can be carried out in accordance with conventional procedures (including temperature, time and substrate/catalyst ratio) known in the art. For example, optically active hydrocarbons can be prepared by reacting a prochiral alkene and another alkene under codimerization conditions in the presence of an optically active metal complex catalytic system as described herein.

Catalytic alkylation, preferably allylic alkylation, of ketones for producing alkylated ketones, preferably allylic ketones, can be carried out in accordance with conventional procedures (including temperature, time and substrate/catalyst ratio) known in the art in the presence of a metal complex catalytic system as described herein. Similarly, 1,3-diphenyl-2-propenyl acetate may be alkylated with a nucleophile such as $CH_2(CO_2CH_3)_2$ in the presence of the catalytic component of the invention.

Catalytic Diels-Alder reactions such as, but not limited to, the cycloaddition of a conjugated diene onto an optionally substituted α-ethylenically unsaturated compound (the dienophile) for producing optionally substituted cyclohexenes, or the cycloaddition of furan onto an optionally substituted α-ethylenically unsaturated compound for producing optionally substituted 7-oxanorbornenes can be carried out in accordance with conventional procedures (including temperature, time and substrate/catalyst ratio) known in the art in the presence of a metal complex catalytic system as described herein.

Catalytic Michael addition of a ketone or a β-dicarbonyl compound onto an α,β-unsaturated carboxyl compound for producing saturated polycarboxyl compounds can be carried out in accordance with conventional procedures (including temperature, time and substrate/catalyst ratio) known in the art in the presence of a metal complex catalytic system as described herein, i.e. for example an enolate ion may undergo conjugate addition to an α,β-unsaturated aldehyde or ketone, such as for example the addition of acrolein onto 2,4-pentanedione (acetylacetone) or 2-methylcyclohexanone. With some Michael acceptors, such as 3-buten-2-one, the products of the initial addition are capable of a subsequent intramolecular aldol condensation, the so-called Robinson annelation, e.g. the addition of 3-buten-2-one onto 2-methylcyclohexanone.

Catalytic Heck reactions can be carried out in accordance with conventional procedures (including temperature, time and substrate/catalyst ratio) known in the art in the presence of a metal complex catalytic system as described herein. The standard Heck reaction, especially with the metal of the catalytic component being palladium, involves the reaction of an aryl or heteroaryl halide, e.g. 3-bromoquinoline, with an alkene, commonly an acrylate. An oxidative variant of the Heck reaction proceeds from certain heterocyclic compounds such as indoles, furans and thiophenes such as, but not limited to, N-acetyl-3-methylindole. A reductive variant of the Heck reaction proceeds from certain 3-acylpyridines, 4-acylpyridines and acylindoles, e.g. the reaction of 3-acetylpyridine with triethoxysilylethylene.

The permissible prochiral and chiral starting material reactants encompassed by the processes of this invention are, of course, chosen depending on the particular synthesis and product desired. Such starting materials are well known in the art and can be used in conventional amounts in accordance with conventional methods. Illustrative starting material reactants include, for example, aldehydes (e.g. for intramolecular hydroacylation, aldol condensation, and oxidation into acids), prochiral olefins (e.g. for epoxidation, hydrocyanation, hydrosilylation, aziridination, hydroamidation, aminolysis, cyclopropanation, hydroboration, Diels-Alder reaction and codimerization), ketones (e.g. for hydrogenation, hydrosilylation, aldol condensation, Robinson annelation, transfer hydrogenation and allylic alkylation), alkynes (e.g. for cyclopropenation), epoxides (e.g. for hydrocyanation or nucleophilic ring opening reaction), alcohols (e.g. for carbonylation), aryl halides (e.g. for decarbonylation and Heck reactions), and chiral Grignard reagents (e.g. for Grignard cross coupling).

As previously mentioned, for the purpose of easier removal of the catalytic compound from the reaction medium, this invention also provides a dendrimeric material comprising two or more compounds selected from five-coordinate metal complexes having any of the general formulae (IA), (IB), (IIA), (IIB) and four-coordinate metal complexes having any of the general formulae (IIIA) and (IIIB) previously described, each being attached to a core molecule (which is not to be confused with the carrier present in the supported catalyst embodiment of the invention), either directly or indirectly via a spacer molecule, by means of their N and/or or Z atoms and/or, when one of R', R" and R'" (or R" and R'" grouped together) bears a functional group, by means of the said functional group.

The core molecule is not critical to this aspect of the invention and is only limited by its reactivity with the metal carbene compound of interest or, when a spacer molecule is present in the dendrimeric material, with the said spacer molecule. For instance, the core molecule may be suitably selected from the group consisting of:

aryl, polyaryl, heteropolyaryl, alkyl, cycloalkyl and heterocycloalkyl radicals, and groups having the formula $A(R_{20})_nX_{3-n}$, wherein $R_{20}$ is a radical selected from the group consisting of $C_{1-6}$ alkylene, arylene, heteroarylene and $C_{3-8}$ cycloalkylene, the said radical being optionally substituted with one or more $R_{24}$ substituents each independently selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy, $C_{2-20}$ alkoxycarbonyl, $C_{1-20}$ alkylsulfonyl, $C_{1-20}$ alkynylsulfinyl, $C_{1-20}$ alkylthio, aryloxy and aryl; A is an element of group IIIA of the Periodic Classification of Elements (preferably boron or aluminum) or nitrogen; or the formula $G(R_{20})_nX_{4-n}$, wherein G is an element of group IVA of the said Classification (preferably carbon, silicon or tin); or the formula $J(R_{20})_nX_{5-n}$, wherein J is an element of group VA other than nitrogen (i.e. preferably phosphorus, arsenic or antimony); or else the formula $E(R_{20})_nX_{2-n}$ wherein E is an element from group VIA (preferably oxygen or sulfur), wherein in each of the said formulae X is hydrogen or halogen, and organic and inorganic transition metal compounds of any metal of groups IIB, IIIB, IVB, VB, VIB, VIIB and VIIIB of the Periodic Classification of Elements, e.g. titanium tetrachloride, vanadium trichloride, zirconium tetrachloride, $C_{1-6}$ alkyl titanates, vanadates, zirconates and the like.

When a spacer molecule is used in building up the dendrimeric material of the invention, the said spacer molecule is only limited by its reactivity with both the core the molecule and the metal carbene compound. For instance it may have the general formula $R_{20}$—$(CH_2)$—D wherein $R_{20}$, n and D are as previously defined with respect to the derivative suitable for covalent bonding to a carrier.

The dendrimeric material of this invention may be produced by reacting a core molecule (such as defined hereinbefore) with two or more five- or four-coordinate metal complexes such as disclosed hereinabove, using methods standard in the art.

The dendrimeric material of this invention may thus be used as a catalyst for transforming a first olefin into at least one second olefin or into a linear olefin oligomer or polymer, the said catalyst being suitable for removal from the reaction mixture by ultra-filtration.

The present invention further provides a one-step method for the synthesis of a 1-hetero-2,4-cyclopentadiene compound from a heterodiallyl compound. In one specific embodiment of this method, said heterodiallyl compound is contacted with a bimetallic complex wherein one metal is penta-coordinated with a carbene ligand, a multidentate ligand and one or more other ligands and the other metal is tetra-coordinated with one or more neutral ligands and one or more anionic ligands. Unexpectedly this method provides not only the ring-closure metathesis into a dihydropyrrole compound (respectively a dihydrofurane or dihydrothiophene compound, depending upon the starting heterodiallyl compound) but also isomerisation and dehydrogenation of the latter into a 1-hetero-2,4-cyclopentadiene compound. The bimetallic complex which may be used is for instance as shown in the general formulae (IVA) and (IVB) referred to in FIG. 3, wherein M, Z, R', R", R''', $R_3$ and $R_4$ are as previously defined with respect to formulae (IA) and (IB), M' is a metal as defined above with respect to M (M and M' may be the same or different), $X_1$, $X_2$ and $X_3$ are anionic ligands as defined above with respect to $R_2$ and L is a neutral electron donor as defined above with respect to $R_{16}$.

1-hetero-2,4-cyclopentadiene compounds which may be produced in one step according to this method are selected from the group consisting of pyrrole, furan, thiophene and derivatives. The presence of a substituent on the heteroatom, when the latter is nitrogen, does not prevent the unexpected reaction to take place. In particular certain new pyrrole derivatives, such as dialkyl 1H-pyrrole-1-yl methyl phosphonate wherein the alkyl group has from 1 to 4 carbon atoms, may be produced in such a way from novel dialkyl diallylaminomethyl phosphonates wherein the alkyl group has from 1 to 4 carbon atoms, as illustrated by the following examples.

More broadly, this invention relates to novel 1-hetero-2,4-cyclopentadiene compounds obtainable by the above method.

The present invention will now be further explained by reference to the following set of examples which should be understood as merely illustrating various embodiments of the invention without limiting the scope thereof.

In the first place a general procedure for preparing ruthenium compounds having the general formula (IA) according to the present invention wherein y=2 will be explained by reference to FIG. 1. First, a Schiff base ligand having the formula (I)—not to be confused with formulae (IA) and (IB) above—is prepared and purified using methods well known in the art, by condensing an aldehyde having the general formula:

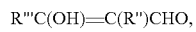

R'''C(OH)=C(R'')CHO, preferably a salicylaldehyde, with a primary amine having the formula $H_2NR'$ at reflux temperature in an organic solvent (e.g. tetrahydrofuran). After cooling, the viscous yellow oily condensation product is purified by silica gel chromatography, thus yielding the desired salicylaldimine ligand of formula (I). In a second step, the Schiff base substituted ruthenium complex having the formula (II)—not to be confused with formulae (IIA) and (IIB) above—is prepared and purified, using methods well known in the art, by adding an organic solution of a metal alkoxide, preferably thallium ethoxide, to an organic solution of the ligand of formula (I), then filtering the resulting solid under an inert atmosphere to quantitatively yield the respective thallium salt. An organic solution of the said salt was then reacted at room temperature with an organic solution of $[RuCl_2(p\text{-cumene})]_2$. After filtering the thallium chloride by-product and evaporating the solvent, the residue was crystallized, washed and dried, thus resulting in the Schiff base ruthenium complex having the formula (II) appearing as a red-brownish solid.

Before performing the third step, an organic solution of the tert-butoxylated compound having the formula (III)—not to be confused with formulae (IIA) and (IIB) above—, wherein "mes" is an abbreviation standing for 2,4,6-trimethylphenyl, is prepared by adding an organic solution of potassium tert-butoxide to an organic solution of 1,3-bis(2,4,6-trimethylphenyl)-4,5-dihydroimidazolium tetrafluoroborate at room temperature, and then filtering off the potassium tetrafluoroborate by-product under inert atmosphere. A mixture of an organic solution of the complex of the formula (II) and an organic solution of the tert-butoxylated compound having the formula (III) was heated at 70-80° C. for one hour. After evaporating the solvent, the solid residue was washed, recrystallized and dried under vacuum, thus resulting in the pure Schiff base substituted ruthenium complex having the formula (IV) as a brown microcrystalline solid. A pure Schiff base substituted allenylidene complex having the formula (V) is obtained as a dark brownish microcrystalline solid in a fourth step by adding an organic solution of the complex having the formula (IV) to an organic solution of diphenyl propargyl alcohol, stirring the mixture for 17 hours at room temperature, evaporating the solvent in vacuo, and then recrystallizing the remaining solid residue.

Following an alternative synthetic route, a Schiff base substituted indenylidene complex having the formula (VI) is obtained as a red-brownish microcrystalline solid by adding an organic solution of a ruthenium complex having the formula (II) to an organic solution of diphenyl propargyl alcohol, stirring the mixture for 17 hours at room temperature, evaporating the solvent in vacuo, and then recrystallizing the remaining solid residue. Then a Schiff base substituted ruthenium complex having the formula (VII) is prepared by first adding an organic solution of the tert-butoxylated compound having the formula (III) to an organic solution of the Schiff base substituted indenylidene complex having the formula (VI) and stirring the mixture for one hour at 70-80° C. After evaporating the solvent, the solid residue was washed, recrystallized and subsequently dried under vacuum, thus resulting in the pure compound of the formula (VII) as a red-brownish microcrystalline solid.

Secondly, a general procedure for preparing ruthenium compounds having the general formula (IC) according to the present invention wherein y=2 will be explained by reference to FIG. 2. First, a Schiff base ligand having the formula (I) and its thallium salt are prepared as above. Separately, a dichlorodicyclohexylphosphino vinylidene ruthenium complex is prepared by reacting $[RuCl_2(p\text{-cumene})]_2$ in a solvent with both dicyclohexylphosphine and a substituted acetylene at 70° C. Then, a solution of the resulting dark-brown microcrystalline solid is in turn reacted with the Schiff base thallium salt prepared above.

Although the various synthetic routes shown in the appended FIGS. 1 and 2 have been described herein with respect to ruthenium complexes, the skilled person will be able to produce the corresponding complexes from other transition metals, such as osmium, iron, molybdenum, tungsten, titanium, rhenium, copper, chromium, manganese, rhodium, vanadium, zinc, gold, silver, nickel and cobalt, while making use of the above teaching and starting from the relevant metal complexes corresponding to $[RuCl_2(p\text{-cumene})]_2$ and analogues thereof.

EXAMPLE 1

Preparation of the Schiff Base Ligands of Formulae (I.a) to (I.f)

Schiff base ligands having the formulae (I.a) to (I.f), wherein R and R' have the meanings indicated at the bottom of the appended figure and wherein Me stands for methyl while iPr stands for isopropyl, were prepared and purified as follows. Condensation of a salicylaldehyde with a primary aliphatic amine (i.e. R' being an aliphatic or cycloaliphatic radical) was carried out with stirring in tetrahydrofuran (hereinafter referred as THF) at reflux temperature for 2 hours.

After cooling to room temperature, the viscous yellow oily condensation product was purified by silica gel chromatography and the desired salicylaldimine ligands—having formulae (I.a) and (I.b)—were obtained in yields of 95% and 93% respectively. Condensation of a salicylaldehyde with an aromatic primary amine was similarly carried out with stirring in ethanol at 80° C. for 2 hours. Upon cooling to 0° C., a yellow solid precipitated from the reaction mixture. This solid was filtered, washed with cold ethanol and then dried in vacuo to afford the desired salicylaldimine ligands - having formulae (I.c) to (I.)—in yields ranging from 90% to 93%. These ligands can be stored for months in a desiccator without suffering from physico-chemical alteration.

Compound (I.a-d) were characterized by means of proton nuclear magnetic resonance (hereinafter referred as NMR) spectophotometry (performed on $CDCl_3$ at 25° C.) and infrared spectrophotometry (IR), the results of such analysis being as follows:

Compound (I.a): a yellow liquid; $^1$H-NMR ($CDCl_3$) δ 12.96 (s, 1H), 8.75 (s, 1H), 7.50 (d, 1H), 7.15 (d, 1H), 7.27 (t, 1H), 6.78 (t, 1H) and 3.30 (d, 3H); $^{13}$C-NMR ($CDCl_3$) δ 166.4, 161.7, 137.0, 133.8, 120.8, 119.9, 118.4 and 45.9; IR (cm$^{-1}$) 3325 ($v_{OH}$, br), 3061 ($v_{CH}$, w), 2976 ($v_{HC=N}$, w), 2845-2910 ($v_{CH3}$, br), 1623 ($v_{C=N}$, s), 1573 ($v_{C=C(Ph)}$, w), 1525 ($v_{C=C(Ph)}$, w), 1497 ($v_{C=C(Ph)}$, w), 1465 ($v_{C=C(Ph)}$, w), and 1125 ($v_{CO}$, br).

Compound (I.b): a yellow liquid; $^1$H-NMR ($CDCl_3$) δ 13.18 (s, 1H), 8.98 (s, 1H), 8.10 (d, 1H), 8.03 (d, 1H), 7.67 (d, 1H) and 3.41 (d, 3H); $^{13}$C-NMR ($CDCl_3$) δ 168.2, 164.3, 143.4, 137.9, 134.7, 123.1, 120.8 and 49.4; IR (cm$^{-1}$) 3329 ($v_{OH}$, br), 3067 ($v_{CH}$, w), 2986 ($v_{HC=N}$, w), 2840-2912 ($v_{CH3}$, br), 1618 ($v_{C=N}$, s), 1570 ($v_{NO2}$, s), 1546 ($v_{C=C(Ph)}$, w), 1524 ($v_{C=C(Ph)}$, w), 1492 ($v_{C=C(Ph)}$, w), 1465 ($v_{C=C(Ph)}$, w), 1329 ($v_{NO2}$, s) and 1133 ($v_{CO}$, br).

Compound (I.c): a yellow solid; $^1$H-NMR ($CDCl_3$) δ 12.85 (s, 1H); 8.32 (s, 1H), 7.45 (d, J=7.0 Hz, 1H), 7.30 (t, J=7.1 Hz, 1H), 7.03 (s, 2H), 6.99 (t, J=7.3 Hz, 1H), 6.84 (d, J=6.9 Hz, 1H) and 2.21 (s, 6H); $^{13}$C-NMR ($CDCl_3$) δ 164.0, 160.9, 138.0, 132.4, 130.1, 129.8, 127.6, 127.1, 117.6, 117.3, 116.4 and 18.2; IR (cm$^{-1}$) 3342 ($v_{OH}$, br), 3065 ($v_{CH}$, w), 3031 ($v_{CH}$, w), 2850-2925 ($v_{CH3}$, br), 1620 ($v_{C=N}$, s), 1569 ($v_{C=C(Ph)}$, w), 1523 ($v_{C=C(Ph)}$, w), 1491($v_{C=C(Ph)}$, w), 1467 ($v_{C=C(Ph)}$, w) and 1093 ($v_{CO}$, br).

Compound (I.d): a yellow solid; $^1$H-NMR ($CDCl_3$) δ 13.93 (s, 1H), 8.43 (s, 1H), 8.33 (d, J=3 Hz, 1H), 8.29 (d, J=9 Hz, 1H), 7.26 (s, 2H), 7.12 (d, J=9 Hz, 1H) and 2.18 (s, 6H); $^{13}$C-NMR ($CDCl_3$) δ 166.2, 165.3, 145.5, 139.9, 131.2, 130.2, 128.7, 128.5, 118.5, 118.0, 117.4 and 18.1; IR (cm$^{-1}$) 3337 ($v_{OH}$, br), 3068 ($v_{CH}$, w), 3036 ($v_{CH}$, w), 2848-2922 ($v_{CH3}$, br), 1626 ($v_{C=N}$, s), 1567($v_{NO2}$, s), 1548 ($v_{C=C(Ph)}$, w), 1527 ($v_{C=C(Ph)}$, w), 1494 ($v_{C=C(Ph)}$, w), 1467 ($v_{C=C(Ph)}$, w), 1334 ($v_{NO2}$, s) and 1096 ($v_{CO}$, br).

EXAMPLE 2

Preparation of Schiff Base Substituted Ruthenium Complexes of Formulae (II.a) to (II.f)

Schiff base substituted ruthenium complexes having formulae (II.a) to (II.f) as shown in the appended figure were prepared in two steps and purified as follows. In a first step, to a solution in THF (10 ml) of the appropriate Schiff base of formula (I.a) to (I.f) prepared according to example 1, a solution of thallium ethoxide in THF (5 ml) was added dropwise at room temperature. Immediately after addition, a pale yellow solid formed and the reaction mixture was stirred for 2 hours at 20° C. Filtrabon of the solid under an argon atmosphere provided the respective salicylaldimine thallium salt in quantitative yield, which was immediately used in the next step without further purification.

To a solution of the said salicylaldimine thallium salt in THF (5 ml) was added a solution of [RuCl$_2$(p-cymene)]$_2$ in THF (5 ml), then the reaction mixture was stirred at room temperature (20° C.) for 6 hours. The thallium chloride by-product was removed via filtration. After evaporation of the solvent, the residue was dissolved in a minimal amount of toluene and cooled to 0° C. The crystals obtained were then washed with cold toluene (3×10 ml) and dried, resulting in the Schiff base ruthenium complexes of formulae (II.a) to (II.f) as red-brownish solids.

EXAMPLE 3

Preparation of Schiff Base Substituted Ruthenium Complexes of Formulae (IV.a) to (IV.f)

After adding 1 equivalent of a potassium tert-butoxide solution in THF (5 ml) to a solution of 1,3-bis(2,4,6-trimethylphenyl)-4,5-dihydroimidazolium tetrafluoroborate in THF (10 ml), and stirring the reaction mixture for 5 minutes at room temperature (20° C.), the potassium tetrafluoroborate by-product was filtered off under inert atmosphere and the t-butoxylated compound having formula (III) appeared in quantitative yield. After evaporation of the solvent, compound (III) was dissolved in toluene (10 ml) and immediately used in the next step without further purification. After addition of 1 equivalent of a solution of the appropriate Schiff base substituted ruthenium complex having one of formulae (II.a) to (II.f), prepared according to example 2, in toluene (10 ml), heating the reaction mixture at 70-80° C. was effected for one hour under vigorous stirring. After evaporation of the solvent, the solid residue was washed with hexane (3×10 ml) and recrystallized from a toluene/pentane mixture at 0° C. Subsequent drying under vacuum resulted in the formation of the pure Schiff base substituted ruthenium complexes of formulae (IV.a) to (IV.f) as brownish microcrystalline solids in yields ranging between 90% and 95%.

EXAMPLE 4

Preparation of Schiff Base Substituted Ruthenium Complexes of Formulae (V.a) to (V.f)

Schiff base substituted allenylidene compounds having the formulae (V.a) to (V.f) were obtained by adding a solution of the appropriate Schiff base substituted ruthenium complex having one of formulae (IV.a) to (IV.f), prepared according to example 3, in toluene (15 ml) to 1.2 equivalents of a solution of the commercially available diphenyl propargyl alcohol in toluene (5 ml), and then stirring the reaction mixture for 17 hours at room temperature (20° C.). Toluene was evaporated in vacuo and the remaining solid residue was recrystallized from a dichloromethane/hexane mixture and washed with hexane (3×10 ml) to provide the desired compounds as dark brown microcrystalline solids in yields ranging between 80% and 90%.

EXAMPLE 5

Preparation of Schiff Base Substituted Ruthenium Complexes of Formulae (VI.a) to (VI.f)

Schiff base substituted indenylidene complexes of formulae (VI.a) to (VI.f) were obtained by adding a solution of the appropriate Schiff base substituted ruthenium complex having one of formulae (II.a) to (II.f), prepared according to example 2, in toluene (15 ml) to 1.2 equivalents of a solution of the commercially available diphenyl propargyl alcohol in toluene (5 ml), and then stirring the reaction mixture for 17 hours at room temperature (20° C.). Toluene was evaporated in vacuo and the remaining solid residue was recrystallized from a dichloromethane/hexane mixture and washed with hexane (3×10 ml) to provide the desired compounds as red-brownish microcrystalline solids in yields higher than 70%.

EXAMPLE 6

Preparation of Schiff Base Substituted Ruthenium Complexes of Formulae (VII.a) to (VII.f)

To a solution of the appropriate Schiff base substituted ruthenium complex having one of formulae (VI.a) to (VI.f), prepared according to example 5, in toluene (10 ml) was added 1 equivalent of a solution of the t-butoxylated compound having formula (III), as prepared in example 3, in toluene (10 ml). Vigorous stirring of the reaction mixture was then effected for one hour at 70-80° C. After evaporation of the solvent, the solid residue was washed with hexane (3×10 ml) and recrystallized from a dichloromethane/hexane mixture. Subsequent drying under vacuum resulted in the formation of the pure compounds of formulae (VII.a) to (VII.f) as red-brownish microcrystalline solids in quantitative yield.

EXAMPLE 7

Ring Opening Metathesis Polymerisation

Ring opening metathesis polymerisation of various cyclic olefins was performed in 1 ml toluene as a solvent while using 0.005 mmole of the Schiff base substituted allenylidene compound having the formula (V.a) prepared in example 4 as the catalyst. The following table 1 indicates the name of the olefin monomer, molar ratio olefin/catalyst, polymerisation temperature T (expressed in ° C.) and polymerisation time t (expressed in minutes) and also provides the polymerisation yield at time t (expressed in %).

TABLE 1

| Monomer | Ratio | T ° C. | t | yield |
|---|---|---|---|---|
| norbornene | 2,000 | 20 | 2 | 100 |
| butylnorbornene | 2,000 | 20 | 2 | 100 |
| hexylnorbornene | 2,000 | 20 | 2 | 100 |
| decylnorbornene | 2,000 | 20 | 2 | 100 |
| ethylidenenorbornene | 2,000 | 80 | 60 | 100 |
| Phenylnorbornene | 2,000 | 80 | 60 | 100 |
| cyclohexenylnorbornene | 2,000 | 80 | 60 | 100 |
| ethyltetracyclododecene | 2,000 | 80 | 60 | 100 |
| chloromethylnorbornene | 2,000 | 80 | 60 | 100 |
| triethoxysilylnorbornene | 2,000 | 80 | 60 | 100 |
| Tetrahydroindenylnorbornene | 2,000 | 80 | 60 | 100 |
| cyanonorbornene | 800 | 80 | 240 | 100 |
| hydroxymethylnorbornene | 800 | 80 | 240 | 100 |
| vinylnorbornene | 800 | 80 | 120 | 100 |
| cyclopentene | 800 | 20 | 3 | 100 |
| cyclooctene | 80,000 | 80 | 240 | 100 |
| cyclooctene | 80,000 | 20 | 240 | 58 |
| cyclooctene | 80,000 | 4 | 1,440 | 31 |
| cyclooctene | 300,000 | 80 | 240 | 92 |
| cyclooctene | 300,000 | 20 | 240 | 36 |
| 3,4-epoxycyclooctene | 800 | 80 | 120 | 100 |
| 5,6-epoxycyclooctene | 800 | 80 | 120 | 34 |
| Polyethyleneglycolnorbornene | 800 | 80 | 120 | 92 |

EXAMPLE 8

Ring Closing Metathesis Reaction

The ring closing metathesis reaction of various dienes was performed in 1 ml deuterated benzene as a solvent (except for diallylamine hydrochloride, for which the solvent used was deuterated methanol), while using:
 0.005 mmole of the Schiff base substituted allenylidene compound having the formula (V.a) prepared in example 4 as the catalyst, and
 a molar ratio diene/catalyst equal to 100.

The following table 2 indicates the name of the diene involved, the reaction temperature T (expressed in ° C.), the reaction time t (expressed in minutes) and also provides the reaction yield at time t (expressed in %) and the name of the resulting product.

TABLE 2

| Diene | T° C. | t | Yield - product obtained |
|---|---|---|---|
| 1,7-octadiene | 20 | 60 | 100% hexene-1 |
| diethyldiallylmalonate | 20 | 60 | 100% 4,4-dicarbethoxycyclopentene |
| diallylether | 20 | 60 | 100% 3,4-dihydrofurane |
| diallylphtalate | 65 | 240 | 96% 1,2-benzene dicarboxylic acid cyclobut-2-ene ester |
| linalool | 65 | 240 | 91% 4-hydroxy-4-methylcyclopentene |
| diallylamine hydrochloride | 20 | 240 | 84% 3,4-dihydropyrrole hydrochloride |
| 4,4-dicarbethoxy-2-methyl-1,6-heptadiene | 20 | 360 | 81% 4,4-dicarbethoxy-methylcyclopentene |
| 4,4-dicarbethoxy-2,6-dimethyl-1,6-heptadiene | 20 | 360 | 72% 4,4-dicarbethoxy-1,2-dimethyl cyclopentene |

EXAMPLE 9

Atom Transfer Radical Polymerisation

The atom transfer radical polymerisation of various olefins was performed in 1 ml toluene during 8 hours at the temperature (expressed in ° C.) indicated below and while using:
 as a catalyst, 0.0116 mmole of the Schiff base substituted allenylidene ruthenium complex having the formula (V.a) as prepared in example 4,
 as an initiator, ethyl-2-methyl-2-bromopropionate (when the monomer is a methacrylate), methyl-2-bromopropionate (when the monomer is an acrylate), 1-bromocyanoethane (when the monomer is acrylonitrile) or (1-bromoethyl)benzene (when the monomer is styrene), and
 a molar ratio [catalyst]/[initiator]/[monomer] equal to 1:2:800.

The following table 3 indicates the name of the olefin involved, the polymerisation temperature and the polymerisation yield (expressed in %).

TABLE 3

| Olefin | Yield | Temperature |
|---|---|---|
| methylmethacrylate | 97 | 85 |
| isobutylmethacrylate | 35 | 85 |
| methylacrylate | 84 | 85 |
| butylacrylate | 62 | 85 |
| acrylonitrile | 26 | 65 |
| styrene | 98 | 110 |

EXAMPLE 10

Atom Transfer Radical Polymerisation in Water

The atom transfer radical polymerisation of various olefins was performed in water as a solvent, while using:
- as a catalyst, 0.0116 mmole of the Schiff base substituted allenylidene compound having the formula (V.a) prepared in example 4, which has been treated with 1 equivalent of silver tetrafluoroborate (more specifically, the above amount of compound (V.a) was added to 1 ml toluene and 56 µl of a 0.2 M $AgBF_4$ solution in toluene, then stirred during 20 minutes until a turbidity of AgCl is detected, thus resulting in a cationic ruthenium complex wherein the chloride ligand was abstracted and replaced by toluene), and
- the same initiators as already mentioned in example 9, and a [catalyst]/[initiator]/[monomer] molar ratio equal to 1:2:800, at the temperature indicated in the table below and during 8 hours. The catalyst and the initiator are dissolved in toluene, the volume ratio toluene:water being 1:1. The following table 4 indicates the name of the olefin involved, the polymerisation temperature and the polymerisation yield (expressed in %).

TABLE 4

| Olefin | Yield | Temperature |
|---|---|---|
| methylmethacrylate | 73 | 85 |
| isobutylmethacrylate | 17 | 85 |
| methylacrylate | 70 | 85 |
| butylacrylate | 34 | 85 |
| acrylonitrile | 16 | 65 |
| styrene | 76 | 85 |

EXAMPLE 11

Atom Transfer Radical (co)polymerisation of Vinyl Monomers

The atom transfer radical polymerisation and copolymerisation of various vinyl monomers was performed while using:
- the same initiators as already used in example 9, and
- as a catalyst, a ruthenium carbene complex (A.a) to (A.f), being a compound previously disclosed as an olefin metathesis catalyst by Chang et al. in *Organometallics* (1998) 17:3460 and having one of the formulae:

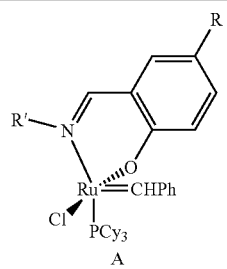

A
- a. R = H, R' = Me
- b. R = $NO_2$, R' = Me
- c. R = H, R' = 2,6-Me—4-$BrC_6H_2$
- d. R = $NO_2$, R' = 2,6-Me—4-$BrC_6H_2$
- e. R = H, R' = 2,6-$iPrC_6H_3$
- f. R = $NO_2$, R' = 2,6-$iPrC_6H_3$ wherein Cy stands for cyclohexyl, Ph stands for phenyl, Me stands for methyl and iPr stands for isopropyl.

A typical procedure for this purpose is as follows: polymerisation was carried out under argon atmosphere in a sealed glass vial. 0.0117 mmole of the catalyst was placed in a glass tube (in which the air was expelled by three vacuum-nitrogen cycles) containing a magnet bar and capped by a three-way stopcock. Then the monomer and initiator were added so that the molar ratios [catalyst]/[initiatory]/[monomer] were 1/2/800. All liquids were handled under argon with dried syringes. The reaction mixture was then heated for 17 hours at a reaction temperature of 85° C. (for (meth)acrylates) or 110° C. (for styrene). After cooling, it was diluted in THF and poured in 50 ml n-heptane (for (meth)acrylates) or 50 ml methanol (for styrene) under vigorous stirring. The precipitated polymer was then filtered and dried in vacuum overnight.

Table 5 below indicates the polymerisation yield as a function of the monomer and the catalytic ruthenium complex being used.

TABLE 5

| Monomer | A.a | A.b | A.c | A.d | A.e | A.f |
|---|---|---|---|---|---|---|
| methyl methacrylate | 5 | 5 | 11 | 28 | 7 | 10 |
| isobutyl methacrylate | 5 | 5 | 9 | 19 | 5 | 7 |
| methyl acrylate | 5 | 5 | 12 | 26 | 8 | 9 |
| butyl acrylate | 5 | 5 | 9 | 16 | 5 | 7 |
| styrene | 10 | 16 | 74 | 88 | 56 | 65 |

Table 6 indicates the weight average molecular weight $M_w$, the number average molecular weight $M_n$ and the polydispersity index (PDI) of homopolymers formed with a ruthenium carbene complex (A.c) to (A.f) from methyl acrylate (first figure), styrene (second figure) or methyl methacrylate (third figure) respectively.

TABLE 6

| Catalyst | $M_n(\times 10^3)$ | $M_w(\times 10^3)$ | PDI |
|---|---|---|---|
| A.c | 5.7/38/6.3 | 7.5/63/7.9 | 1.31/1.65/1.25 |
| A.d | 9.5/41/13 | 12.2/59/15.9 | 1.28/1.44/1.22 |
| A.e | 4.5/29/4.8 | 6.8/51/7.5 | 1.52/1.75/1.56 |
| A.f | 5.3/32/6.6 | 7.8/55/9.9 | 1.48/1.71/1.51 |

EXAMPLE 12

Figure 11:
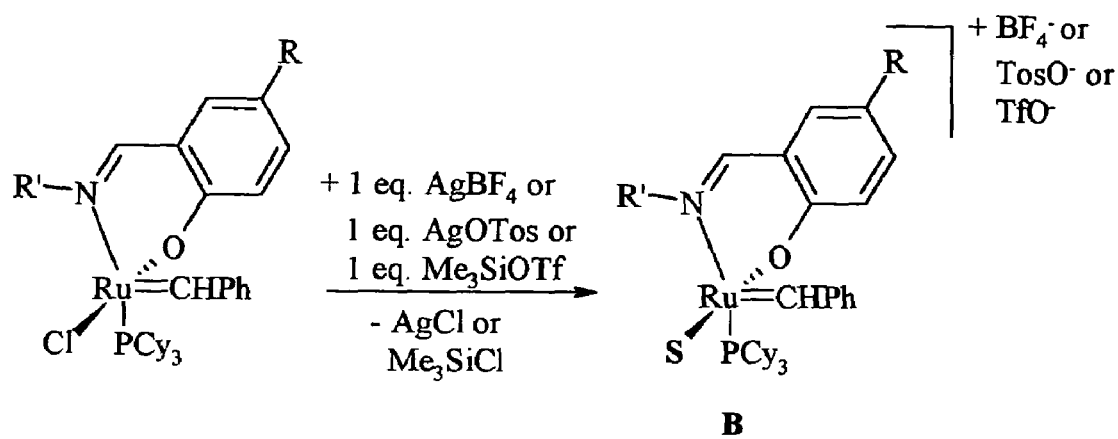
FIG. 11 schematically shows the preparation of a cationic species of a ruthenium monometallic complex of this invention.
Figure 12:
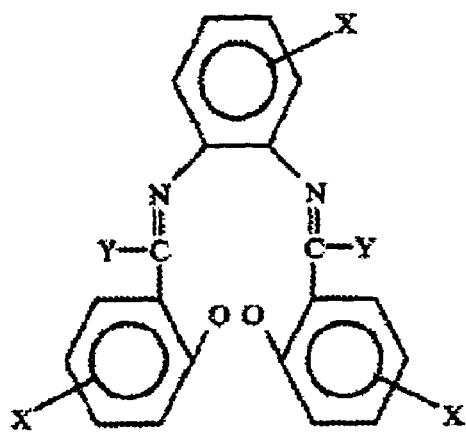
FIG. 12 schematically shows the general formulae (VA), (VB) and (VC) of tetradentate ligands having two Schiff bases that are suitable for coordination in metal complexes according to another embodiment of the present invention.
Figure 12:
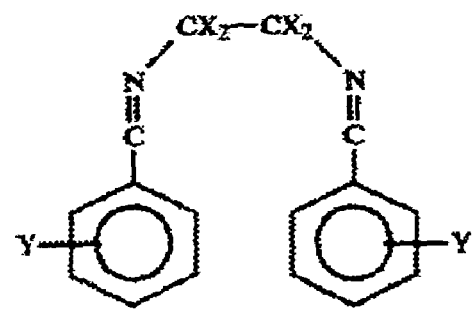
Figure 12:
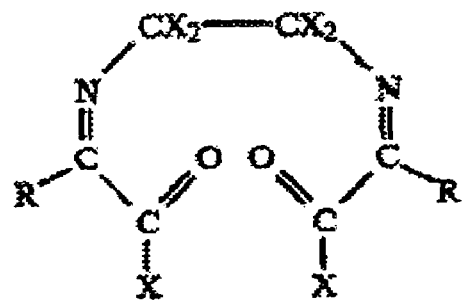
Figure 13:
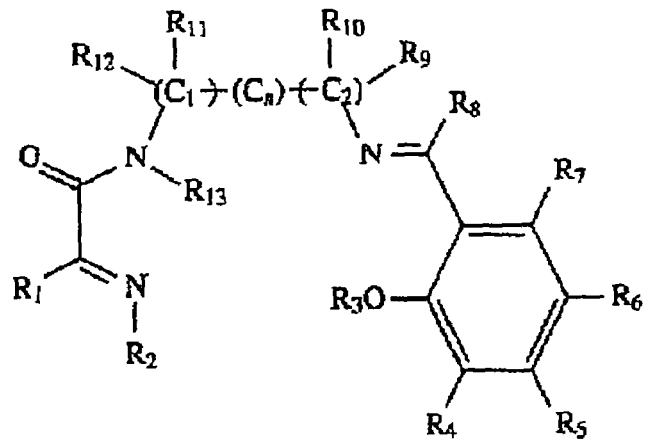
FIG. 13 schematically shows the general formulae (VIA) and (VIB) of tetradentate Schiff base ligands and the general formula (VIC) of bidentate ligands that are suitable for coordination in metal complexes according to another embodiment of the present invention.
Figure 13:
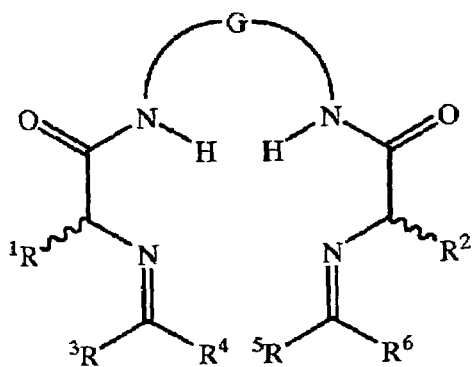
Figure 13:
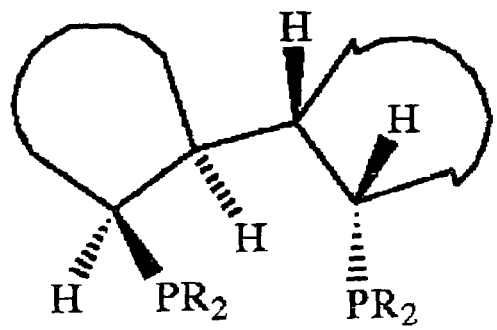
Figure 14:
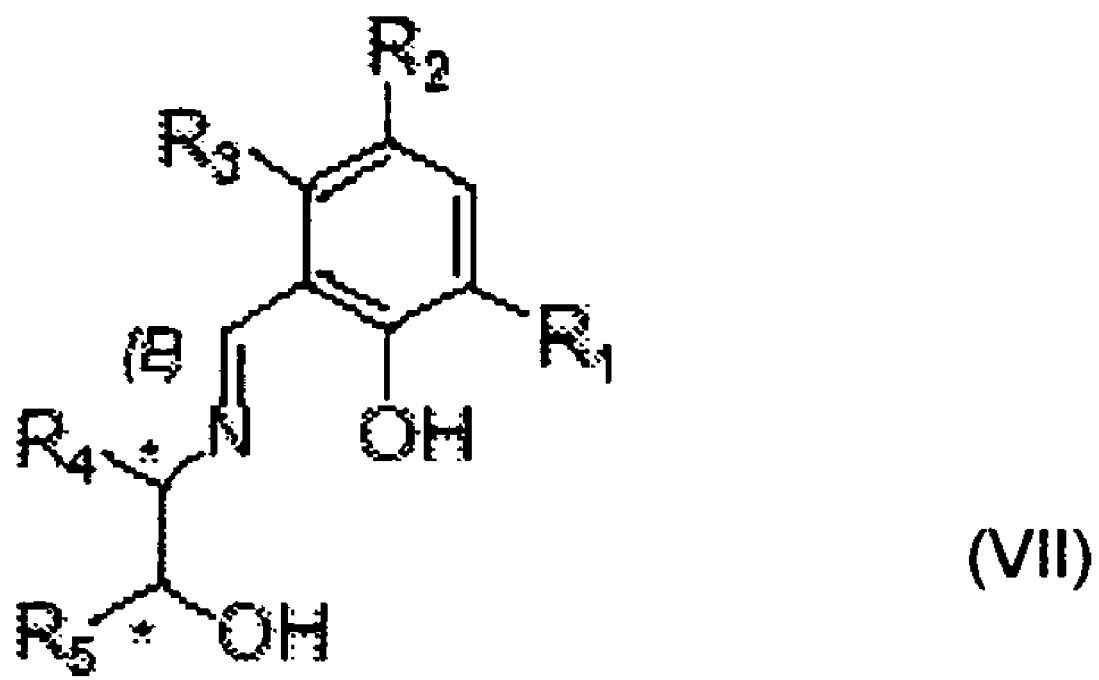
FIG. 14 schematically shows the general formula (VII) of tridentate Schiff base ligands that are suitable for coordination in metal complexes according to another embodiment of the present invention.

Atom Transfer Radical (co)polymerisation of Vinyl Monomers in the Presence of a Cationic Ruthenium Complex The atom transfer radical polymerisation and copolymerisation of various vinyl monomers was performed in a solvent S while using:
- the same initiator as already used in example 9, and
- as a catalyst, a cationic ruthenium carbene complex (B.a) to (B.f), being obtained according to the scheme shown in FIG. 11 by treating the ruthenium carbene complex of example 11, having the appropriate formula (A.a) to (A.f), with a salt in the presence of a solvent S according to the following scheme, wherein Tos is an abbreviation for tosylate (p-toluenesulfonate) and Tf is an abbreviation for triflate (trifluoro-methanesulfonate):

When toluene was used as a solvent, the monomer, the initiator and the catalyst were dissolved in a small amount of toluene so that the monomer/toluene ratio was 1/1 (volume/ volume). For suspension polymerization in water/toluene mixtures, the monomer, initiator and catalyst were dissolved in a small amount of toluene, and distilled water was added to the organic solution so that the monomer/toluene ratio was 1/3.5 (volume/volume) and the water/organic phase ratio was 1/1 (volume/volume). No dispersant or surfactant (particle stabilizer) was added to the polymerisation medium.

In order to assess the influence of the counter-ion on the catalytic activity, three different salts (silver tetrafluoroborate, silver tosylate and trimethylsilyltriflate) were used to abstract a chloride from the complexes (A.a) to (A.f).

Table 7 below indicates polymerisation yields, as a function of the monomer, solvent and cationic catalytic ruthenium complex being used, of methyl acrylate (first figure), styrene (second figure) or methyl methacrylate (third figure) respectively.

TABLE 7

| Catalyst | Methyl acrylate/Styrene/Methyl methacrylate | | | | | |
|---|---|---|---|---|---|---|
| | water | | | toluene | | |
| | AgBF$_4$ | AgOTos | Me$_3$SiOTf | AgBF$_4$ | AgOTos | Me$_3$SiOTf |
| B.a | 6/16/5 | 5/8/5 | 5/5/5 | 11/22/8 | 8/15/5 | 5/9/5 |
| B.b | 6/17/5 | 5/11/5 | 5/8/5 | 14/26/11 | 12/21/7 | 8/14/5 |
| B.c | 64/85/61 | 51/69/43 | 21/53/14 | 78/95/71 | 64/86/59 | 36/72/32 |
| B.d | 68/91/67 | 62/84/55 | 36/69/32 | 81/98/77 | 71/92/68 | 51/87/48 |
| B.e | 11/49/7 | 9/40/5 | 5/36/5 | 16/66/12 | 16/61/11 | 11/57/8 |
| B.f | 13/53/11 | 13/46/8 | 5/41/5 | 21/74/18 | 16/70/13 | 11/67/9 |

Table 8 below indicates the weight average molecular weight M$_w$ and number average molecular weight M$_n$ (both expressed in thousands) and the polydispersity index (PDI) of homopolymers formed with a cationic ruthenium carbene complex (B.b) from methyl acrylate (first figure), styrene (second figure) or methyl methacrylate (third figure) respectively.

TABLE 8

| | Methyl acrylate/Styrene/Methyl methacrylate | | | | | |
|---|---|---|---|---|---|---|
| | water | | | toluene | | |
| | AgBF$_4$ | AgOTos | Me$_3$SiOTf | AgBF$_4$ | AgOTos | Me$_3$SiOTf |
| M$_n$ | 29/46/33 | 27/41/26 | 16.5/36/18 | 42/56/46 | 39/54/43 | 28/61/32 |
| M$_w$ | 40/68/44 | 41/64/38 | 27/59/28 | 70/96/67 | 67/98/66 | 50/113/52 |
| PDI | 1.37/1.48/1.34 | 1.52/1.56/1.45 | 1.64/1.65/1.58 | 1.66/1.71/1.46 | 1.73/1.81/1.54 | 1.77/1.86/1.64 |

EXAMPLE 13

Atom Transfer Radical Addition of Vinyl Olefins

The atom transfer radical addition of carbon tetrachloride onto various vinyl olefins was performed in an organic solvent, while using the Schiff base substituted allenylidene compound having the formula (V.a), as prepared in example 4, as the catalyst. The said catalyst (0.03 mmole) was dissolved in toluene (1 ml) and subsequently added through a septum to the solution of the vinyl monomer (9 mmoles) and carbon tetrachloride (13 mmoles) in toluene (3 ml). The reaction mixture was then heated at 65° C. for 17 hours. The following table 9 indicates the name of the vinyl monomer tested and the yield (expressed in %) of the resulting chlorinated saturated addition product.

TABLE 9

| Vinyl olefin | Yield |
|---|---|
| Methyl methacrylate | 76 |
| Isobutyl methacrylate | 57 |
| Methyl acrylate | 83 |
| Butyl acrylate | 61 |
| acrylonitrile | 55 |
| styrene | 92 |

EXAMPLE 14

Preparation of Dichlorodi(tricyclohexylphosphine)vinylidene Ruthenium Complexes

To a suspension of [RuCl$_2$(p-cymene)]$_2$ (306 mg, 0.5 mmole) in toluene (17 ml) were added respectively tricyclohexylphosphine (0.617 g, 2.2 mmole) and phenylacetylene C$_6$H$_5$C≡CH (0.102 g, 1 mmole). The mixture was slowly heated to 70° C. and stirred for 24 hours. The mixture was concentrated to about 4 ml by pumping the volatile materials. Addition of 10 ml acetone and cooling to −78° C. led to the precipitation of a dark brown microcrystalline solid which was filtered off and vacuum dried. This solid, obtained with a yield of 85%, was characterized as being Cl$_2$Ru{═C═CHC$_6$H$_5$}(PCy$_3$)$_2$ by means of proton NMR spectophotometry (performed on CDCl$_3$ at 30° C.) providing the following data: δ 7.16-7.08, 6.97-6.88 (both m, 5H, phenyl), 4.65 (t, J$_{PH}$=3.3 Hz, 1H), 2.83-2.71, 2.2-2.12, 1.77-1.45, 1.28-1.01 (each m, C$_6$H$_{11}$).

A similar procedure was used for preparing Cl$_2$Ru{═C═CHterC$_4$H$_9$}(P(cyclohexyl)$_3$)$_2$, however with a molar excess of terbutylacetylene and while keeping the reaction mixture at 40° C. during the first 4 hours. The resulting ruthenium complex, obtained with a yield of 69%, was characterized by means of proton NMR spectophotometry (performed on CDCl$_3$ at 30° C.) providing the following data: δ 2.81 (t, J$_{PH}$=3.0 Hz, 1H), 2.65-2.51, 2.14-1.99, 1.86-1.53, 1.33-1.12 (each m, 66H, C$_6$H$_{11}$) and 1.01 (s, 9H).

EXAMPLE 15

Preparation of Schiff Base Vinylidene Ruthenium Complexes

To a solution of a dichlorodicyclohexylphosphine vinylidene ruthenium complex obtained in example 14 (3 mmole) in THF (5 ml) was added a solution in THF (10 ml) of a salicylaldimine thallium salt obtained at the end of the first step of example 2. This reaction mixture was stirred at 20° C. for 4 hours and thallium chloride formed was removed via filtration. The solid residue was recrystallized from pentane at −70° C. to result in a Schiff base vinylidene ruthenium complex having the formula (IC).

Four different complexes were produced according to this procedure. The complex identified as 4a in FIG. 2, i.e. wherein R is hydrogen and R$_3$ is phenyl, was recovered as a brown solid with a yield of 81% and was characterized by means of proton NMR spectophotometry (performed on $C_6D_6$ at 25° C.) providing the following data: δ 8.20 (d, J=5.2 Hz, 1H), 7.38 (d, J=7.0 Hz, 1H), 7.30 (t, J=7.2 Hz, 1H), 7.22-7.14, 6.99-6.94, 6.89-6.79 (each m, 5H), 7.13 (s, 2H), 7.06 (t, J=7 Hz, 1H), 4.36 (t, J=4.2 Hz), 2.14 (s, 3H), 1.61-1.31 (m, 20H), 1.27 (d, J=6 Hz, 3H) and 1.19 (m, 10H).

The complex identified as 4b in FIG. 2, i.e. wherein R is nitro and $R_3$ is phenyl, was recovered as a dark brown solid with a yield of 80% and was characterized by means of proton NMR spectophotometry (performed on $C_6D_6$ at 25° C.) providing the following data: δ 8.24 (d, J=2.5 Hz, 1H), 8.08 (dd, J=9 Hz, 2.4 Hz, 1H), 7.94 (d, J=5.6 Hz, 1H), 7.56 (t, J=7.5 Hz, 1H), 7.29 (d, J=9.8 Hz, 1H), 7.16 (s, 2H), 7.13-7.07 (o-H), 7.02-6.96 (p-H), 6.89-6.80 (m-H) (each m, 5H), 4.25 (t, J=5 Hz), 2.44 (q, J=11 Hz, 3H), 2.34 (s, 3H), 1.70-1.63 (bs, 20H), 1.54 (d, J=12 Hz, 3H) and 1.36-1.08 (bs, 20H).

The complex identified as 5a in FIG. 2, i.e. wherein R is hydrogen and $R_3$ is tert-butyl, was recovered as a dark brown solid with a yield of 78% and was characterized by means of proton NMR spectophotometry (performed on $C_6D_6$ at 25° C.) providing the following data: δ 8.28 (d, J=2.7 Hz, 1H), 7.42 (d, J=7.2 Hz, 1H), 7.23 (t, J=7.0 Hz, 1H), 7.06 (m, 3H), 6.74 (d, J=6.7 Hz, 1H), 2.83 (t, J=3 Hz), 1.78-1.50 (m, 23H), 1.26-1.15 (m, 10H) and 1.08 (s, 9H).

The complex identified as 5b in FIG. 2, i.e. wherein R is nitro and $R_3$ is tert-butyl, was recovered as a brown solid with a yield of 70% and was characterized by means of proton NMR spectophotometry (performed on $C_6D_6$ at 25° C.) providing the following data: δ 8.30 (d, J=2.9 Hz, 1H), 7.6 (dd, J=9, 2.3 Hz, 1H), 7.37 (d, J=5 Hz, 1H), 7.13 (s, 2H), 6.99 (d, J=9.8 Hz, 1H), 3.06 (t, J=4 Hz), 2.50 (q, J=12 Hz, 3H), 2.38 (s, 3H), 1.88-1.75 (bs, 20H), 1.60 (d, J=12.5 Hz, 3H), 1.34-25 (m, 10H) and 1.07 (s,9H).

EXAMPLE 16

Ring Opening Metathesis Polymerization of Cyclic Olefins

Ring opening metathesis polymerization of the cyclic olefins identified by a formula and a reference number from 6 to 17 in the scheme hereunder was performed according to the following procedure.

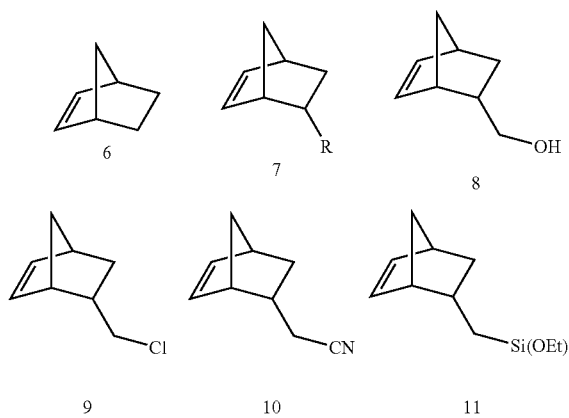

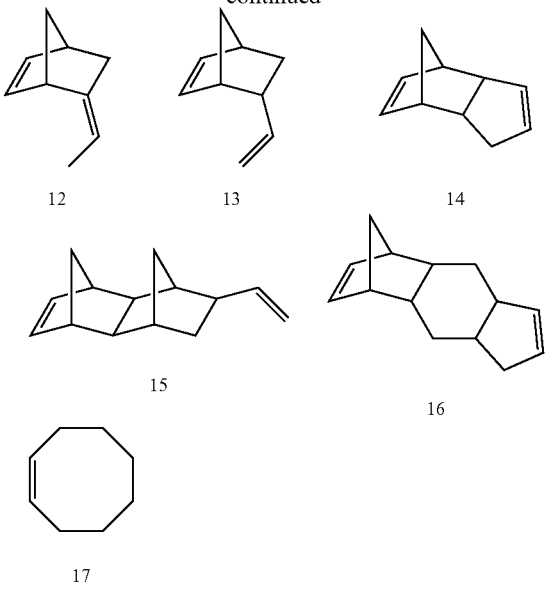

Monomer 6, i.e. norbornene (7.5 mmole), was dissolved in $CH_2Cl_2$ (2.0 ml) and admixed in a vessel with a solution of a Schiff base vinylidene ruthenium complex prepared according to example 15 (7.5 μmole) in $CH_2Cl_2$ (2 ml). Then the vessel was flushed with argon and kept at a constant temperature of 80° C. in an oil bath. After 2 hours the mixture, which became very viscous and could not be stirred anymore, was transferred into a beaker and treated with $CH_2Cl_2$ (10 ml) containing 2.6di-tert-butyl-4-methylphenol (0.4 mmole) as an oxidation inhibitor and ethylvinylether (4 mmole) as a terminating agent. The resulting solutions were stirred or one hour and, after filtration through a silica gel column, precipitated into igorously stirred methanol. The resulting white tacky polymer was filtrated, washed with methanol and dried under vacuum.

For other cyclic olefins, the experimental procedure was similar but the amount of monomer used was changed to 6 mmole (monomers 7 to 16) or 1.87 mmole (monomer 17).

The following table 10 successively indicates, after the experiment number (first column), the Schiff base vinylidene ruthenium complex used as a catalyst (using the same identification number as in example 15), the monomer reference number from 6 to 17 (followed, between brackets, by the molar monomer/catalyst ratio), polymerization temperature, time and yield, average number molecular weight $M_n$ and polydispersity $M_w/M_n$, both determined by gel permeation chromatography using polystyrene standard.

TABLE 10

| Exp. | catalyst | monomer (ratio) | temp. (° C.) | time (hours) | yield (%) | $M_n$ (×10³) | $M_w/M_n$ |
|---|---|---|---|---|---|---|---|
| 1 | 4a | 6 (1000) | 80 | 0.5 | 97 | 476 | 1.53 |
| 2 | 4b | 6 (1000) | 80 | 0.5 | 99 | 346 | 1.60 |
| 3 | 4a | 6 (1000) | 20 | 10 | 100 | 368 | 1.46 |
| 4 | 4b | 6 (1000) | 20 | 10 | 100 | 329 | 1.49 |
| 5 | 4a | 7 (800) R = ethyl | 80 | 2 | 89 | 102 | 2.66 |
| 6 | 4b | 7 (800) R = ethyl | 80 | 2 | 100 | 89 | 2.12 |
| 7 | 4a | 7 (800) R = butyl | 80 | 2 | 100 | 443 | 2.10 |

TABLE 10-continued

| Exp. | catalyst | monomer (ratio) | temp. (°C.) | time (h) | yield (%) | $M_n$ (×10³) | $M_w/M_n$ |
|---|---|---|---|---|---|---|---|
| 8 | 4b | 7 (800) R = butyl | 80 | 2 | 100 | 372 | 2.25 |
| 9 | 4a | 7 (800) R = hexyl | 80 | 2 | 82 | 257 | 1.85 |
| 10 | 4b | 7 (800) R = hexyl | 80 | | 84 | 230 | 1.87 |
| 11 | 4a | 7 (800) R = decyl | 80 | 2 | 83 | 543 | 2.44 |
| 12 | 4b | 7 (800) R = decyl | 80 | 2 | 100 | 556 | 2.54 |
| 13 | 4a | 7 (800) R = phenyl | 80 | 2 | 74 | 223 | 2.01 |
| 14 | 4b | 7 (800) R = phenyl | 80 | 2 | 80 | 209 | 1.98 |
| 15 | 4a | 7 (800) R = cyclohexenyl | 80 | 2 | 73 | 350 | 1.93 |
| 16 | 4b | 7 (800) R = cyclohexenyl | 85 | 2 | 77 | 397 | 2.33 |
| 17 | 4a | 8 (800) | 80 | 4 | 10 | 78 | 2.75 |
| 18 | 4b | 8 (800) | 80 | 4 | 16 | 65 | 2.30 |
| 19 | 4a | 9 (800) | 80 | 4 | 78 | 189 | 2.4 |
| 20 | 4b | 9 (800) | 80 | 4 | 89 | 175 | 2.31 |
| 21 | 4a | 11 (800) | 80 | 4 | 71 | 503 | 2.17 |
| 22 | 4b | 11 (800) | 80 | 4 | 79 | 479 | 2.08 |
| 23 | 4a | 12 (800) | 80 | 10 | 100 | 398 | 1.99 |
| 24 | 4b | 12 (800) | 80 | 10 | 100 | 379 | 2.03 |
| 25 | 4a | 13 (800) | 80 | 10 | 5 | — | — |
| 26 | 4a | 14 (800) | 80 | 10 | 95 | d | |
| 27 | 4b | 14 (800) | 80 | 10 | 96 | d | |
| 28 | 4a | 15 (800) | 80 | 4 | 100 | 35 | 3.21 |
| 29 | 4b | 15 (800) | 80 | 4 | 100 | 30 | 3.17 |
| 30 | 4a | 16 (800) | 80 | 10 | 100 | d | |
| 31 | 4b | 16 (800) | 80 | 10 | 100 | d | |
| 32 | 4a | 17 (250) | 80 | 15 | 10 | 347 | 1.71 |
| 33 | 4b | 17 (250) | 80 | 15 | 15 | 305 | 1.84 |

| Exp. | catalyst | monomer (ratio) | temp. (°C.) | time (h) | yield (%) | $M_n$ (×10³) | $M_w/M_n$ |
|---|---|---|---|---|---|---|---|
| 34 | 5a | 6 (1000) | 80 | 0.5 | 100 | 485 | 1.33 |
| 35 | 5b | 6 (1000) | 80 | 0.5 | 100 | 372 | 1.45 |
| 36 | 5a | 6 (1000) | 20 | 10 | 100 | 413 | 1.40 |
| 37 | 5b | 6 (1000) | 20 | 10 | 100 | 403 | 1.48 |
| 38 | 5a | 7 (800) R = ethyl | 80 | 2 | 100 | 149 | 2.64 |
| 39 | 5b | 7 (800) R = ethyl | 80 | 2 | 100 | 196 | 1.91 |
| 40 | 5a | 7 (800) R = butyl | 80 | 2 | 100 | 470 | 2.30 |
| 41 | 5b | 7 (800) R = butyl | 80 | 2 | 100 | 312 | 2.07 |
| 42 | 5a | 7 (800) R = hexyl | 80 | 2 | 95 | 227 | 1.85 |
| 43 | 5b | 7 (800) R = hexyl | 80 | | 98 | 242 | 1.76 |
| 44 | 5a | 7 (800) R = decyl | 80 | 2 | 100 | 443 | 2.09 |
| 45 | 5b | 7 (800) R = decyl | 80 | 2 | 100 | 522 | 1.80 |
| 46 | 5a | 7 (800) R = phenyl | 80 | 2 | 100 | 210 | 1.86 |
| 47 | 5b | 7 (800) R = phenyl | 80 | 2 | 100 | 224 | 1.78 |
| 48 | 5a | 7 (800) R = cyclohexenyl | 80 | 2 | 77 | 350 | 2.50 |
| 49 | 5b | 7 (800) R = cyclohexenyl | 80 | 2 | 82 | 378 | 2.60 |
| 50 | 5a | 8 (800) | 80 | 4 | 34 | 89 | 2.84 |
| 51 | 5b | 8 (800) | 80 | 4 | 55 | 67 | 2.56 |

| Exp. | catalyst | Monomer (ratio) | Temp. | time | Yield (%) | $M_n$ (×10³) | $M_w/M_n$ |
|---|---|---|---|---|---|---|---|
| 52 | 5a | 9 (800) | 80 | 4 | 100 | 143 | 2.32 |
| 53 | 5b | 9 (800) | 80 | 4 | 100 | 128 | 2.26 |
| 54 | 5b | 10 (800) | 80 | 10 | 8 | 89 | 1.67 |
| 55 | 5a | 11 (800) | 80 | 4 | 91 | 583 | 2.07 |
| 56 | 5b | 11 (800) | 80 | 4 | 99 | 565 | 1.81 |
| 57 | 5a | 12 (800) | 80 | 10 | 100 | 398 | 2.12 |
| 58 | 5b | 12 (800) | 80 | 10 | 100 | 369 | 2.10 |
| 59 | 5a | 14 (800) | 80 | 10 | 95 | d | — |
| 60 | 5b | 14 (800) | 80 | 10 | 96 | d | — |
| 61 | 5a | 15 (800) | 80 | 4 | 100 | 23 | 3.41 |
| 62 | 5b | 15 (800) | 80 | 4 | 100 | 17 | 2.87 |
| 63 | 5a | 16 (800) | 80 | 10 | 100 | d | — |
| 64 | 5b | 16 (800) | 80 | 10 | 100 | d | — |
| 65 | 5a | 17 (250) | 80 | 15 | 80 | 335 | 1.70 |
| 66 | 5b | 17 (250) | 80 | 15 | 88 | 279 | 1.83 |
| 67 | 5b | 17 (250) | 80 | 6 | 68 | — | — |

$^d$molecular weight could be determined because of the insolubility of the polymer.

EXAMPLE 17

Ring Closing Metathesis Reaction

The ring closing metathesis reaction of various dienes was performed according to the following procedure. In a 10 ml Schlenck tube, 0.095 mmole of a diene, 13.2 µl (0.095 mmole) mesitylene, and 50 µl of a solution of a Schiff base vinylidene ruthenium complex prepared according to example 15 were added to 1 ml of deuterated benzene and heated with stirring to 70 or 85° C. (as mentioned in table 11 below). Ethylene formed was removed in vacuo at 10 minutes intervals. After 2 hours the solution was cooled to 20° C. and poured into an NMR tube. Product yield is determined with $^1$H-NMR analysis by integration of allylic protons. The formation of cyclic isomers, oligomers or telomers was ruled out by GC-MS analysis of the reaction mixture. The reaction product was identified by purification of the concentrated reaction mixture by flash column chromatography over a silica gel column (hexane/ethyl acetate=6:1, $R_f$=0.3).

The following table 11 successively indicates for each experiment, after the reaction temperature T (expressed in ° C., first column), the structure of the diene involved, the structure of the resulting product, the reaction time (expressed in hours) and the reaction yield for each of the Schiff base vinylidene ruthenium complex used as a catalyst (using the same identification number as in example 15).

TABLE 11

| T | Diene$^b$ | Product | Time | 4a | 4b | 5a | 5b |
|---|---|---|---|---|---|---|---|
| 70 | 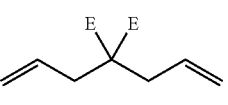 |  | 2 | 96 | 98 | 100 | 100 |

TABLE 11-continued

| T | Diene[b] | Product | Time | 4a | 4b | 5a | 5b |
|---|---|---|---|---|---|---|---|
| 70 | (4,4-diethoxycarbonyl-hepta-1,6-diene with methyl) | (methyl-substituted 4,4-diethoxycarbonylcyclopentene) | 2 | 14 | 23 | 33 | 35 |
| 85 | | | 20 | 36 | 43 | 59 | 79 |
| 85 | (dimethyl diallyl malonate analogue) | (dimethylcyclopentene diester) | 20 | 5 | 11 | 16 | 26 |
| 70 | (1,7-octadiene) | (cyclohexene) | 2 | 98 | 99 | 100 | 100 |
| 70 | (diallyl ether) | (2,5-dihydrofuran) | 2 | 97 | 98 | 100 | 100 |
| 70 | (diallyl phthalate) | (phthalate cyclic product) | 2 | 34 | 48 | 57 | 65 |
| 85 | | | 20 | 51 | 60 | 72 | 83 |
| 70 | (linalool-type diene with OH) | (cyclopentene with OH) | 2 | 13 | 32 | 36 | 39 |
| 85 | | | 20 | 27 | 54 | 68 | 80 |

EXAMPLE 18

Preparation of Catalysts wherein a Schiff Base Containing Ruthenium Complex is Anchored to a Mesoporous Crystalline Molecular Sieve.

All reactions and manipulations were performed under an argon atmosphere by using conventional Schlenck-tube techniques. Argon gas was dried by passage through $P_2O_5$ (Aldrich 97%). $^1$H-NMR spectra (500 MHz) were recorded on a Bruker AM spectrometer. The chemical shifts are reported in ppm and TMS is used as reference compound. Solid-state NMR spectra were acquired on a Bruker DSX-300 spectrometer operating at 300.18 MHz for $^1$H-NMR, 75.49 MHz for $^{13}$C-NMR, 121.51 MHz for $^{31}$P-NMR and 59.595 MHz for $^{29}$Si-NMR. The spectra were recorded under MAS conditions with a classical 4 mm probe head allowing spinning frequencies up to 12 kHz. The anchoring of the homogeneous catalyst was confirmed by a Raman spectrometer Bruker Equinox 55 with a FRA 106 module. The loading of the heterogeneous hybrid catalyst was determined with a Varian Liberty ICP/MS spectrometer and an ARL 9400 Sequential XRF spectrometer. XRD spectra were recorded on a Siemens diffractometer D5000. Elemental analysis was performed with a Carlo Erba EA 1110 equipment. The BET analysis was done on a Gemini micrometrics 2360 surface area analyser with Flow prep 060 degasser. The samples were dried overnight at 423° K and cooled to room temperature prior to adsorption. Extra care with the functionalised materials was necessary due to the possibility of aerial oxidation, therefore transfer to the balance and outgassing of the system was fast. Nitrogen isotherms were recorded at 77° K. Specific surface areas were determined from the linear part of the BET plot ($P/P_0$=0.05-0.3).

After calcination, the mesoporous crystaziline molecular sieve MCM41 was characterised by XRD, $N_2$ adsorption and Raman spectroscopy. MCM-41 was dried overnight in vacuo at 423° K. to achieve thermodesorption of physically adsorbed water from the silica surface.

Figure 7:
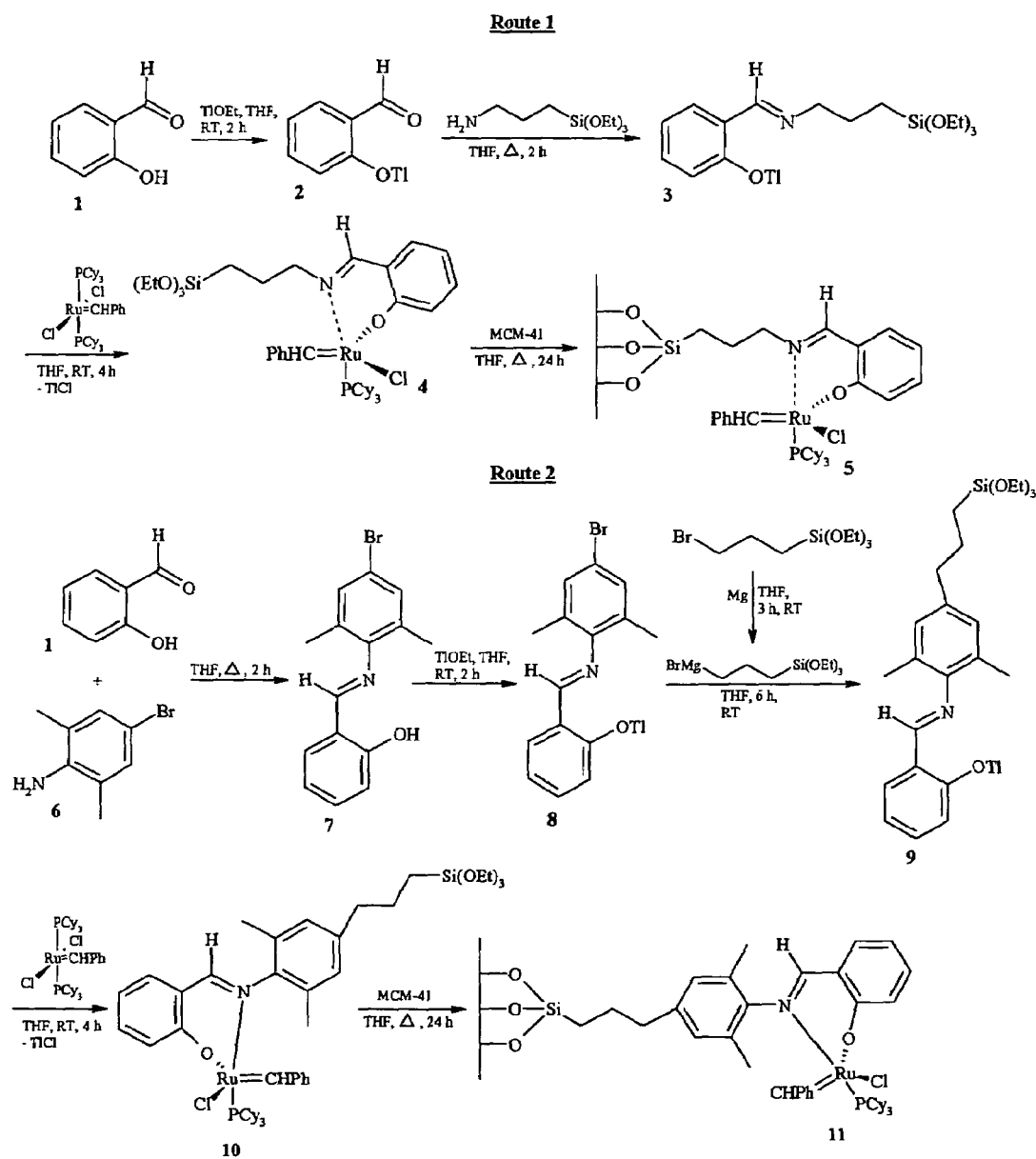
FIG. 7 shows two alternative synthetic routes for producing a derivative of a monometallic complex of the invention that may be covalently bonded to a carrier.

Two different routes were tested for the synthesis of solid-supported catalysts 5 and 11 respectively, as illustrated in FIG. 7.

In a first embodiment, the Schiff base ruthenium complex 10 shown in FIG. 7 was made by route 2 and characterised as follows: 2 mmol salicylaldehyde 1 was dissolved in 15 ml THF. Under stirring, 2 mmol 4bromo-2,6-dimethylaniline 6 was added and the reaction mixture was stirred for 2 hours at reflux temperature. The resulting salicylaldimine product was precipitated upon cooling to 0° C. and a solid yellow product was formed. The solid was filtered, washed and dried in vacuo to afford the desired salicylaldimine ligand 7 in excellent yield (95%). To a solution of the Schiff base ligand 7 (2 mmol)

in 15 ml THF was added dropwise a solution of 2 mmol thallium ethoxide in THF (5 ml) at room temperature. Immediately after the addition, a pale yellow solid was formed and the reaction mixture was stirred for 2 hours at room temperature. The quantitatively formed salt 8 was immediately used in the next step without further purification. To a suspension of 2 mmol Mg powder in THF (10 ml), 2 mmol of bromopropyltrimethoxysilane was added dropwise, then the mixture was stirred for 3 hours at room temperature and transferred quantitatively to the salt 8 and stirred for 6 hours at room temperature to afford the spacer-modified Schiff base ligand 9 as a green-yellow solid.

To the solution of the ethoxylated thallium salt 9 was added a solution of 2 mmol catalyst [RuCl$_2$(PCy$_3$)$_2$=CHPh] in 10 ml THF. The reaction mixture was stirred at room temperature for 4 hours. After evaporation of the solvent, the residue was dissolved in a minimal amount of benzene and cooled to 0° C. Thallium chloride was removed via filtration. The desired complex was then washed with cold benzene (10 ml three times) and the filtrate was evaporated. The solid residue was recrystallized from pentane (−70° C.) to give the Schiff base modified complex 10 as a green-brown solid, which was characterised as follows:

$^1$H-NMR (CDCl$_3$) δ (ppm) 19.41 (d, 1H), 8.18 (d, 1H), 7.96 (d, 1H), 7.91 (d, 2H), 6.93 (d, 1H), 7.53 (t, 1H), 7.31 (t, 1H), 7.20 (t, 2H), 7.03 (t, 1H), 7.00 (s, 1H), 6.95 (s, 1H), 3.71 (m, 6H), 2.44 (q, 3H), 2.29 (s, 3H), 1.77 (d, 3H), 1.69 (t, 2H), 1.17-1.67 (m, 30H), 1.15 (m, 4H), 1.11 (t, 9H); $^{31}$P-NMR (CDCl$_3$) δ (ppm) 58.19; elemental analysis calculated (%) for RuC$_{49}$H$_{73}$PO$_4$NClSi (935.61): C 63.90, H 7.86, N 1.50; found: C 62.97, H 7.73, N 1.53.

Then 2 mmol of the Schiff base modified complex 10 was then dissolved in 15 ml THF. This solution was quantitatively transferred to 3 g MCM-41 that was dried overnight at 150° C. After 24 hours refluxing in THF the heterogeneous catalyst 11 was filtered off under nitrogen atmosphere and rigorously washed with THF and toluene until the filtrate was colourless. Subsequent drying in vacuum afforded the heterogeneous catalyst 11 as a green powder.

In a second embodiment, the Schiff base modified complex 4 was made by route 1 shown in FIG. 7 and was characterised as follows:

$^1$H-NMR (CDCl$_3$) δ (ppm) 19.92 (d, 1H), 8.95 (d, 1H), 7.55 (t, 1H), 7.02-7.35 (br m, 7H), 6.83 (t, 1H), 3.89 (m, 6H), 3.57 (q, 3H), 1.86 (t, 2H), 1.25-1.81 (m, 30H), 1.21 (m, 4H), 1.17 (t, 9H); $^{31}$P-NMR (CDCl$_3$) δ (ppm) 58.70; elemental analysis calculated (%) for RuC$_{41}$H65PO$_4$NClSi (831.46): C 59.22, H 7.88, N 1.68; found: C 58.71, H 8.54, N 1.60.

Then the heterogeneous catalyst 5 was prepared from the Schiff base modified complex 4 by a way similar to catalyst 11.

Then both heterogeneous catalysts 5 and 11 were further characterised, and their structure compared to the starting MCM-41 material, by X-ray diffraction, nitrogen adsorption analysis, Raman spectroscopy, X-ray fluorescence and solid state NMR analysis. Results were as follows:

XRD measurements confirmed that the synthesized mesoporous support had MCM41 structure. The calcined MCM-41 exhibits a very strong peak at d spacing of 3.733 nm (100) and three weaker peaks at 2.544 nm (110), 2.010 nm (200) and 1.240 nm (210). These four peaks fit a hexagonal unit cell with $a_0$=4.310 nm (with $a_0$=2d$_{100}$/√3). For the heterogeneous catalyst 5 the d$_{100}$ spacing and $a_0$ amount to respectively 3.611 nm and 4.170 nm. For catalyst 11 values of respectively 3.714 nm and 4.289 nm are obtained. Since XRD patterns of the heterogeneous catalysts were essentially the same as that of the pristine MCM-41, the long-range ordered structure of the support was confirmed to be preserved.

The data obtained from the N$_2$ adsorption measurements and the XRD analyses are summarized in the table hereunder.

| Catalyst | $S_{BET}$ (m$^2$/g)$^a$ | $V_p$ (cm$^3$/g)$^b$ | APD (nm)$^c$ | Wall thickness$^d$ |
|---|---|---|---|---|
| MCM-41 | 1451 | 1.032 | 2.57 | 1.74 |
| 5 | 592 | 0.6054 | 2.40 | 1.77 |
| 11 | 602 | 0.6108 | 2.42 | 1.79 |

$^a$BET surface area obtained from the desorption branches of the N$_2$ adsorption isotherm (BET surface area = Brunauer-Emmett-Teller surface area).
$^b$Pore volume obtained from the Barrett-Joyner-Halenda equation).
$^c$The mesopore diameter was obtained from the PSD curve (PSD curve = Pore Size Distribution curve).
$^d$Wall thickness = $a_0$ − APD (APD = Average Pore Diameter).

The surface area, pore volume and pore diameters of the catalysts were as expected for mesoporous materials. Moreover, porosity measurements of both MCM-41 and the heterogeneous catalysts reveal type IV IUPAC adsorption-desorption isotherms. As shown above, the BET surface and the pore volume of the heterogeneous catalysts are decreased by approximately 60% in comparison with MCM41. All these results indicate that the internal pores of the MCM41 are occupied by the catalytic complexes and that the accessibility and structure of the mesopores is maintained after modification.

Figure 15:
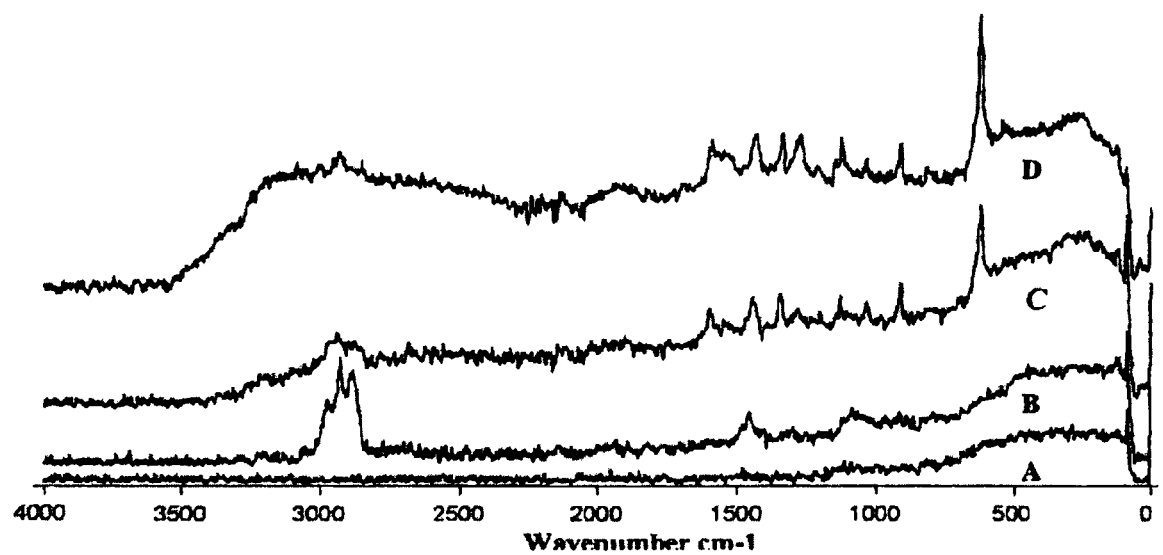
FIG. 15 shows Raman spectra of MCM-41 (A), MCM-41+ spacer (B), spacer-modified homogenous catalyst 4 (C) and heterogeneous catalytic system 5 (D).

In order to check the formation of a covalent bond between the tris(alkoxy) silyl-functionalized homogeneous complexes (4 and 10 respectively) and the MCM-41 surface, Raman spectroscopy was performed. Here we will only discuss the anchoring process that leads to the heterogeneous catalyst 5. Comparison of the Raman spectra of MCM-4 I (FIG. 15, A) and the spacer-modified MCM-41 (FIG. 15, B) clearly shows the superposition of the spacer vibrations on the MCM-41 baseline. Comparing the Raman spectra of MCM-41 and the heterogeneous catalyst 5 (FIG. 15, D) proves the grafting of the homogeneous species 4. Comparison of the Raman spectrum of the spacer modified homogeneous catalyst 4 (FIG. 15,C) and catalyst 5 is performed to eliminate any doubt concerning the chemical attachment of the homogeneous catalyst. We clearly see that every peak in the spectrum of the homogeneous catalyst 4 is also present in the spectrum of the heterogeneous catalyst 5. The small shifts of some peaks in FIG. 15, D compared with C indicate the change in chemical environment of the different functional groups originating from the chemical attachment of the catalyst to the carrier. To conclude, we can state that both the Raman and the BET data confirm the desired covalent anchoring.

XRF measurements reveal a loading of 0.1069 mmol Ru complex/g heterogeneous catalyst 5 and 0.054 mmol Ru complex/g heterogeneous catalyst 11.

The structure of the heterogeneous catalysts 5 and 11 was also studied by solid state NMR. For MCM-41, the proton spectrum only reveals the presence of silanol groups and water. In the $^{29}$Si CP MAS NMR spectrum of MCM-41, three different peaks at 90 ppm, 100 ppm and 110 ppm were observed. These values can be attributed to respectively Si(OH)$_2$(OSi)$_2$, Si(OH)(OSi)$_3$ and Si(OSi)$_4$. The proton spectrum of MCM-41+aminopropyltriethoxysilane and of MCM-41+bromopropyltriethoxysilane only reveals the presence of —CH$_2$ and —CH$_3$ groups. A small signal around 0 ppm can be attributed to the SiCH$_2$ of the spacer molecules. However, the $^{13}$C CP MAS NMR spectra of these samples reveal some interesting features. For MCM-41+aminopropyltriethoxysilane, two peaks at 50 ppm and 70 ppm can be attributed to respectively a —OCH$_2$— and a —CH$_2$N— configuration. For MCM-41+bromopropyltriethoxysilane, two peaks at 50 ppm and 36 ppm can be attributed to respectively a —OCH$_2$— and a —CH$_2$Br— configuration. The signals around 50 ppm, appearing as broad unresolved peaks, indicate that grafting is not complete. For MCM-41+aminopropyltriethoxysilane, the $^{29}$Si CP MAS NMR spectrum reveals unambiguously the presence of a (SiO)$_3$Si*C— species at −58,34 ppm, and a (SiO)$_2$(OEt)Si*C— species at −106.98 ppm. For MCM-41+bromopropyltriethoxysilane, these signals can be found respectively at —59,69 ppm and —106.0 ppm. For both samples, the presence of a (SiO)$_2$(OH)Si*C— signal can be resolved. For MCM41+aminopropyltriethoxysilane and MCM-41+bromopropyltriethoxysilane, these signals can be found at respectively −43.26 ppm and −43.98 ppm. The presence of this Si—OH species is confirmed by the proton spectra of the two samples showing a small signal at 1.8 ppm.

The proton spectrum of the heterogeneous hybrid catalysts only reveals the presence of aromatic and aliphatic protons as broad unresolved peaks. At respectively 8.96 ppm and 8.18 ppm the small peak of the imine-proton for catalysts 5 and 11 can be revealed. The $^{13}$C CP MAS NMR spectra of the heterogeneous catalysts reveal the carbon of the —C=N— bond at 166.1 ppm and 164.2 ppm for complexes 5 and 11, respectively. Again the aromatic and aliphatic carbon atoms can be revealed from the spectrum. Around 5.24 ppm, respectively 4.91 ppm there is an overlapping of the —CH$_3$ and the —SiCH$_2$— peaks for catalyst 5 and 11. The $^{29}$Si CP MAS NMR spectra of the heterogeneous catalysts also reveal the presence of (SiO)$_3$Si*C—, (SiO)$_2$(OEt)Si*C— and (SiO)$_2$(OH)Si*C— species. The $^{31}$p CP-MAS NMR spectra of the heterogeneous catalysts reveal the presence of the P(cyclohexyl)$_3$ at 58.73 ppm and 58.23 ppm for heterogeneous catalysts 5 and 11 respectively. From this we conclude that anchoring of the homogeneous catalysts via the spacer molecule onto MCM-41 takes place with two or three covalent bonds.

EXAMPLE 19

Ring Opening Metathesis Polymerisation with a Heterogeneous Catalyst.

Both heterogeneous catalysts 5 and 11 prepared in example 18 were used for performing the ring-opening metathesis polymerisation of various olefins in a solvent. Cyclooctene and norbomene derivatives were purchased from Aldrich and distilled from CaH$_2$ under nitrogen prior to use. Commercial grade solvents were dried and deoxygenated for 24 hours over appropriate drying agents under nitrogen atmosphere distilled prior to use. In a typical ROMP experiment, 0.005 mmol of the catalyst suspension in toluene was transferred into a 15 ml vessel followed by the addition of the monomer solution in toluene/dichloromethane (2000 equivalents for norbomene, 200 equivalents for cyclooctene and 800 equivalents for norbomene derivatives). Reaction mixture was kept stirring at 35° C. for 6 hours. In order to inactivate the catalyst, 2.5 ml of ethylvinylether/2,6-di-tert-butyl-4-methylphenol (BHT) solution was added and the solution was stirred until complete deactivation. The solution was poured into 50 ml methanol (containing 0.1% BHT) and the polymer were precipitated and filtered off. The polymer was dissolved in CHCl$_3$ so that the catalyst can be filtered off. CHCl$_3$ was then removed in vacuo from the polymer solution until a high viscosity is reached, after which the polymer was precipitated by adding 100 ml methanol. The white polymer was then filtered off and dried in vacuum overnight. The number- and weight average molecular weights (M$_n$ and M$_w$) and polydispersity (M$_w$/M$_n$) of the polymers were determined by gel permeation chromatography (CHCl$_3$, 25° C.) using polystyrene standards. The GPC instrument used was a Waters Maxima 820 system equipped with a PL gel column. DSC measurements were done with a TA instruments DSC-TGA (SDT 2960) equipment using a thermomechanical analyser (TMA 2940). Yields [%] of the polymers formed are depicted in Table 12 below.

TABLE 12

| Substrate | toluene | | dichloromethane | |
|---|---|---|---|---|
| | 5 | 11 | 5 | 11 |
| Cyclooctene | 98 | 90 | 100 | 100 |
| R = H | 78 | 65 | 86 | 76 |
| R = ethyl | 100 | 100 | 100 | 100 |
| R = butyl | 100 | 100 | 100 | 100 |
| R = hexyl | 83 | 76 | 89 | 79 |
| R = decyl | 81 | 71 | 84 | 72 |
| R = ethylidene | 34 | 28 | 45 | 32 |
| R = phenyl | 70 | 61 | 77 | 64 |
| R = cyclohexyl | 100 | 87 | 100 | 94 |
| R = ethylnorbornane | 82 | 73 | 93 | 79 |
| R = cyano | 17 | 5 | 68 | 53 |
| R = hydroxymethyl | 21 | 8 | 74 | 66 |
| R = chloromethyl | 79 | 74 | 98 | 91 |
| R = triethoxysilyl | 100 | 86 | 100 | 90 |

Furthermore, the data gathered in table 13 clearly demonstrate that the solvent used is very decisive for the characteristics of the obtained polymers. As the lower polydispersities and higher initiator efficiencies indicate, the use of dichloromethane instead of toluene, makes polymerisation proceed in a more controlled way and this irrespective of the catalyst used.

TABLE 13

| Solvent | Catalyst | Substrate | $M_n$ (×10$^3$) | PDI |
|---|---|---|---|---|
| toluene | 5 | Cyclooctene | 28 | 1.65 |
| | | R = H | 222 | 1.73 |
| | | R = ethyl | 119 | 1.63 |
| | | R = butyl | 154 | 1.69 |
| | | R = hexyl | 154 | 1.64 |
| | | R = decyl | 214 | 1.70 |
| | | R = ethylidene | 55 | 1.67 |
| | | R = phenyl | 138 | 1.83 |
| | | R = cyclohexenyl | 196 | 1.81 |
| | | R = ethylnorbornane | 149 | 1.75 |
| | | R = cyano | 77 | 1.98 |
| | | R = chloromethyl | 106 | 1.59 |
| | | R = triethoxysilyl | 270 | 1.67 |
| | 11 | Cyclooctene | 28 | 2.01 |
| | | R = H | 227 | 2.11 |
| | | R = ethyl | 132 | 2.14 |
| | | R = butyl | 179 | 2.03 |
| | | R = hexyl | 157 | 1.96 |
| | | R = decyl | 218 | 1.99 |
| | | R = ethylidene | 56 | 2.13 |
| | | R = phenyl | 151 | 2.08 |
| | | R = cyclohexenyl | 209 | 2.17 |
| | | R = ethylnorbornane | 162 | 2.01 |
| | | R = chloromethyl | 132 | 1.93 |
| | | R = triethoxysilyl | 299 | 1.98 |
| dichloromethane | 5 | Cyclooctene | 26 | 1.33 |
| | | R = H | 208 | 1.39 |
| | | R = ethyl | 107 | 1.43 |
| | | R = butyl | 143 | 1.36 |
| | | R = hexyl | 155 | 1.40 |
| | | R = decyl | 183 | 1.38 |
| | | R = ethylidene | 61 | 1.46 |
| | | R = phenyl | 136 | 1.42 |
| | | R = cyclohexenyl | 176 | 1.47 |
| | | R = ethylnorbornane | 156 | 1.42 |
| | | R = cyano | 94 | 1.52 |

TABLE 13-continued

| Solvent | Catalyst | Substrate | $M_n$ (×10³) | PDI |
|---|---|---|---|---|
| | | R = hydroxymethyl | 102 | 1.56 |
| | | R = chloromethyl | 116 | 1.29 |
| | | R = triethoxysilyl | 230 | 1.37 |
| | 11 | Cyclooctene | 27 | 1.71 |
| | | R = H | 191 | 1.74 |
| | | R = ethyl | 116 | 1.70 |
| | | R = butyl | 150 | 1.63 |
| | | R = hexyl | 139 | 1.69 |
| | | R = decyl | 163 | 1.65 |
| | | R = ethylidene | 43 | 1.76 |
| | | R = phenyl | 121 | 1.78 |
| | | R = cyclohexenyl | 175 | 1.63 |
| | | R = ethylnorbornane | 143 | 1.68 |
| | | R = cyano | 84 | 1.77 |
| | | R = hydroxymethyl | 102 | 1.79 |
| | | R = chloromethyl | 117 | 1.53 |
| | | R = triethoxysilyl | 222 | 1.62 |

EXAMPLE 20

Ring-closing Metathesis in the Presence of a Heterogeneous Catalyst

Reactions were performed on the bench top in air by weighing 5 mole % of the catalyst into a dry 10 ml vessel and suspending the solid in 2 ml benzene. A solution of the appropriate dienic substrate (0.1 mmole) in benzene (2 ml) was added, together with the internal standard dodecane. The reaction mixture was stirred for the appropriate time at the appropriate temperature, both being indicated in table 14 below. Product formation and diene disappearance were monitored by gas chromatography (GC) and confirmed in reproducibility experiments by $^1$H-NMR spectroscopy through integration of the allylic methylene peaks (the solvent being deuterated benzene and the internal standard 1,3,5-mesitylene). GC analysis of the reaction mixture also ruled out the formation of cyclo-isomers, oligomers or telomers.

Table 14 summarizes results obtained with some representative substrates, wherein we assessed the influence of the reaction temperature and reaction time on the activity of catalysts 5 and 11 of example 18. Whatever temperature or reaction time used, catalytic system 11 is more efficient than system 5. 1,7-octadiene, diallylether and diethyl diallylmalonate smoothly underwent cyclisation with both catalytic systems, even for only 4 hours at 55° C., whereas more rigorous conditions are needed for converting tri- and tetra-substituted malonate derivatives. It is also quite clear that the reaction temperature is a decisive factor for achieving good catalyst performance. Importantly, workup of the ring-closed reaction products simply consists in the removal of the catalyst through filtration and evaporation of the solvent in vacuo.

EXAMPLE 21

Atom Transfer Radical Polymerisation in the Presence of a Heterogeneous Catalyst All reagents and solvents were dried, distilled and stored under nitrogen at −20° C. with conventional methods. In a typical ATRP experiment, 0.0117 mmole of the heterogeneous catalyst 11 produced in example 18 was placed in a glass tube (in which the air was expelled by three vacuum-nitrogen cycles) containing a magnet bar and capped by a three-way stopcock. Then styrene (as the monomer) and 1-bromoethyl benzene (as the initiator) were added so that the molar ratio [catalyst]/[initiator]/[monomer] was 1:2:800. All liquids were handled under argon with dried syringes. The reaction mixture was heated for 17 hours at 110° C. then, after cooling, diluted in THF and poured in 50 ml methanol under vigorous stirring, after which the precipitated polystyrene was filtered with suction. The polymer was finally dissolved in $CHCl_3$ so that the catalyst can be filtered off. $CHCl_3$ was then removed in vacuo from the polymer solution until a high viscosity was reached, then the polymer was precipitated by adding 100 ml methanol, filtered off, dried under vacuum for 15 hours and analysed. Polymer yield was 73%, molecular weight ($M_n$) was 39,000 and polydispersity index ($M_w/M_n$) was 1.62.

Figure 8:
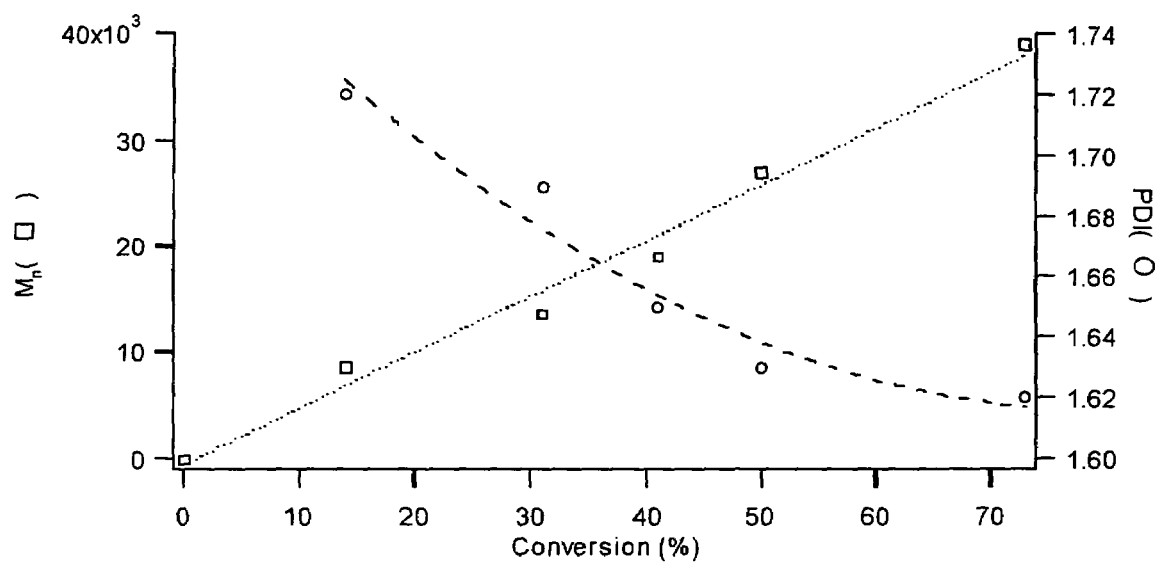
FIG. 8 and FIG. 9 show the evolution, as a function of time or conversion rate, of the molecular weight and polydispersity of a polystyrene produced by atom transfer radical polymerisation in the presence of a heterogeneous catalyst of this invention.
Figure 9:
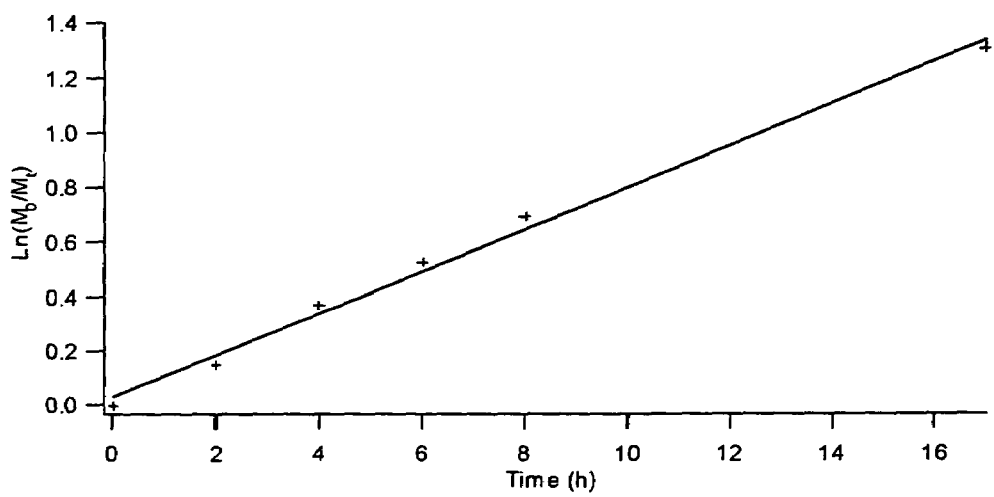

In order to check the living character of this ATRP reaction, we conducted the following kinetic experiments: monomer conversion and number average molecular weight ($M_n$) were followed in function of time and the dependence of molecular weight and polydispersity on the monomer conversion is illustrated in FIG. 8. The linear dependence observed for $M_n$ is in agreement with a controlled process with a constant number of growing chains. In addition, the significant decrease of the polydispersity (reaching a value of 1.62 at 73% conversion) while polymerisation proceeds indicates that the radicals are long-lived. Furthermore, the first order kinetic plot (FIG. 9) shows linear time dependence, indicating that termination reactions are almost completely excluded. Therefore we conclude that polymerisation proceeded in a controlled fashion, allowing to synthesize polystyrene with predetermined molecular weight and narrow polydispersity.

EXAMPLE 22

Kharash Addition in the Presence of a Heterogeneous Catalyst

All reagents and solvents were dried, distilled and stored under nitrogen at −20° C. with conventional methods. Reactions were performed on the bench top in air by weighing 0.01 mmole of the catalyst 5 or 11 of example 18 into a dry 10 ml vessel and suspending the solid in 2 ml toluene. Then the solution of alkene (3 mmole), $CCl_4$ (4.33 mmole) and dode-

TABLE 14

| Substrate | cata 5 55° C. 4 h | cat 11 55° C. 4 h | cata 5 55° C. 17 h | cat 11 55° C. 17 h | cata 5 85° C. 4 h | cat 11 85° C. 4 h | cata 5 85° C. 17 h | cat 11 85° C. 17 h |
|---|---|---|---|---|---|---|---|---|
| Diethyl diallyl malonate | 77 | 86 | 100 | 100 | 100 | 100 | 100 | 100 |
| Tri-substituted malonate | <5 | <5 | 27 | 32 | 11 | 20 | 41 | 58 |
| Tetra-substituted malonate | <5 | <5 | 9 | 12 | <5 | 8 | 28 | 37 |
| 1,7-otadiene | 84 | 89 | 100 | 100 | 100 | 100 | 100 | 100 |
| Diallyl ether | 73 | 82 | 100 | 100 | 100 | 100 | 100 | 100 |
| Diallyl phtalate | 14 | 25 | 46 | 56 | 31 | 34 | 69 | 82 |
| Linalool | 8 | 13 | 28 | 35 | 18 | 19 | 51 | 73 | cane (0.083 ml) in toluene (1 ml) were added and the reaction mixture was heated for 17 hours at the appropriate reaction temperature shown in table 15. Yields of the resulting products were obtained by GC analysis of the reaction mixture using dodecane as internal standard, and are reported in table 15 below.

TABLE 15

|  | 65° C. | | 85° C. | |
| --- | --- | --- | --- | --- |
|  | 5 | 11 | 5 | 11 |
| Methyl methacrylate | <5 | 14 | 16 | 43 |
| Isobutyl methacrylate | <5 | 11 | 9 | 25 |
| Methyl acrylate | <5 | 12 | 19 | 37 |
| Butyl acrylate | <5 | 9 | 13 | 22 |
| Styrene | 45 | 63 | 67 | 91 |
| Diethylallylmalonate | 51 | 77 | 74 | 85 |

EXAMPLE 23

Vinylation Reaction in the Presence of a Heterogeneous Catalyst

In a typical vinylation experiment, 4.4 mmole of a carboxylic acid (formic acid or acetic acid), 4.4 mmole of an alkyne (phenylacetylene or 1,7-octadiyne) and 0.04 mmole of the catalyst 5 or 11 of example 18 were transferred into a 15 ml glass vessel containing 3 ml toluene. Then the reaction mixture was heated for 4 hours at 100° C. under an inert atmosphere. The total yield was determined with Raman spectroscopy by following the diminishing intensity of the $v_{C\equiv C}$ of phenylacetylene or 1,7-octadiyne and using a calibration curve. Conformation of the products obtained was determined by GC/MS, making use of the different fragmentations of the isomers. GC/MS measurements excluded the formation of other products than those reported below.

Results of these vinylation experiments are summarized in table 16 (wherein M stands for Markovnikov). When 1,7-octadiyne was used as a substrate, the addition of both carboxylic acids resulted in the selective formation of (E)-alk-1-enyl esters corresponding to a regio- and stereoselective anti-Markovnikov addition of the acid to the triple bond, irrespective the catalytic system used. The total yield however depends upon the type of catalyst and carboxylic acid used. Besides the formation of the (E)-alk-1-enyl ester, also a small percentage of (Z)-alk-1-enyl ester, Markovnikov addition products and disubstituted enol esters were obtained. When phenylacetylene is used as an alkyne, the total yields were noticeably higher than with 1,7-octadiyne. The latter induced a totally different selectivity in the vinylation process, i.e. the heterogeneous catalyst provided high levels of reactivity for the formation of Markovnikov addition products.

TABLE 16

| Catalyst/Alkyne/ carboxylic acid | | | total yield (%) | % M. | % anti- M. (Z) | % anti- M. (E) | % disubstituted enol ester |
| --- | --- | --- | --- | --- | --- | --- | --- |
| 5 | ph.ac. | formic | 90 | 71 | 9 | 20 | |
| | | Acetic | 93 | 45 | 22 | 33 | |
| 11 | ph.ac. | Formic | 96 | 82 | 5 | 13 | |
| | | Acetic | 99 | 74 | 9 | 17 | |
| 5 | octad. | Formic | 75 | 8 | 5 | 74 | 13 |
| | | Acetic | 86 | 11 | 3 | 79 | 7 |
| 11 | octad. | Formic | 63 | 6 | 4 | 72 | 18 |
| | | acetic | 75 | 15 | — | 78 | 7 |

EXAMPLE 24

Preparation of a Schiff Base Modified Homobimetallic Ruthenium Complex

Figure 10:
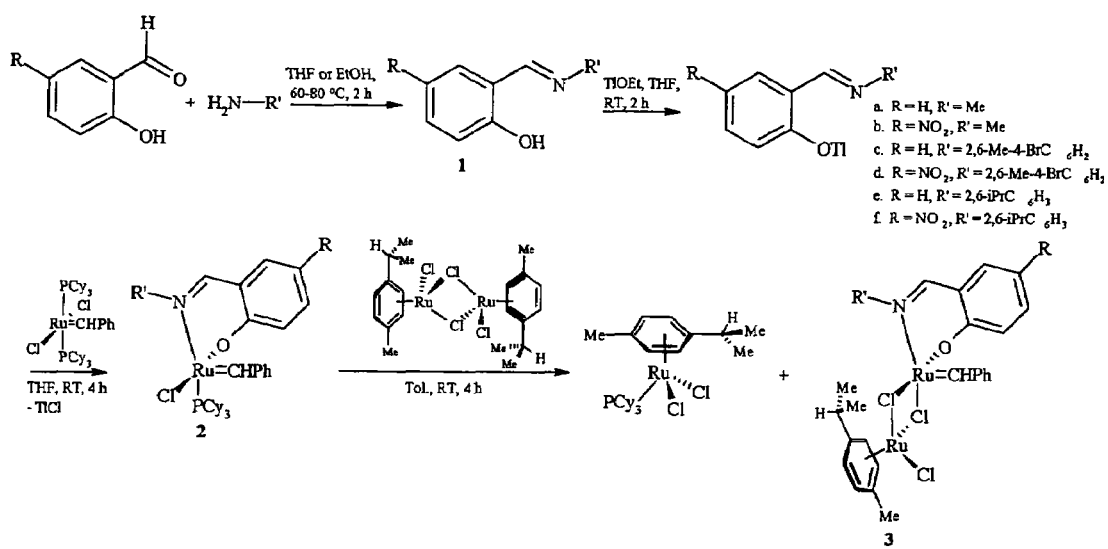
FIG. 10 schematically shows the synthetic route for producing a bimetallic complex of the invention.

This synthesis proceeded according to the scheme shown in FIG. 10. Schiff base substituted ruthenium complexes having formulae (2.a-f) were prepared in two steps and purified as follows. In a first step, to a solution in THF (10 ml) of the appropriate Schiff base of formula (1.a-f) prepared according to example 1, a solution of thallium ethoxide in THF (5 ml) was added dropwise at room temperature. Immediately after addition, a pale yellow solid formed and the reaction mixture was stirred for 2 hours at 20° C. Filtration of the solid under an argon atmosphere provided the respective salicylaldimine thallium salt in quantitative yield, which was immediately used in the next step without further purification.

In a second step, to a solution of the said salicylaldimine thallium salt in THF (5 ml) was added a solution of a catalyst having the formula [RuCl$_2$(PCy$_3$)$_2$=CHC$_6$H$_5$] in THF (5 ml). The reaction mixture was stirred at room temperature for 4 hours. After evaporation of the solvent, the residue was dissolved in a minimal amount of benzene and cooled to 0° C. Thallium chloride was removed via filtration. After evaporation of the solvent, the solid residue was recrystallized from pentane (−70° C.) to provide the respective Schiff base substituted ruthenium complex (2.a-f) in good yield as a brown solid.

Then, to a benzene solution (25 ml) of 1 mmole of the Schiff base substituted ruthenium complex (2-a-f) was added a benzene solution (25 ml) of the dimer complex (1 mmole) having the formula [RuCl$_2$(p-cymene)]$_2$. The solution was stirred for 4 hours at room temperature, during which time a solid precipitate formed from the solution. This solid was isolated via filtration under inert atmosphere and washed with benzene (30 ml three times) to remove the [(p-cymene)RuCl$_2$P(Cyclohexyl)$_3$] byproduct and any unreacted starting materials. After recrystallization from a chlorobenzene/pentane mixture and additional washing with 10 ml pentane (two times) to remove the residual chlorobenzene, the product was dried in vacuo, affording the bimetallic Schiff base substituted ruthenium complexes 3.a-f in the following yields. Said complexes were further characterized by magnetic nuclear resonance (NMR) and infrared spectroscopy (IR), the results of such analysis being as follows.

Bimetallic ruthenium complex 3.a: 0.419 g (63%) as an orange-green powder. $^1$H-NMR (CDCl$_3$) δ 19.97 (d, 1H), 9.03 (d, 1H), 7.64 (t, 1H), 7.09-7.44 (br m, 7H), 7.01 (t, 1H), 5.58 (d, 1H), 5.46 (d, 1H), 5.29 (d, 1H), 5.15 (d, 1H), 3.31 (d, 3H), 2.92 (septet, 1H), 2.19 (s, 3H), 1.35 (d, 3H) and 1.32 (d, 3H). IR (cm$^{-1}$) 3060 ($v_{CH}$, w), 3054 ($v_{CH}$, w), 2838-2901 ($v_{CH3}$, br), 2806 ($v_{CH2}$, w), 1617 ($v_{C=N}$, s), 1605 ($v_{C=C(Ph)}$, w), 1583 ($v_{C=C(Ph)}$, w), 1506 ($v_{C=C(Ph)}$, w), 1455 ($v_{C=C(Ph)}$, w), 1449 ($v_{CH2}$, w), 1382 (skel.$_{iPr}$, m), 1361 (skel.$_{iPr}$, m), 1106 ($v_{Ru-O-Ph}$, w), 1003 ($v_{skel.PCy3}$, w), 773 ($\gamma_{CH}$, w), 564 ($v_{Ru-O-Ph}$, w), 544 ($v_{Ru-O-Ph}$, w), 512 ($v_{Ru-Cl}$, w) and 440 ($v_{Ru-N}$, w). Elemental analysis calculated (%) for Ru$_2$C$_{25}$H$_{28}$ONCl$_3$ (666.96): C 45.02, H 4.23, N .2.10; found: C 45.10, H 4.25, N 2.11.

Bimetallic ruthenium complex 3.b: 0.476 g (67%) as an orange-green powder. $^1$H-NMR (CDCl$_3$) δ 20.02 (d, 1H), 9.08 (d, 1H), 8.34 (d, 1H), 8.19 (d, 1H), 7.53 (d, 2H), 7.45 (t, 1H), 7.38 (t, 2H), 7.16 (d, 1H), 5.64 (d, 1H), 5.52 (d, 1H), 5.19 (d, 1H), 3.36 (d, 3H), 2.96 (septet, 1H), 2.21 (s, 3H), 1.40 (d, 3H) and 1.37 (d, 3H). IR (cm$^{-1}$) 3054 ($v_{CH}$, w), 3047 ($v_{CH}$, w), 2835-2898 (V$_{CH3}$, br), 2802 (V$_{CH2}$, w), 1615 ($v_{C=N}$, s), 1600 (V$_{C=C(Ph)}$, w), 1577 ($v_{C=C(Ph)}$, w), 1550 ($v_{NO2}$, s), 1500 ($v_{C=C(Ph)}$, w), 1447 ($v_{C=C(Ph)}$, w), 1441 ($v_{CH2}$, w), 1382 (skel.$_{iPr}$, m), 1363 (skel.$_{iPr}$, m), 1332 ($v_{NO2}$, s), 1098 ($v_{Ru-O-Ph}$, w), 997 ($v_{skel.PCy3}$, w), 768 ($\gamma_{CH}$, w), 558 ($v_{Ru-O-Ph}$, w), 540 ($v_{Ru-O-Ph}$, w), 503 ($v_{Ru-Cl}$, w) and 437 ($v_{Ru-N}$, w). Elemental analysis calculated (%) for $RU_2C_{25}H_{27}O_3N_2Cl_3$ (711.94): C 42.17, H 3.82, N 3.93; found: C 42.24, H 3.84, N 3.91.

Bimetallic ruthenium complex 3.c: 0.511 g (61%) as an orange powder. $^1$H-NMR (CDCl$_3$) δ 19.48 (d, 1H), 8.21 (d, 1H), 8.12 (d, 1H), 8.06 (d, 2H), 7.72 (t, 1H), 7.44 (t, 2H), 7.38 (t, 1H), 7.12 (t, 1H), 7.09 (s, 1H), 7.06 (d, 1H), 7.02 (s, 1H), 5.45 (d, 1H), 5.30 (d, 1H), 5.17 (d, 1H), 5.06 (d, 1H), 2.84 (septet, 1H), 2.06 (s, 3H), 2.03 (s, 3H), 1.89 (d, 3H), 1.28 (d, 3H) and 1.24 (d, 3H). IR (cm$^{-1}$) 3052 ($v_{CH}$, w), 3038 ($v_{CH}$, w), 2848-2968 ($V_{CH3}$, br), 1601 ($v_{C=N}$, s), 1579 ($v_{C=C(Ph)}$, w), 1523 ($v_{C=C(Ph)}$, w), 1466 ($v_{C=C(Ph)}$, w), 1443 ($v_{C=C(Ph)}$, w), 1385 (skel.$_{iPr}$, m), 1367 (skel.$_{iPr}$, m), 1062 ($v_{Ru-O-Ph}$, w), 1003 ($v_{skel.PCy3}$, w), 801 ($\gamma_{CH}$, w), 784 ($\gamma_{CH}$, w), 692 ($v_{C-Br}$, s), 666 ($v_{Ru-N}$, w), 554 ($v_{Ru-O-Ph}$, w), 527 ($v_{Ru-O-Ph}$, w) and 492 ($v_{Ru-Cl}$, w). Elemental analysis calculated (%) for Ru$_2$C$_{32}$H$_{33}$ONCl$_3$Br (835.97): C 45.97, H 3.98, N 1.68; found: C 46.03, H 4.01, N 1.65.

Bimetallic ruthenium complex 3.d: 0.602 g (68%) as a dark orange powder. $^1$H-NMR (CDCl$_3$) δ 19.50 (d, 1H), 8.36 (d, 1H), 8.31 (d, 1H), 8.10 (d, 2H), 7.76 (t, 1H), 7.71 (d, 1H), 7.43 (t, 2H), 7.15 (d, 1H), 7.11 (s, 1H), 7.07 (s, 1H), 5.49 (d, 1H), 5.36 (d, 1H), 5.21 (d, 1H), 5.11 (d, 1H), 2.86 (septet, 1H), 2.09 (s, 3H), 2.06 (s, 3H), 1.96 (d, 3H), 1.31 (d, 3H) and 1.29 (d, 3H). IR (cm$^{-1}$) 3045 ($v_{CH}$, w), 3031 ($v_{CH}$, w), 2844-2963 ($v_{CH3}$, br), 1597 ($v_{C=N}$, s), 1576 ($v_{C=C(Ph)}$, w), 1541 ($v_{NO2}$, s), 1517 ($v_{C=C(Ph)}$, w), 1458 ($v_{C=C(Ph)}$, w), 1440 ($v_{C=C(Ph)}$, w), 1389 (skel.$_{iPr}$, m), 1369 (skel.$_{iPr}$, m), 1322 ($v_{NO2}$, s), 1044 ($v_{Ru-O-Ph}$, w), 995 ($v_{skel.PCy3}$, w), 793 ($\gamma_{CH}$, w), 779 ($\gamma_{CH}$, w), 683 ($v_{C-Br}$, s), 659 ($v_{Ru-N}$, w), 541 ($v_{Ru-O-Ph}$, w), 514 ($v_{Ru-O-Ph}$, w) and 482 ($v_{Ru-Cl}$, w). Elemental analysis calculated (%) for Ru$_2$C$_{32}$H$_{32}$O$_3$N$_2$Cl$_3$Br (880.95): C 43.63, H 3.66, N 3.18; found: C 43.71, H 3.70, N 3.17.

Bimetallic ruthenium complex 3.e: 0.597 g (73%) as a yellow-green powder. $^1$H-NMR (CDCl$_3$) δ 19.71 (d, 1H), 8.12 (d, 1H), 7.96 (d, 2H), 7.55 (t, 1H), 7.11–7.44 (br m, 8H), 6.66 (t, 1H), 5.42 (d, 1H), 5.27 (d, 1H), 5.12 (d, 1H), 5.01 (d, 1H), 3.41 (septet, 1H), 2.81 (septet, 1H), 2.25 (septet, 1H), 2.01 (s, 3H), 1.67 (d, 3H), 1.29 (d, 3H), 1.26 (d, 3H), 1.21 (d, 3H) and 0.82 (dd, 6H). IR (cm$^{-1}$) 3059 ($v_{CH}$, w), 3040 ($v_{CH}$, w), 2857-2961 ($v_{CH3}$, br), 1607 ($v_{C=N}$, s), 1586 ($v_{C=C(Ph)}$, w), 1527 ($v_{C=C(Ph)}$, w), 1469 ($v_{C=C(Ph)}$, w), 1445 ($v_{C=C(Ph)}$, w), 1383 (skel.$_{iPr}$, m), 1364 (skel.$_{iPr}$, m), 1070 ($v_{Ru-O-Ph}$, w), 1009 ($v_{skel.PCy3}$, w), 806 ($\gamma_{CH}$, w), 794 ($\gamma_{CH}$, w), 688 ($v_{Ru-N}$, w), 564 ($v_{Ru-O-Ph}$, w), 537 ($v_{Ru-O-Ph}$, w) and 508 ($v_{Ru-Cl}$, w). Elemental analysis calculated (%) for Ru$_2$C$_{36}$H$_{42}$ONCl$_3$ (813.18): C 53.17, H 5.21, N 1.72; found: C 53.23, H 5.24, N 1.74.

Bimetallic ruthenium complex 3.f: 0.587 g (68%) as an orange powder. $^1$H-NMR (CDCl$_3$) δ 19.81 (d, 1H), 8.32 (d, 1H), 8.22 (d, 1H), 8.16 (d, 1H), 7.34-7.98 (br m, 8H), 7.06 (d, 1H), 5.39 (d, 1H), 5.25 (d, 1H), 5.08 (d, 1H), 4.97 (d, 1H), 3.51 (septet, 1H), 2.77 (septet, 1H), 2.32 (septet, 1H), 1.98 (s, 3H), 1.74 (d, 3H), 1.34 (d, 3H), 1.20 (d, 3H), 1.16 (d, 3H) and 0.88 (dd, 6H). IR (cm$^{-1}$) 3054 ($v_{CH}$, w), 3037 ($v_{CH}$, w), 2850-2965 ($v_{CH3}$, br), 1602 ($v_{C=N}$, s), 1582 ($v_{C=C(Ph)}$, w), 1550 ($v_{NO2}$, s), 1528 ($v_{C=C(Ph)}$, w), 1464 ($v_{C=C(Ph)}$, w), 1444 ($v_{C=C(Ph)}$, w), 1387 (skel.$_{iPr}$, m), 1366 (skel.$_{iPr}$, m), 1331 ($v_{NO2}$, s), 1100 ($v_{Ru-O-Ph}$, w), 1057 ($v_{skel.PCy3}$, w), 798 ($\gamma_{CH}$, w), 785 ($\gamma_{CH}$, w), 678 ($v_{Ru-N}$, w), 557 ($v_{Ru-O-Ph}$, w), 529 ($v_{Ru-O-Ph}$, w) and 496 ($v_{Ru-Cl}$, w). Elemental analysis calculated (%) for Ru$_2$C$_{36}$H$_{41}$O$_3$N$_2$Cl$_3$ (858.16): C 50.38, H 4.82, N 3.26; found: C 50.44, H 4.85, N 3.25.

EXAMPLE 25

Preparation of Diethyl Diallylaminomethylphosphonate 0.60 g (2.9 mmole) of diethyl allylaminoethylphosphonate was dissolved in 50 ml dry diethyl ether, and 1.17 g (11.6 mmole) triethylamine was added. After 15 minutes of stirring at room temperature, 1.40 g of allylbromide was added dropwise. The mixture was refluxed during 4 days. 50 ml of water was added to the mixture and was subsequently extracted three times with 50 ml CH$_2$Cl$_2$. The organic layers were combined and dried with MgSO$_4$. After filtering MgSO$_4$ and subsequent evaporation of the solvent, the resulting product was further purified with high vacuum distillation, providing 0,6 gram (2,4 mmole, 84% yield) diethyl diallylaminomethylphosphonate having a boiling point of 65° C. under a reduced pressure of 0.1 mbar. This product was further characterised by the following spectra:

$^1$H-NMR (270 MHz, CDCL$_3$): shifts at 1,32 (3H, t, J=7,1 Hz, O—CH$_2$—C$\underline{H}_3$), 1,33 (3H, t, J=6,9 Hz, O—CH$_2$—C$\underline{H}_3$), 2,87 (2H, d, J$_{P-H}$=10,9 Hz, N—CH$_2$—P), 3,25 (4H, d, J=6,27 Hz, 2× N—C$\underline{H}_2$—CH=CH$_2$), 4,14 (4H, m, 2×, O—C$\underline{H}_2$—CH$_3$), 5,19 (4H, m, 2× N—CH$_2$—CH=C$\underline{H}_2$) and 5,83 (2H, m, 2×, N—CH$_2$—C$\underline{H}$=CH$_2$), $^{13}$C-NMR (68 MHz, CDCl$_3$) shifts at 16,50 (d, J$_{P-C}$=4,8 Hz, 2× O—CH$_2$—$\underline{C}$H$_3$), 48,19 (d, J$_{P-C}$=163,6 Hz, N—$\underline{C}$H$_2$—P), 58,09 (d, J$_{P-C}$=7,3 Hz, 2× N—$\underline{C}$H$_2$—CH=CH$_2$), 61,90 (d, J$_{P-C}$=3,6 Hz, 2× O—$\underline{C}$H$_2$—CH$_3$), 118,17 (d, J$_{P-C}$=2,5 Hz, 2× N—CH$_2$—CH=$\underline{C}$H$_2$) and 135,04 (2× N—CH$_2$—$\underline{C}$H=CH$_2$), $^{31}$P-NMR (109 MHz, CDCl$_3$) δ: 26,01, infrared: absorption bands at 1260 cm$^{-1}$ (P=O) and 1643 cm$^{-1}$ (C=C), and mass spectrum: 247 (M$^+$,3), 232 (M+−15,7), 206 (30), 110 (M$^+$—PO(OEt)$_2$, 100), 81 (14), 68 (21) and 41 (26).

EXAMPLE 26

Preparation of Diethyl 1H-pyrrole-1-ylmethylphosphonate 0.1 g (0.41 mmole) of the diethyl diallylaminomethylphosphonate prepared in example 25 was dissolved in 2 ml chlorobenzene, then 0.014 g (0.02 mmole) of the bimetallic ruthenium complex 3.e prepared in example 24 was added and the mixture was stirred for 16 hours at 60° C. The catalyst was removed after evaporation of the chlorobenzene by column chromatography, yielding 0.04 g (0.18 mmole, yield 45%) diethyl 1H-pyrrole-1-ylmethylphosphonate. This product was further characterised by the following spectra:

$^1$H-NMR (270 MHz, CDCl$_3$) δ: 1,27 (6H, t, J=6,9 Hz, 2× 0-CH$_2$—C$\underline{H}_3$), 3,97-4,05 (4H, m, 2× 0-C$\underline{H}_2$—CH$_3$), 4,26 (2H, d, J$_{P-H}$=9,6 Hz, N—CH$_2$—P), 6,17 (2H, s, 2× N—CH=C$\underline{H}$), 6,72 (2H, s, 2× N—C$\underline{H}$=CH), $^{13}$C-NMR (68 MHz, CDCl$_3$) δ: 18,07 (d, J$_{P-C}$=6,1 Hz, 2× 0-CH$_2$—$\underline{C}$H$_3$), 47,50 (d, J$_{P-C}$=157, 5 Hz, N—$\underline{C}$H$_2$—P), 64.48 (d, J$_{P-C}$=6,1 Hz, 2× 0-$\underline{C}$H$_2$—CH$_3$), 110.69 (2× N—CH=$\underline{C}$H), 123.54 (2× N—$\underline{C}$H=CH), $^{31}$P-NMR (109 MHz, CDCl$_3$) δ: 19.72, infrared: absorption bands at 1244 cm$^{-1}$ (P=0) and 1496 cm$^{-1}$ (C=C), and mass spextrum: 217 (M$^+$, 57), 202 (M$^+$−15,17), 174 (13), 107 (29), 80 (M$^+$—PO(OEt)$_2$, 100) and 53 (14).

EXAMPLE 27

Preparation of Diallylglycine Methyl Ester 1.5 g (11.9 mmole) glycine methylester hydrochloride was added to 100 ml dry THF and subsequently, 3.61 g (35.8 mmole) triethylamine was added. After 15 minutes stirring at room temperature, 4.33 g (35.8 mmole) allyl bromide was added dropwise and the mixture was refluxed for 16 hours. 100 ml of 2N HCl was added and then extracted with 100 ml diethyl ether. The aqueous phase was alkalinised after, acid extraction, with $K_2CO_3$ and extracted with $CH_2Cl_2$ (100 ml three times). The organic layer was dried with $MgSO_4$. The product was further purified, after filtration of $MgSO_4$ and evaporation of the solvent, via column chromatography, providing with 100% selectivity 0.78 g (5.75 mmole, yield 49%) diallylglycine methyl ester. This product was further characterised by the following spectra:

$^1$H-NMR (270 MHz, $CDCL_3$) δ: 3,24 (4H; d, J=6,6 HZ, 2× N—$CH_2$—CH=$CH_2$), 3,32 (2H, s, N—$CH_2$—COOMe), 3,69 (3H, s, $COOCH_3$), 5,13-5,24 (4H, m, 2× $CH_2$—CH=C$H_2$), 5,86 (2H, ddt, J=17,2 Hz, J=10,2 Hz en J=6,6 Hz, CH=C$H$=$CH_2$), $^{13}$C-NMR (68 MHz, $CDCl_3$) δ: 51,39 (N—$CH_2$—COOMe), 53,71 ($COOCH_3$), 57,27 (2× N—$CH_2$—CH=$CH_2$), 118,20 (2× $CH_2$—CH=$CH_2$), 135,42 (2× $CH_2$—$CH$=$CH_2$) and 171,75 ($C$OOMe), infrared: absorption bands at 1643 cm$^{-1}$ (CH=$CH_2$) and 1741 cm$^{-1}$ (C=0), and mass spectrum: 169 ($M^+$–41,25), 110 ($M^+$—COOMe, 100) and 41 ($CH_2$=CH—$CH_2$+, 28).

EXAMPLE 28

Preparation of Methyl-1H-pyrrole-1-yl Acetate 0.22 g (1.3 mmole) of the diallylglycine methyl ester prepared in example 27 was dissolved in 3 ml chlorobenzene after which 0.046 g (0,064 mmole) of the bimetallic ruthenium complex 3.e prepared in example 24 was added. The mixture was stirred for 16 hours at 65° C. The catalyst was removed after evaporation of chlorobenzene by column chromatography, providing with 100% selectivity 0.05 g (0.36 mmole, yield 28%) methyl 1H-pyrrole-1-ylacetate. This product was further characterised by the following spectra:

$^1$H-NMR (270 MHz, $CDCL_3$) δ: 3.76 (3H, s, $COOCH_3$), 4.56 (2H, s, N—$CH_2$—COOMe), 6.21 (2H, T, J=1,98 Hz, 2× N—CH=$CH$) and 6.67 (2H, t, J=1,98 Hz, 2× N—$CH$=CH), $^{13}$C-NMR (68 MHz, $CDCl_3$) δ: 50.68 (N—$CH_2$—COOMe), 52.51 ($COOCH_3$), 109.09 (2× N—CH=$CH$), 121.74 (2× N—CH=CH) and 169.22 ($C$OOMe), infrared: absorption band at 1745 cm$^{-1}$ (C=0), and mass spectrum: 139 ($M^+$, 63) and 80 ($M^+$—PO(OEt)$_2$, 100).

The invention claimed is:

1. A five-coordinate metal complex, a salt, or an enantiomer thereof, comprising a metal selected from the group consisting of ruthenium and osmium, a carbene ligand selected from the group consisting of an allenylidene ligand, a cumulenylidene ligand, an indenylidene ligand and a phenylindenylidene ligand, a multidentate ligand and one or more other ligands, wherein at least one of said other ligands is a constraint steric hindrance ligand having a pKa of at least 15, said constraint steric hindrance ligand being a non-ionic prophosphatrane superbase or a N-heterocyclic carbene selected from the group consisting of imidazol-2-ylidene, dihydroimidazol-2-ylidene, oxazol-2-ylidene, triazol-5-ylidene, thiazol-2-ylidene, bis(imidazoline-2-ylidene) bis (imidazolidine-2-ylidene), pyrrolylidene, pyrazolylidene, dihydropyrrolylidene, and pyrrolylidinylidene and benzo-fused N-heterocyclic carbenes, wherein said benzo-fused N-heterocyclic carbene comprises a heterocyclic ring fused to a benzene ring and said heterocyclic ring is selected from the group consisting of imidazol-2-ylidene, dihydroimidazol-2-ylidene, oxazol-2-ylidene, triazol-5-ylidene, thiazol-2-ylidene, bis(imidazoline-2-ylidene) bis(imidazolidine-2-ylidene), pyrrolylidene, pyrazolylidene, dihydropyrrolylidene, and pyrrolylidinylidene, and wherein one or more hydrogen atoms of said non-ionic prophosphatrane superbase or said N-heterocyclic carbene is substituted with a group providing constraint steric hindrance.

2. A five-coordinate metal complex according to claim 1, wherein the multidentate ligand includes at least two heteroatoms through which coordination with the metal occurs.

3. A five-coordinate metal complex according to claim 1, wherein the multidentate ligand includes at least two heteroatoms through which coordination with the metal occurs and wherein at least one of the two heteroatoms is a nitrogen atom.

4. A five-coordinate metal complex according to claim 1, wherein one of said other ligands is an anionic ligand, or one of said other ligands is a solvent and said complex is a cationic species associated with an anion.

5. A five-coordinate metal complex being selected from metal complexes having one of the general formulae (IA) and (IB)

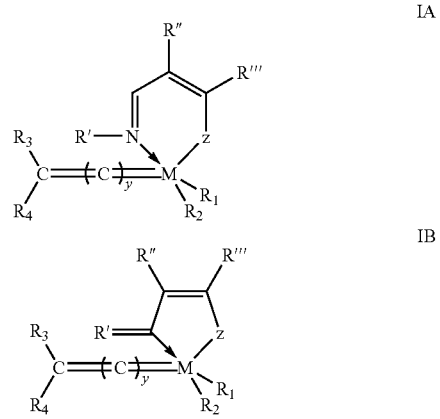

wherein:
M is a transition metal selected from the group consisting of ruthenium and osmium;
Z is selected from the group consisting of oxygen, sulphur, selenium, NR'''', PR'''', AsR'''' and SbR'''';
R'', R''' and R'''' are each a radical independently selected from the group consisting of hydrogen, $C_{1-6}$ alkyl, $C_{3-10}$ cycloalkyl, $C_{1-6}$ alkyl-$C_{1-6}$ alkoxysilyl, $C_{1-6}$ alkyl- aryloxysilyl, $C_{1-6}$ alkyl-$C_{3-10}$ cycloalkoxysilyl, aryl and heteroaryl, or R'' and R''' together form an aryl or heteroaryl radical, each said radical being optionally substituted with one or more substituents $R_5$ each independently selected from the group consisting of halogen atoms, $C_{1-6}$ alkyl, $C_{1-6}$ alkoxy, aryl, alkylsulfonate, arylsulfonate, alkylphosphonate, arylphosphonate, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, alkylammonium and arylammonium;
R' is either as defined for R'', R''' and R'''' when included in a compound having the general formula (IA) or, when included in a compound having the general formula (IB), is selected from the group consisting of $C_{1-6}$ alkylene and $C_{3-8}$ cycloalkylene, the said alkylene or cycloalkylene group being optionally substituted with one or more substituents $R_5$;
$R_1$ is a constraint steric hindrance ligand having a p$K_a$ of at least 15;
$R_2$ is an anionic ligand;

R₃ and R₄ are each hydrogen or a hydrocarbon radical selected from the group consisting of $C_{1-20}$ alkyl, $C_{1-20}$ alkenyl, $C_{1-20}$ alkynyl, $C_{1-20}$ carboxylate, $C_{1-20}$ alkoxy, $C_{1-20}$ alkenyloxy, $C_{1-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, arylphosphonate, $C_{1-20}$ alkylammonium and arylammonium;

R' and one of R₃ and R₄ may be bonded to each other to form a bidentate ligand;

R''' and R'''' may be bonded to each other to form an aliphatic ring system including a heteroatom selected from the group consisting of nitrogen, phosphorous, arsenic and antimony;

R₃ and R₄ together may form a fused aromatic ring system, and y represents the number of sp² carbon atoms between M and the carbon atom bearing R₃ and R₄ and is an integer from 0 to 3 inclusive, salts and enantiomers thereof.

6. A five-coordinate metal complex according to claim 5, having the general formula (IA), wherein R₁ is a constraint steric hindrance ligand having a $pK_a$ of at least 15, said constraint steric hindrance ligand being a non-ionic prophosphatrane superbase or a N-heterocyclic carbene selected from the group consisting of imidazol-2-ylidene, dihydroimidazol-2-ylidene, oxazol-2-ylidene, triazol-5-ylidene, thiazol-2-ylidene, bis(imidazoline-2-ylidene) bis(imidazolidine-2-ylidene), pyrrolylidene, pyrazolylidene, dihydropyrrolylidene, and pyrrolylidinylidene, and benzo-fused N-heterocyclic carbenes, wherein said benzo-fused N-heterocyclic carbene comprises a heterocyclic ring fused to a benzene ring and said heterocyclic ring is selected from the group consisting of imidazol-2-ylidene, dihydroimidazol-2-ylidene, oxazol-2-ylidene, triazol-5-ylidene, thiazol-2-ylidene, bis(imidazoline-2-ylidene) bis(imidazolidine-2-ylidene), pyrrolylidene, pyrazolylidene, dihydropyrrolylidene, and pyrrolylidinylidene.

7. A five-coordinate metal complex according to claim 5 or claim 6, wherein R₂ is selected from the group consisting of $C_{1-20}$ alkyl, $C_{1-20}$ alkenyl, $C_{1-20}$ alkynyl, $C_{1-20}$ carboxylate, $C_{1-20}$ alkoxy, $C_{1-20}$ alkenyloxy, $C_{1-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, aryiphosphonate, $C_{1-20}$ alkylammonium, arylammonium, halogen atoms and cyano.

8. A supported catalyst for use in a heterogeneous catalytic reaction, comprising:
(a) a catalytically active five-coordinate metal complex according to claim 1 or claim 5 or claim 6, and
(b) a supporting amount of a carrier suitable for supporting said catalytically active five-coordinate metal complex (a).

9. A catalytic system for the addition polymerisation of one or more α-olefins having from 2 to 12 carbon atoms, optionally in combination with one or more dienes having from 4 to 20 carbon atoms, comprising the product formed by the mixture of:
(A) a complex according to claim 5 and having the general formula (IB),
(B) an organoaluminum compound, and
(C) a compound selected from Lewis acids, ionic compounds, borane compounds and salts thereof, metallic carboranes, and heteropoly compounds.

10. A five-coordinate metal complex, being suitable for covalent bonding to a carrier, being selected from metal complexes having one of the general formula (IA) and (IB)

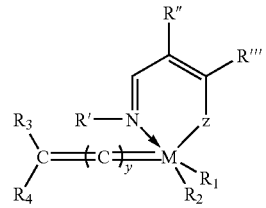

IA

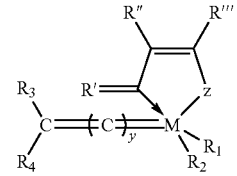

IB wherein:
M is a transition metal selected from the group consisting of ruthenium and osmium;
Z is selected from the group consisting of oxygen, sulphur, selenium, NR'''', PR'''', AsR'''', and SbR'''';
wherein R' and/or R'' is replaced or substituted with a group having the formula:

$$-R_{20}-(CH_2)_n-D-Si-R_{21}R_{22}R_{23} \quad (VIII),$$

R₂₀ is a radical selected from the group consisting of $C_{1-6}$ alkylene, arylene, heteroarylene and $C_{3-8}$ cycloalkylene, the said radical being optionally substituted with one or more R₂₄ substituents each independently selected from the group consisting of $C_{1-20}$ alkyl, $C_{2-20}$ alkenyl, $C_{2-20}$ alkynyl, $C_{1-20}$ carboxylate, $C_{1-20}$ alkoxy, $C_{2-20}$ alkenyloxy, $C_{2-20}$ alkynyloxy, $C_{2-20}$ alkoxycarbonyl, $C_{1-20}$ alkylsulfonyl, $C_{1-20}$ alkynylsulfinyl, $C_{1-20}$ alkylthio, aryloxy and aryl;

D is a divalent atom or radical selected from the group consisting of oxygen, sulphur, silicon, arylene, methylene, $CHR_{24}$, $C(R_{24})_2$, NH, $NR_{24}$ and $PR_{24}$;

R₂₁, R₂₂ and R₂₃ are each independently selected from the group consisting of hydrogen, halogen and R₂₄; and n is an integer from 1 to 20;

provided that at least one of R₂₁, R₂₂ and R₂₃ is selected from the group consisting of $C_{1-20}$ alkoxy, $C_{2-20}$ alkenyloxy, $C_{2-20}$ alkynyloxy, $C_{2-20}$ alkoxycarbonyl, $C_{1-20}$ alkylsulfonyl, $C_{1-20}$ alkynylsulfinyl, $C_{1-20}$ alkylthio and aryloxy;

R'', R''' and R'''' are each a radical independently selected from the group consisting of hydrogen, $C_{1-6}$ alkyl, $C_{3-10}$ cycloalkyl, $C_{1-6}$ alkyl-$C_{1-6}$ alkoxysilyl, $C_{1-6}$ alkyl- aryloxysilyl, $C_{1-6}$ alkyl-$C_{3-10}$ cycloalkoxysilyl, aryl and heteroaryl, or R'' and R''' together form an aryl or heteroaryl radical, each said radical being optionally substituted with one or more substituents R₅ each independently selected from the group consisting of halogen atoms, $C_{1-6}$ alkyl, $C_{1-6}$ alkoxy, aryl, alkylsulfonate, arylsulfonate, alkylphosphonate, arylphosphonate, $C_{1-6}$ alkyl-$C_{1-6}$ alkoxysilyl, $C_{1-6}$ alkyl-aryloxysilyl, $C_{1-6}$ alkyl-$C_{3-10}$ cycloalkoxysilyl, alkylammonium and arylammonium, or R'' is a group of Formula (VIII);

R' is either as defined for R'', R''' and R'''' when included in a compound having the general formula (IA) or, when included in a compound having the general formula (IB), is selected from the group consisting of $C_{1-6}$ alkylene and $C_{3-8}$ cycloalkylene, the said alkylene or cycloalkylene group being optionally substituted with one or more substituents $R_5$, or R' is a group of Formula (VIII);

$R_1$ is a constraint steric hindrance ligand having a p$K_a$ of at least 15;

$R_2$ is an anionic ligand;

$R_3$ and $R_4$ are each hydrogen or a hydrocarbon radical selected from the group consisting of $C_{1-20}$ alkyl, $C_{1-20}$ alkenyl, $C_{1-20}$ alkynyl, $C_{1-20}$ carboxylate, $C_{1-20}$ alkoxy, $C_{1-20}$ alkenyloxy, $C_{1-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl $C_{1-20}$ alkylsulfonate, arylsulfonate, $C_{1-20}$ alkylphosphonate, aryiphosphonate, $C_{1-20}$ alkylammonium and arylammonium;

R' and one of $R_3$ and $R_4$ may be bonded to each other to form a bidentate ligand;

R''' and R'''' may be bonded to each other to form an aliphatic ring system including a heteroatom selected from the group consisting of nitrogen, phosphorous, arsenic and antimony;

$R_3$ and $R_4$ together may form a fused aromatic ring system, and y represents the number of sp$^2$ carbon atoms between M and the carbon atom bearing $R_3$ and $R_4$ and is an integer from 0 to 3 inclusive, and enantiomers thereof.

11. A five-coordinate metal complex according to claim 5 or claim 6, wherein $R_1$ is 1,3-bis(2,4,6-trimethylphenyl)-4,5-dihydroimidazol-2-ylidene.

12. A five-coordinate metal complex according to claim 1, wherein said group providing constraint steric hindrance is selected from the group consisting of tert-butyl, substituted $C_{3-10}$ cycloalkyl, aryl having two or more $C_{1-6}$ alkyl substituents, and heteroaryl having two or more $C_{1-6}$ alkyl substituents.

13. A five-coordinate metal complex according to claim 10, having the general formula (IA), wherein $R_1$ is a constraint steric hindrance ligand having a p$K_a$ of at least 15, said constraint steric hindrance ligand being a non-ionic prophosphatrane superbase or a N-heterocyclic carbene selected from the group consisting of imidazol-2-ylidene, dihydroimidazol-2-ylidene, oxazol-2-ylidene, triazol- 5-ylidene, thiazol-2-ylidene, bis(imidazoline-2-ylidene) bis(imidazolidine-2-ylidene), pyrrolylidene, pyrazolylidene, dihydropyrrolylidene, pyrrolylidinylidene, and said N-heterocyclic carbenes, wherein the heterocyclic ring is fused to a benzcne ring, and wherein one or more hydrogen atoms of said non-ionic prophosphatrane superbase or said N-heterocyclic carbene is substituted with a group providing constraint steric hindrance.

14. The metal complex of claim 1 or 5, wherein said complex is dissolved or suspended in a solvent.

15. A five-coordinate metal complex, a salt, or an enantiomer thereof, comprising a metal selected from the group consisting of ruthenium and osmium, a carbene ligand, a multidentate ligand and one or more other ligands, wherein at least one of said other ligands is a constraint steric hindrance ligand having a pKa of at least 15, said constraint steric hindrance ligand being a N-heterocyclic carbene that is dihydroimidazol-2-ylidene, and wherein one or more hydrogen atoms of said N- heterocyclic carbene is substituted with a group providing constraint steric hindrance that is selected from the group consisting of tertbutyl, substituted $C_{3-10}$ cycloalkyl, 2,6-dimethylphenyl, 2,4,6-triisopropylphenyl, or 2,6-diisopropylphenyl, and heteroaryl having two or more $C_{1-6}$ alkyl substituents.

16. A five-coordinate metal complex, a salt, or an enantiomer thereof, comprising a metal selected from the group consisting of ruthenium and osmium, a carbene ligand, a multidentate ligand and one or more other ligands, wherein said multidentate ligand is a bidentate ligand which forms a five-membered chelate ring when complexed to said metal, and wherein at least one of said other ligands is a constraint steric hindrance ligand having a pKa of at least 15, said constraint steric hindrance ligand being a a non-ionic prophosphatrane superbase or a N-heterocyclic carbene selected from the group consisting of imidazol-2-ylidene, dihydroimidazol-2-ylidene, oxazol-2-ylidene, triazol-5-ylidene, thiazol-2-ylidene, bis(imidazoline-2-ylidene) bis(imidazolidine-2-ylidene), pyrrolylidene, pyrazolylidene, dihydropyrrolylidene, pyrrolylidinylidene and benzo-fused N-heterocyclic carbenes, wherein said benzo-fused N-heterocyclic carbene comprises a heterocyclic ring and wherein one or more hydrogen atoms of said non-ionic prophosphatrane superbase is substituted with a group providing constraint steric hindrance.

* * * * *

UNITED STATES PATENT AND TRADEMARK OFFICE
CERTIFICATE OF CORRECTION

| | | |
|---|---|---|
| PATENT NO. | : 7,687,635 B2 | |
| APPLICATION NO. | : 10/894308 | |
| DATED | : March 30, 2010 | |
| INVENTOR(S) | : Verpoort et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1498 days.

Signed and Sealed this
Eighth Day of February, 2011

David J. Kappos
*Director of the United States Patent and Trademark Office*

UNITED STATES PATENT AND TRADEMARK OFFICE
CERTIFICATE OF CORRECTION

PATENT NO. : 7,687,635 B2  Page 1 of 1
APPLICATION NO. : 10/894308
DATED : March 30, 2010
INVENTOR(S) : Francis W. Verpoort et al.

It is certified that error appears in the above-identified patent and that said Letters Patent is hereby corrected as shown below:

In the Claims

Column 75, Claim 7, Line 44, replace "aryiphosphonate" with --arylphosphonate--.

Column 77, Claim 10, Line 13, replace "aryiphosphonate" with --arylphosphonate--.

Column 78, Claim 13, Line 3, replace "benzcne" with --benzene--;

Claim 15, Line 19, replace "tertbutyl" with --tert-butyl--;

Claim 16, Line 31, replace "being a a non-ionic" with --being a non-ionic--;

Claim 16, Line 40-41, replace "non-ionic prophosphatrane superbase" with --constraint steric hindrance ligand--.

Signed and Sealed this
Fourteenth Day of May, 2013

Teresa Stanek Rea
*Acting Director of the United States Patent and Trademark Office*